US011833168B2

(12) United States Patent
Bui et al.

(10) Patent No.: US 11,833,168 B2
(45) Date of Patent: Dec. 5, 2023

(54) COMPOUNDS AND METHODS FOR INCREASING STMN2 EXPRESSION

(71) Applicants: Ionis Pharmaceuticals, Inc., Carlsbad, CA (US); Ludwig Institute For Cancer Research, Zurich (CH)

(72) Inventors: Huynh-Hoa Bui, San Diego, CA (US); Don W. Cleveland, La Jolla, CA (US); Ze'ev Melamed, San Diego, CA (US)

(73) Assignees: Ionis Pharmaceuticals, Inc., Carlsbad, CA (US); Ludwig Institute For Cancer Research, Zurich (CH)

( * ) Notice: Subject to any disclaimer, the term of this patent is extended or adjusted under 35 U.S.C. 154(b) by 0 days.

(21) Appl. No.: 16/973,652

(22) PCT Filed: Jun. 14, 2019

(86) PCT No.: PCT/US2019/037215
§ 371 (c)(1),
(2) Date: Dec. 9, 2020

(87) PCT Pub. No.: WO2019/241648
PCT Pub. Date: Dec. 19, 2019

(65) Prior Publication Data
US 2021/0252039 A1 Aug. 19, 2021

Related U.S. Application Data

(60) Provisional application No. 62/685,192, filed on Jun. 14, 2018.

(51) Int. Cl.
*C12N 15/11* (2006.01)
*A61K 31/7125* (2006.01)
*C12N 15/113* (2010.01)

(52) U.S. Cl.
CPC ........ *A61K 31/7125* (2013.01); *C12N 15/113* (2013.01); *C12N 2310/315* (2013.01); *C12N 2310/3181* (2013.01); *C12N 2310/321* (2013.01); *C12N 2310/3341* (2013.01); *C12N 2310/341* (2013.01); *C12N 2310/344* (2013.01); *C12N 2310/346* (2013.01); *C12N 2310/351* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |

(Continued)

FOREIGN PATENT DOCUMENTS

WO   WO-02085309 A2 * 10/2002 ......... A61K 31/7088
WO   WO-2017106370 A1 * 6/2017 ............. A61P 27/02

(Continued)

OTHER PUBLICATIONS

Extended EP Search Report for 19819551.3 dated Jul. 6, 2022, 6 pages.
Gonzalez, "In Vitro Studies of Amyotrophic Lateral Sclerosis Using Human Pluripotent Stem Cell-Derived Motor Neurons" Harvard University ProQuest Dissertations Publishing (2015) from (https://www.proquest.com/docview/1751069017/), 1-24.
Branch et al., "A good antisense molecule is hard to find," TIBS (1998) 23:45-50.
Chen et al., "Modulation of nuclear REST by alternative splicing: a potential therapeutic target for Huntington's disease" J Cell Mol Med (2017) 21: 2974-2984.

(Continued)

*Primary Examiner* — Ekaterina Poliakova-Georgantas
(74) *Attorney, Agent, or Firm* — McNeill Baur

(57) ABSTRACT

Provided are compounds, methods, and pharmaceutical compositions for increasing the amount or activity of STMN2 RNA in a cell or animal, and in certain embodiments increasing the amount of STMN2 protein in a cell or animal. Such compounds, methods, and pharmaceutical compositions are useful to ameliorate at least one symptom of a neurodegenerative disease. Such symptoms include ataxia, neuropathy, synaptic dysfunction, deficits in cognition, and decreased longevity. Such neurodegenerative diseases include amyotrophic lateral sclerosis (ALS), frontotemporal dementia (FTD), Alzheimer's disease (AD), and dementia with Lewy bodies (DLB).

36 Claims, No Drawings

Specification includes a Sequence Listing.

(56) References Cited

U.S. PATENT DOCUMENTS

| | | |
|---|---|---|
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2005/0246794 A1* | 11/2005 | Khvorova .......... C12N 15/1137 536/23.1 |

(56) References Cited

U.S. PATENT DOCUMENTS

| | | |
|---|---|---|
| 2006/0148740 A1 | 7/2006 | Platenburg |
| 2007/0031844 A1 | 2/2007 | Khvorova et al. |
| 2007/0037165 A1 | 2/2007 | Venter et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |
| 2013/0130378 A1 | 5/2013 | Manoharan et al. |
| 2014/0107330 A1 | 4/2014 | Freier et al. |
| 2015/0018540 A1 | 1/2015 | Prakash et al. |
| 2015/0126718 A1* | 5/2015 | Prakash ........... C07H 21/04 536/17.1 |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2016/0145617 A1* | 5/2016 | Kordasiewicz ........ A61P 25/28 536/24.5 |
| 2017/0182082 A1 | 6/2017 | Swayze |

FOREIGN PATENT DOCUMENTS

| | | |
|---|---|---|
| WO | WO 2019/241648 | 12/2019 |
| WO | WO 2020/150290 | 7/2020 |

OTHER PUBLICATIONS

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Crooke, St., et al., "Antisense Drug Technology" Second Edition, CRC Press (2008) Chapters 1-28.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Gautschi et al., "Activity of a novel bcl-2/bcl-xLbispecific antisense oligonucleotide against tumors of diverse histologic origins" J. Natl. Cancer Inst. (2001) 93:463-471.

GenBank NC_000008.11 *Homo sapiens* chromosome 8, GRCh38.p7 Primary Assembly [online] Jun. 6, 2016 [retrieved Aug. 27, 2019]. Available on the internet: https://www.ncbi.nlm.nih.gov/nuccore/568815590?sat=46&satkey=133828806.

International Search Report for PCT/US19/037215 dated Sep. 20, 2019.

Iwamaru et al., "Proximity of SCG10 and prion protein in membrane rafts" J Neurochem (2016) 136: 1204-1218.

Klim et al., "ALS-implicated protein TDP-43 sustains levels of STMN2, a mediator of motor neuron growth and repair" Nat Neurosci (2019) 22: 167-179.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

Melamed et al., "Premature polyadenylation-mediated loss of stathmin-2 is a hallmark of TDP-43-dependent neurodegeneration" Nat Neurosci (2019) 22: 180-190.

Melamed et al., "Premature polyadenylation-mediated loss of stathmin-2 is a hallmark of TDP-43-dependent neurodegeneration" Meeting Abstract Amyotrophic Lateral Sclerosis and Frontotemporal Degeneration (2019) 20 Suppl 1 (1998-199).

Melamed "TDP-43 knockdown in mature iPSC-derived motor neurons induces efficient silencing of stathmin-2 mRNA" Presentation for RNA Metabolisms nad New Mechanisms of Toxicity (Jun. 21, 2018) San Diego, CA.

New England Biolabs 1998/99 Catalog (cover page and pp. 121 and 284).

Ooi et al., "BRG1 Chromatin Remodeling Activity is Required for Efficient Chromatin Binding by Repressor Element 1-silencing Transcription Factor (REST) and Facilitates REST-mediated Repression" J Biol Chem (2006) 281: 38974-38980.

Reynolds et al., "Rational siRNA design for RNA interference" Nature Biotechnology (2004) 22(3):326-330.

Rowland et al., "Amyotrophic lateral sclerosis" N. Engl. J. Med. (2001) 344: 1688-1700.

Sanghvi et al., "Heterocyclic Base Modifications in Nucleic Acids and Their Applications in Antisense Oligonucleotides" Antisense Research and Applications (1993) pp. 273-288.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Woolf et al., "Specificity of antisense oligonucleotides in vivo" PNAS (1992) 89: 7305-7309.

\* cited by examiner

SEQUENCE LISTING

<160> NUMBER OF SEQ ID NOS: 321

<210> SEQ ID NO 1
<211> LENGTH: 61000
<212> TYPE: DNA
<213> ORGANISM: Homo sapiens

<400> SEQUENCE: 1

```
actggattca tccattttga atcattttca acactgtatt atttattatt tcacaaattg      60
tttttaactg tctaccacgt gaatcatgaa accaaccact aggaagggta taaagatata     120
cactattcat tctctacctt tcaaaggttt aaatgtattg gaaacactaa atatagtcat     180
agtacttaaa attactatat atccatgatg gcttagacag ttcatacatg ataacccttc     240
agtctaccca aatccccaca cgacagatac tggttgtcct tagtttatac tgtgcaaatg     300
```

```
tagtacctat tctttgagtg tccacccatt cccatcaaaa ccatttcctt caggaaaagc    360
tgatctcacc tccagacctc tagggccaac tctatctata tggttagacg aaacagcaaa    420
tgcactttta ttattagtgc cagtttgggt tattttttca aattttttgca acaaagtgtg    480 atccacaata cacaagatca tattcactcc cccaaattaa tattttctta aagagatggg    540
tgttatattt tccttcactt tctatttttc agacattaag gagaagcttg gctggcatca    600
caaaagcctg aaacatcatc aaataaatat ttgttgaata aattagctga acaaatgaat    660
aagtgaataa catattgaat atgaaataat ttttctgttc atatttcacc cttactttcc    720
catgtgaata tgcatgatac catattgtaa tgataaaaga aaacaaaaaa caatttgata    780
atggcacagc cctttgaatt tatttgtgtt ttcttagctg attgacaatt ttgcctacta    840 tcttttttatt ctatggtaaa tcatattgac ctactctctt ccctgtttga cattatttaa    900
aaatcattca taactgaagt taggtggcta acacctagaa aatcggaaat agaaaagagt    960
cacatatgtg acccttaggg cagtagaatg agtgttttgt tttcctcata gtcatcaaaa   1020
gtgcaatcga tttcattcag cagccaactg cagttgttaa agaaactaat gccatgactt   1080
agggcccttg ttctccaagg aagctgaaga atgtgtagag atgacacaca gcctgagggg   1140 aaaggggtgtg gtgggagaaa gagaaatact ttgaaaatat tagtcacaca gacatgctga   1200
agatccttca cctcatgagt gataactact ccagtgagag gtgattaact gttacattta   1260
aagtgggaaa tgcctatata tagagagaaa atggttattt atttccagac cctgccaact   1320
tccatattgc tctcttgctg tgtcatagtc acagacctgt tcaaagatag gaaatataat   1380
ttctaatctt cctgttcaag aaataatttt attgatctcc acttcatctt ttattttccc   1440
catgattcag caggtcaaaa ctgttccagt tccagtagca tcctatcagt cagcaaaatg   1500
tccatgaggt taaaatgtct tacaagttaa taggaggtga agaaattcat ttcagcacca   1560
aggagagtgc cctgctatttt tcaattggtt ttatgtatttt gaaactgtgt attgttcctg   1620
aggatagaaa aaaagttga aatgtgattg gacagaaagc tgctaaaaac ctatttttaat   1680 aagaagaaaa aaatacattc attttttctga aattaaaaac ttgccagggt ttcatacctg   1740
ttcatgattg caacaatgtg ctcttctttt ggctttcaaa cgtcggaatt agcaattctt   1800
tgcctatttt tctaatatta aaaccagttt ctgcatggaa ttagactggc tcaataaagt   1860
tacagaagag ttaaattagc agtaattaaa aacttcatgc agcaactcct aaactttttc   1920
tcaccatttt cagagctgtg cacatggtaa atgctcaata catatttaag tcaagtgaaa   1980
gagaacaaat gaatgactgg catccattaa gtgagaagga ggaactaata aatgccttgt   2040
ttgtaatgaa agtcattttt tgcaactagt ctcaaagatc ctcacatacg acattgctca   2100
atccgaaact tgaacacagc cttcctgggc ctacataaac gtagtctctc tggatctcag   2160
aaaaataatg acccagacca cacctttcat ctcttctaag ttttccatgt aaagcattct   2220
ccttagagcc ctggaaaggt tactaaaatt ttgacccact taatcctaca ccttcagggc   2280
aacatggcat tcacctgtgg tttccttaat gcccaaacca gccagccaac ctgttttctg   2340
ccgtgttaac aaatggacag gacacaggca ccagaggtta aacttcttc ctcttccccc   2400 atgtccccag gtggaccatt attaccatcc ctattcccaa gcaaccaggt agcccctttcc   2460 tctgtgccaa gggaagaaaa caccatgctt ccctctcctg agagaccttc aagagtttag   2520
agacgcctaa gtccagctgt gctaaaagat aaggacaat aatgcaagtc tgctctgagc   2580
tgccaccata gccagacata gggtagccct gaaagactag aaccaaggac agagccaaag   2640
gtgaaagaaa atatgaaaaa gtgaaaacac agtatttaaa cagaattttc caacagcctg   2700
```

-continued

| | | | | | |
|---|---|---|---|---|---|
| catatagtga | ggacttctca | agcttctgaa | tccttttcca | ttgaattgtg | caatggcaca | 2760 |
| tgtatgagca | aagtcaagcc | tcctggctcc | caggtaggca | cagcccagtt | cttagctcct | 2820 |
| aggaagcttc | agggcttaaa | gctccactct | acttggactg | tactatcagg | cccccaaaat | 2880 |
| gggggggagcc | gacagggaag | gactgatttc | catttcaaac | tgcattctgg | tactttgtac | 2940 |
| tccagcacca | ttggccgatc | aatatttaat | gcttggagat | tctgactctg | cgggagtcat | 3000 |
| gtcaggggac | cttgggagcc | aatctgcttg | agcttctgag | tgataattat | tcatgggctc | 3060 |
| ctgcctcttg | ctctttctct | agcacggtcc | cactctgcag | actcagtgcc | ttattcagtc | 3120 |
| ttctctctcg | ctctctccgc | tgctgtagcc | ggacccttg | ccttcgccac | tgctcagcgt | 3180 |
| ctgcacatcc | ctacaatggc | taaaacagca | atgggtaagg | cactgcgcct | cgttctccgt | 3240 |
| cggctctacc | tggagcccac | ctctcacctc | ctctcttgag | ctctagaagc | attcagagat | 3300 |
| attttataaa | gaaaagatg | ttaatggtaa | cacaggacca | ggaaggacag | ggcagttctg | 3360 |
| ggggaggtgg | gagggcagag | aagaggtcta | tggaaatcta | aagcgaagaa | tttcttttaa | 3420 |
| aaggtagaag | cgggtaagtt | gccctcctat | gggtagagaa | tttattctgt | ttccatattt | 3480 |
| aaaattagga | ctcaatcgtg | aggggaggaa | gctaccttaa | ctgtttgcct | taaatgggct | 3540 |
| taagggacat | tttggaaagt | gctttataac | gacctttttt | tttttattt | cttctctagt | 3600 |
| ttaagaagaa | aataggaaag | gggtaaaggg | aaggtgggag | aaaggaaaaa | gaaaattgca | 3660 |
| aagtcaaagc | ggtcccatcc | cgctgtttga | agatgggtg | gagacggggg | gagggatgg | 3720 |
| agagaactgg | gcacatttta | cggtattgtc | tcgtcgaaga | aaccgctagt | cctgggtgc | 3780 |
| ggtgcaggga | ggtaagacgg | cggggacag | ggtgggggta | ggacctccgc | tcctttgttt | 3840 |
| tagggcaagg | gaggggaagg | agagaggaag | tcgcggaggg | cgtggagggc | gcggtgggc | 3900 |
| agctgcaggg | gcggggaagc | gcgcggcagg | gaggggtgga | gggacagcgg | cttcgaaggc | 3960 |
| gctggggtgg | ggtttctttg | tgtgcggacc | agcggtcccg | gggggaggca | cctgcagcgc | 4020 |
| tgggcgcaca | atgcggacag | ccccacccag | tgcggaaccg | cgcagccccg | cccccccgcc | 4080 |
| cggtgctgca | tcttcattcg | aaagggggtc | gggtggggag | cgcagcgtga | cacccaggag | 4140 |
| cccaaccctg | cggggacagc | ggcgccacgc | cccgcgctcc | ccgctcccga | ctcccgccg | 4200 |
| cggcttccaa | gagagacctg | accactgacc | ccgccctccc | cacgctggcc | tcattgttct | 4260 |
| gcttttaaga | gagatgggaa | aagtgggtta | acatttttct | tttcggaagc | aaattacata | 4320 |
| gagtgtttag | acatagacac | agataaaggg | ttctttgaag | acctttgatc | gtttgcggga | 4380 |
| aaagcttcta | gaacctagac | atgtgtatgt | ataataatag | agatgacatg | aaatcgtata | 4440 |
| taaagcaaaa | gaggtcaaag | tcttaagtta | agccacgcga | aatttccgtt | ttgtgggtca | 4500 |
| gacagtgcca | aatatcggca | atttcataag | ctcagagaga | caagacagtg | gagacacagg | 4560 |
| atgaccggaa | aagattctgg | attcagggcc | ttcatccgca | attggtcttg | tgccttgagt | 4620 |
| gcccacggtt | ctggcgctca | gtggccccgg | ggtgaaaagg | cagggtgggg | cctgggtcc | 4680 |
| tgtggcagct | ggaagcacgt | gtcccccggg | acttggttgc | aggatgcgga | gacagggaaa | 4740 |
| gctgccgaaa | ggactccatc | tgcgcggctc | cgccctgccc | taccctcccc | gcggagccgg | 4800 |
| ggagacctca | ggctccgaga | ctggcgggga | agaggaatat | gggagggca | gttgagctgt | 4860 |
| atgcagtcct | ggaacctctt | ttttcagccc | cgcagtccac | aacggcccga | gcacccttg | 4920 |
| atgtgcgcag | accccccggcg | tggctctcag | ccccagcacc | gagcccctcc | cagccaagcg | 4980 |
| ggtggctctg | cagaaaagct | ggctcgagcc | ccgcccggcc | acacaaaggc | gcggcccac | 5040 |

-continued

```
ccagcccggg cgcgagaccg cagaggtgac ccccttccca gggattcagg gagggctgtc    5100
tcttctcgcc cacccacggt ccgcggagct cggggctttt tttcccccag cccaagcccc    5160
ccgcccaccc tctgttctct atgatttttcc agaatggaga ccccgcgagg ggcttctcta    5220
agggagaccc tcgctcctcc agcggggcgc ggctcggccc caccccctccc agctgaggcc    5280 cagagccgcc taccgctggc cgggtggggg cgcacgtggc gactgggtgt gtggagcgca    5340
gccagccctg cagagcccg cgccgcgccc tgcgctcccc tccccggagt tgggcgctcg    5400 ccccgcggt gcagccgggg agaccggttt ctgcgcagtg tcctgagcta cccccgcttt    5460
ccacaattcg cagttcactc gcacgtccag aaaggttctg agaatgggtg gtgggggcga    5520
tctcgcctcg ctttctgcac ccctcagaaa ggtttccgct gcaggctagt ggctgcaaac    5580
tcatcgtcat catcagtatt attatcattt caaatcgttg ttattattta atgattcagt    5640
agccttgttt gttctcattt gttcaaaagg gacgtggatt gctcttggtt aaggattaac    5700
ccttgttgcg ttcgctttgc ttcctcctaa ttgccctcat ccctttcccc cacaaaaagg    5760
taaatttgtc tccagttgtt cattttaagt tataaagcaa atatattttt gcttcctgcc    5820
aggattatgt atgttcatgt ggctaagata catgtgcaag tgcttgctaa gagcagggtt    5880
tgtgtgccaa cgattgctgg aaaattctct gcaaagaatt gtttgtggct gcaatgggtg    5940
agaatacaca tatataattg agatgatctt caacataagg ttatatctat aaatatataa    6000
atatagttta tgcacaaaat tttaagtttt ttcccctgaa actgttcttc caactgctga    6060
ttcttgatac agcctcaatc ctacacagat acatggatcg tgaaatggta gccgccatcc    6120
aaataaaaat cccaccccaa atatgacaaa cgcaagcatc ctttctggcc ataatttaac    6180
tgcatttgca aatcatgaaa aaaacactac ttctgcagta ttaaaataat agattttgaa    6240
attaattcca atttcaaaga taattaatta tcagggcgag tgcttttttc ctgattcatt    6300
aaacaattat gtattcagca tgattgtaag aggtgcatat aatattcccc attatctttt    6360
ctaatgaagt gggcaccttc tgaatggata tataagtaac tagaaatgaa aagctgagga    6420
tttggtcaga atttcaggat aaaactgaaa gaaatggcag tagtttatca attaatctca    6480
tgtatttagt ttataccagg tgagtaagct gagcctgcaa taaacactct ctgtcccagt    6540
gtaacacgtc gcaggtagct agaatgatag gataaattaa tagaccttgt ggtgtttgtc    6600
tatgcacgtt aaaattctct gagagaaagt atattttaaa atgataatta agattggaca    6660
tttgtgctat taaaatctac aactttagtc aaaattcaca atggtttttt tttacaataa    6720
tgtgacttac agatttgtag taaattattc tattctaaaa gagaaatgag tgttttatt    6780 gttacagcta ttacctcatt aatattttta gcaaactttt atttgttgca ttgaaagcag    6840
ttttaattac tttgggtttt tattttcaa attactaatg gatagatggt ggaataagca    6900
tttaatcatt tggcacaata tgacttccat caaatagctc attctcagtg attaaaaat    6960 gctacaagag gctacaattt actcagattc aggaaatgtc ctttcagagt gccataaggc    7020
tgattcatat aataaaatag ttttcttccc tataatttaa gatcaaatag ttacttagtt    7080
ctgtgaatac ctagcagtag ctatcaaaca gaattttaaa gttaaatctg tacaactaac    7140
aatgaagtgg aggatgaatc gatacatatt gaatggaaga ctttgtcatt gataaattca    7200
ggccatcttt aggaaaattc cggatttatc aatcaccatt attttttact tcaactgagt    7260
gtgactgatc acatgctcag gctaccttgg tagctcattg ctcacaggag gctgaaaaaa    7320
gctggcctcc gagcaggagg aagctcagag cacaaaccta ggcctgggcg tggccactgg    7380
gagctgctga tagcgaaccc cagctcacac cagtttcttt tttggtcgtg ggaagaaaaa    7440
```

```
cacatattat cctgttgtca caagatctgt gaccttatat gaaaaaatgc tagaatttt    7500
tcattaaaaa agaaaatact gaactagcca gtgacccaga tgttttcaga acctagactg   7560
gttctgtcca ttggaaaacc tcggtgtctg cattaacttt tcaccacact agagggcaat   7620
catgttctct aaaaaagcag atgattgatg taaacctagt tccaaatatt aactgtttaa   7680
taaaatcttt tcttttacca ggaacattca agtgtttatt caataagctg atgccatgct   7740
ttaccctagt ggatgaacag agcttgtaca attttcaagg agacaggatg aaatgagtgg   7800
tcataatctg aaagtagata cacgccctgg ttaattattc cctgatggtt ttacttctca   7860
gttttattac attgttatta taataccatt tatgttactt ctgagattt gtagtggata    7920
aatagtagaa aaatgtcagt agtaatagca aagttattta gcagccgaat attttaatgc   7980
ttaaaaataa aggaataaat taagaaaat cattgtttac ttcttcatcg attgaaatgt    8040
gcccctgtt cagagcacat ctgaatatca gagtctccac ctgcagagaa catgcagctt    8100
agcgagtaaa acaggcaggt atgtgatact gaggaggtgt accaaaaact gactgctgtt   8160
attttcccca tcttctaagt ctgtctttct tttccattta aagataccttt tttaaatcta  8220
atccaatgtg atttcaatct agttttatca gatttcaaca attattgagc atctccttgt   8280
agtggttttc tgtttattag aaaatcgatg ttaattttaa cgaagtaaga agaaatatat   8340
aagtataaac taattttggg tatcatcaaa agtggattt ttaaatatgc attgatagaa    8400
ttatttttg attacatttt atgtaattct aatccagcta taaaatattt aatagtgtca    8460
tattactgtg ttcctcaaac tttgatgtgc atatgaatta cctttgatt tcattaaaat    8520
gcaaattctg attcaataca tctggcttga ggcagacatt ctgtcttccg aacaagctcc   8580
cagatgatgc tgattctgac cactaaacac atcagtttta gggatattaa cttgtaatat   8640
acaggtatcc ctcctggtaa gctctggtat tatgtcttaa catttttaaa tctatggtaa   8700
tctttacaaa atattttact tccgaactca tatacctggg gattttatta ctctgggaat   8760
tatgtgttct gccccatcac tctctcttaa ttggattttt aaaattatat tcatattgca   8820
ggactcggca aagaccttc gagagaaagg tagaaaataa gaatttggct ctctgtgtga    8880
gcatgtgtgc gtgtgtgcga gagagagaga cagacagcct gcctaagaag aaatgaatgt   8940
gaatgcggct tgtggcacag ttgacaagga tgataaatca ataatgcaag cttactatca   9000
tttatgaata gcaatactga agaaattaaa acaaagatt gctgtctcaa tatatcttat    9060
atttattatt taccaaatta ttctaagagt atttcttcct gaataccatg tgagaaaatt   9120
cttaagaatt tattgagtat gactgtatat ttgaaaagag tgtttcttc tgcttatcta    9180
agccaataaa ggatcttcat tattcaattc taactttcta aggaagtcaa cctacagatc   9240
agaaagagga tcttcaagga atagcatcaa agacatagtc aggtctccca tgcagtgact   9300
ggctgaccat gcagccatta ccacctttct ggaaatatta tgctgcaaaa atgatacaat   9360
acacgaaata tctcaaatta aaaaatataa catttcccaa atagggcact aaaaacatga   9420
tcccaaataa aactagcttc agggtttgca gaatatactg ttactcaaca caaagttgga   9480
ctaagtctca aagttagcca ttcagttgtt gttaacagtt catttcaggg tctctcagaa   9540
gctgggaaac tttccatttt tgcaatttct tgtacattga aggaaggaa gacacactta    9600
agacagcatt acaaaagtaa ttcatgtttt aaatgtttaa ttctggcagt cgggcagggc   9660
tctctgtata acctcatttg gagatgacaa aaatctaaac ttgagggcct cgagccaata   9720
agtcttccta tttctttact caaacatttt cccgcaatgg tgctttcttt caactgtttt   9780
```

```
tctggtgtat tcataaattc cagattctct atgggaagta acttttattg attgatttaa    9840
cccttgtata gcacatataa catgcaaggc attgttctaa gaactttcca catattaact    9900
gtgttaatca cttaataatc ctaagtaggt tctattacag atatggaaac tgaggcacag    9960
aaagttgaag tatcttactc aaggtcacac agttagtcag atccagaatt tgggcccagg   10020
ccatctggct tcggaatcca tctttcaccg attgctgcta gtctcatatc tgttccatgt   10080
tagaggtgag ctcccattgc agaggtcaca cctgtgatat caccatttta tttaaacaga   10140
ccagagatgg tcttctcctt tctgatcaca gactcacctt gaagagaaaa acttccaaa    10200 ttgatgccta gttttaatag cttacctggg gcttattcaa ataattgcca tgatttaggc   10260
tttgggagaa agagagctat gaggccgtgt gggttgtaac gtatgagaca catggcgttc   10320
tgcaggctca gcacagcatc gatttctggt gggaacacac tctgatgacc agttccagaa   10380
ataacattga cttaatctcc tcagtcccat catggttagc acatttcaaa atgcctcctt   10440
aactacttcc ataggccaga gatatttagt tttaacattt tgttgaataa aataaattta   10500
cacattcaca tttaatataa ctattagatg ttatttcaag attctcttca tattaccatc   10560
aaagcaggca ggcaggcagg agagaactgt aggaaggttt tgaatcccct gtgaaacatt   10620
tttaattatc ttttaataaa ggaatcaggc cctgtcattt gtcaaggaga catttgcagt   10680
agtaaagctt gtgtttataa tatccatttt tattagtcat gattaaagat aacatttgtg   10740
tacatttgtt ctcacaaaac acttttatat gagtgtaaag gttaattaat gcatttcagc   10800
catcattttg ctggtcatgt ggaaatatag cttctttagg aattgtactt agagtaggag   10860
ccacatatta tactataaaa ccataacaaa aatattttaa gtttgttctc acttgttgtt   10920
gacctccaga gtaaaatatt taatactctg gaaagttatg ggtttcaaaa tttatttat    10980 ggcaagaaat agataattac agttctcata gagcacattt aaaataattt atttttatag   11040
ggcaaaaata ttgcctagga ctgaatgatt ttttttttt tacaaagatt gtaaagcaac    11100
gcctgcaaga gtgcccattt agcagttatt cttctggaat aattgtattt tggatgttgg   11160
agttcgcaca ttaaccatta gtacaagtac ccaatataac aatagatcat caggataata   11220
aatctgtcca tcttttagtt gtatgtcttt atatcaggat aaagagaatt gagtgaaatt   11280
tatctaaacc tagtcccaca atactttta caagagagca tgttaaagtg taaattaaat    11340
ttttattagc attctactct gtctttggaa gttttttttc cttatgaaat gcagccataa   11400
agtttaactt ccattaacaa agctgctcac agtaaaccta ttataataat agtttcccag   11460
tttgggcttc ctagtgagga gcaacctaac tcacacgaaa caaccccaac ttataatata   11520
ttgactgtta caaaactgag accagaaaat cccatcaaga tggtactgtt atcatttcca   11580
gactctcggg aagaacatta atcatctcag gcacttttag gatagactta ttgcagcctc   11640
cctgggaact ctgcttcaga acataattat ttttattaat gcagagttac ttttttattc   11700
caacaaaaat atctattgtt attatttaag tcttacagct ttatctgaga aattccaatt   11760
agcacccttc tcataataaa tattcaaaca catgaaaaat taccaaagtt gttctagtct   11820
tttaatgaca tattacatga tcctgcactc ttgtcacttt aaaaattatc ttttttattat   11880 atttctgatg attttttct tatatagttt tttaaaagga gcaggcaagc atagaagact    11940
aaaaaatgtt caaagaaaa attaaatcgc atgatctatc tatatgggac cttgtcattt    12000
ttagaaaaca ttcacctgct tcatcctttt gaatcttcat ataatccctc tgagatgggc   12060
atactataca agttgtctta tttaaagatt ggtaaattta agctcaaata atttattcag   12120
tggcaagcct cagaggcaga ctcggaacac aggtctaata tatattatat atatattata   12180
```

```
acatataata tatatattac atataataaa gttgtgtata ttatttacct atcaaaatat    12240
ttatatgtaa tatataaata tgttatatat catgtatgtg cctatttcat acatatatac    12300
acattcatgc aaaataaggt ttagcactcc ctccactgtc ctgtaataaa acatgcacag    12360
tgagaatagt catacacgag gcatatttgt cttcagttta aagtcattga tagtcagtgt    12420
cactaactaa agtaaaatag attggagcac caactttgtt ctgaagcctg tgccaggtat    12480
tatgagaaca aaaataaaaa tgttcctcac ccttggtgga tttagtcttt tgcagaaaaa    12540
aagatcctgt acatgtcaga aagttcaata gtaataatgg taatttataa ctataaatgg    12600
aagtcaccat ctcacaattt caccatctta acaattttgt taaactgccc tacaatatta    12660
caagatagta cataatgata cactagtaac atcaactagg aagtaccaag atccaccaaa    12720
aggctgaaaa atttaaatat ttaatgagtc catcaaccaa tctggccaga gaattcttta    12780
attaaaatgc ttcccaaatt ttactgagaa tcagcagcgt ttgaggagct agcctccacc    12840
cccagaggtt ctcactctat taggtctgaa gcaggtccca tggatttgca tttctaacaa    12900
gctcccaggt ggtgctgatg aggctgattc agaaccacac ttggagtaga cctaaaacag    12960
cagtgacctg tagggtcccc aagcagcagg ccaggacagc atgtgagtta cgtcctctgt    13020
ggagctctgc aacaaggcgt caagaggtca gagtctaagt ccccatcagc tctgcccttc    13080
tccaccagtg ctgctggtgc tgcatggaag aagagccca gagggattc tgagtttcag    13140 tctttactct tgctgacgca ccttggtcag gtcaattttc ctgtttgttc ctctaattca    13200
gcatctgtaa aatagccatg tgaactgcct tgtccatatc agagggtctt tttcagactc    13260
aaggaaaaaa acgtgaaagt gattagtgtc tgtcaagtag tatataaatg caagaagttg    13320 agttttttaaa ttgtcattag atataaatac ccatgtgcat gcatttagaa tgagtaaaga    13380
gggaacaagg agcgcaatca aaaactgcgt catttgctttt ttgaaaaata ctttctatgt    13440
aatgaaaagt gaaataaaat gttaattgag tccctctgac aacagcatca gacgttttgc    13500
agttcttgtg attagaaccc acctggccag cccttcttcc tcctaaagaa gagccttctt    13560
cttcttaaat gaaggttggc tcagaagaag caattaactc attcaacgtt ttgttacagt    13620
caatccacat ccaactttc cccaactcaa tctgctttaa gggaaggatg gtaagtggtg    13680
gcccaagatg gcaaccatca agcttagaga atctctagaa gcaggggtgt ccccagcaag    13740
tagacactga aaatatgaga gggctgataa gccagagata aaactcagta cttactttgc    13800
ttctagtcca tgtctacccc tttcttggca ccaccttgac actaccctct gagtccacct    13860
tcctgagatg gtacaaactc tgcttagaca aagcagccca tgtccaaagg tgttagggct    13920
cagtttaaag ctgccttcaa aagttaaaac agaagtgtaa agttctgtgc aattaaaaat    13980
aatcagcttg tcttggaact caaacgaatg taaaatccta tgaaaattaa aaagcagtac    14040
cacaagttac cccaaaagtc cttaggtcag taactgttcc tgttacaggt aagagagagc    14100
atggattaga ggtgggcgtg ggtatccagt ggacatggtt ttgaaccatg ctccactact    14160
actcactatc tgagaattct aaatttatt aatcatttct atattataat tttctcagtt    14220
atgaaatggg aaaacaatac ctaaatcaca tggttgttaa gtaagcaatt gattgttaag    14280
catttggtca tcaaaaatat taatccccctt ccctgattcc ctagataaat gatgaaaata    14340
ctaaataaaa ataataaaaa tttaaagtga acatctcaat tcttatactt tgttaatttc    14400
tacatgtatt acaaatctac tagaaattac ttggaattga ggaaatgatt actgcttaat    14460
aattctttgt ggtagaggga gagttggtat catatttatg agacagcagc caatatagta    14520
```

```
tatctcaaag gaaaaaatcc attctacata atgccagaat ttaatagtta agcatttat    14580
ctaggtcaca gcacaataag caagatggat aattaaaata aaagtatatt tctcttgcat    14640
atatttctca tttcatgttt ccctatcata ttttatatct taccttactt caaatacata    14700
tataccttca ataaaactga gccttcttgc ttacccagga agtttcatca ttcagtagaa    14760
ataaagatg actttagaaa tattaaaata caaaaatcta cactgaggtc ttttgaatgc     14820
aggaaaaaga attatatcac acacacacgt acacgcacgc atgcatacac acacacagaa    14880
cctctcgttc tttcttaaca tcttatcaat ccatcagttt cactcccact ccgtatcacc    14940
tgactgtgca caatatctca ttgccacctc ccagtcttct ccctgcctgg cacctcctg     15000
ctctcctgct tccactttaa acacccttcc ttcagctagg tcttttcttt cagggatcct    15060
cccgttgctt tctatctgg atcaatttag ccttcctctt ctccacccat tagtggataa     15120
gcacgacaaa gacactagag tcaaataata caaacagaat ataccttaga tgagtatggt    15180
gatgaaaagg atatggatac ttagagttta gcactattct ctcagccact caggaaagca    15240
acgcctttac aatcaatagt gtttcaggta ccaatcaata atctgttatt gctatttta    15300
aaatctataa ggtatcagta aaatgtaatt actagagcaa caaagatatc ttgtgaaatc    15360
aaattagtat tcatccagca actgagtaca aaggtttaag ggaggataac taccaatacc    15420
aaaacatttt aagcattttg ttttgcctcc taaatatcaa atcatgtaaa tgtgtggtac    15480
ataaattagg aattatattt atgacatagc tgcagacata ttaagagaaa tatgtgctta    15540
tatttacaag tatagtacag ttcttttttca tattagatac tgttgatgat aatctgcata    15600
taaaaatgct caatattttt tcacatttat aagccataaa atacagctaa taaaatgtgt    15660
ttctactttc tcataaacat ggaatagtga caaacaagga gctttatatg aaagcaccat    15720
tacaattaa actctcacaa ggtcataata tattgcacta agcaggagag ttcagcttat     15780
ttaaaaaaaa aataaactc taatgaggtt ctggaatgca gagccaaagc ataaagatgg     15840
aaataaaga attgcatgtc ttctgaactg acttggttga tgattttttt aaaaaaggtt     15900
ttgtgtcttc tgacttggtt gatgattttt taaaaaaacg ttttgtggta gaacaaataa    15960
ggtaaatgaa attcagtatt taggatgaaa agttttcta atttcaggaa caacattgaa    16020
gaaatattga actaagcagc tttgaaagaa tcagattcca tttgttgaaa ttttttctgag  16080
aatgaattt tttaagacag tgtacacagt tgcagtgtgt attggttatg gattgtggca    16140
agctatatta caacttaccc aagaaataag gaggctgggc gtggtggctc acacctgtaa   16200
tcccagcact ttgggtggcc gaggcgggcg gatcacgagg tcaggagatc gagaccatcc   16260
tggctaacac ggtgaaaccc cgtctctact aaaagtacaa aaaattagcc gggtgtggtg    16320
gcgggtgcct gtagtcccag ctactcggga ggctgaggca ggagaatggc gtgaatccgg   16380
gagggggagt ttgcagtgag ccgagattgt accactgcac tccagcctgg gcgacagagc   16440
gagactccgt ctcaaaaaaa aaaaaaaaa aaaaaaga aagaaagaaa gaaggaaaaa       16500
agtcacttga aaagaatact ggactttgtg tccagcttgc atagctgaaa agaataaaaa    16560
cctgtccact taaactcatt gcaaaagaa gatgtcactc ctacaaatag caaagagtca    16620
tgaaattatt ctatccagaa aagtatacat ttcatccctt tggataaatt ttagaagtga   16680
actatgaata catcgggtga ggatagccag ctaagaagtc aagaaggatt tctcaaattt    16740
gctgctcaga aagatcatac tctccacaaa acaaataata gcaggctttc caagtcaacc    16800
ttgaatccag ctttccttta tctttccttc ttgtgaactt tcactagttt actatctaac    16860
aatgaatttg acgatagcca cataccatct tatagcaata tttgttatca tatcccttgt    16920
```

```
tatttatcat tcacctgctc tgcttgagcc agctacaagt cacatgtccc acgcactttt    16980
tcctgtttga ttttttacag cactttgaga catgtctcat tattcctact tgacaggaaa    17040
gaagccatgg aaagttgagt gacttgctcc tgatcacaaa tgctggccaa ggaagagtcg    17100
agtttcaaat ctaatgatct ttccactgca ctctagattc ctcattttga actattttt     17160 tattttttgc actatagact tttttccaca ttttgaactg ttttttattt tttgcactat    17220
agacttttct cttatacccca actatattga tgacttcttt taggctagaa acttgtttca    17280
cttactttcc ctttcttcag attgctgcaa tattggccaa catgtattgg gtacttactg    17340
agtcaagtac tgtgattgtg ccaagtatct tataggagga ttatcatcct cattttaca     17400 ggtgagaaag gaaggaggt aaagtcacac acagccaaca aaaatggtag caccaggatt     17460
tgaaacaaat cagtctgacc caagttgact ttgttaacca ctgtatgcac agtcttctta    17520
gacatagtaa gagctctaat tgtgtttggt gatttgatta ttatgacaaa gtaagtaagg    17580
gaagcaggga gaattataag aaataaggct ccacaacact tggctatagc aaagccctt     17640 aaaacttcaa aaggtcaccc aaagaataaa gatcaggctg ggagcagtgg ctcacgcctg    17700
taatcccagc actttgggag gccgaggtgg gtggatcacc tgagttcagg agttcgagac    17760
cagcctggac aacatggtga aaccctgtct ctactaaaaa tacaaaaatt agctggatgt    17820
ggtggttgcc gcctgtaatc ccagctactt gggaggctga ggcagggaga tcgcttgaa     17880 cccaggaggt ggaggttgca gtgagccgag atcatgccac tgcactccag cctgggcaac    17940
aagagcaaaa aactctgact caaaaaaata aataaatcaa tcaataaaat aaagatcaat    18000
ttggagaaat taatgcttat taataagcaa tgtcttgcac agcacttcag tttctcaata    18060
cattacctaa ctcaatcctt acaacaacac cctatcccca ttttgtggat aaataaactc    18120
atgttcagaa ggttgaataa attatctaag gttaatagtt cctgacctag agctcaaatc    18180
ttcagtttct atcatattct tgcccttacc ctggggtagc taacattcac tcactagtat    18240
tggagctaaa ataagggaga gaacatataa atgaatacaa aggagacatt cacctgcctt    18300
ctctttctcc ttacatagag aaggttgatt atctgctatt gtgaagtttg cctttttgaag    18360 gatagaaatg agaagacttt cttaaatttt gcctctacgc caagaaatta gagtggtacc    18420
accagtagtt ccattttcaa actatcactg tagctaaagc tatgtggtaa gggccaagga    18480
aaagaagtat tcttgcactt caaaatgcac tgaaatacca gtcagtagca taatataaag    18540
gaatttagtg gagagaagag ttgacctcaa tctggctcca acatctcggc tcttaacccc    18600
taccctacac ttgttcttca tggggaagct aattgggcca ctggaagatt cagcagctac    18660
catttgcagc tgagggacag cccctccctg cttagcaacc aatggatatg catttatgga    18720
acacctgcta actgcgacac acactcctat gtatgaggga aaatacaaaa aatgttaaag    18780
gagatgcctt cccttgccct caggaaactt aagtatagtt gcaaagaaat gattagcagc    18840
aaacgaaacc atggagaagt aagggctaag gtctgtgaaa caagcctaga aaataaccctt    18900 gtccttgaaa aacacaaaaa gaaagaaaga aagaaaagaa actccaaggc ccttgtgaag    18960
gaaaccatta agtttgcttc acttctgtgt ttaggaagac acaaacccag tcttaatgaa    19020
cctcaaggcc acaactactg gagacattta ggaattgtca ccacattcta atgtatatat    19080
cctctgtttg gcccttccta ttaatatttt gtaaaatttt tgaagatatg agcaatgttt    19140
aaaaccatga atcccccttt ttttataagt aatatttagg ctgaataaac aagagaaaat    19200
aggacataaa ggggagccaa cgtgtgcctt catttataat gtattcccaa gttgtgagtt    19260
```

```
tggtttatca gcaatttatc atgccaaatt ccaagtcata tttatctatg cagatcaaac   19320
acttgattct attttttgcct taattttttt attgggtatg tttatgacca agtcatatgg   19380
tattttctgt gacagataaa atgcacaggt tattccaatc tggctcagcc agtcatagca   19440
acatgtagtc cttctcatgt cttaagaatg agtatcaaga attcaaaggg agttccagat   19500
ggcatccaaa aagcttacag tttatgcatc acttattcta acagtagaaa aagaatattt   19560
gaagccaaaa atagaccttg catgtagcat gtggaagagt agaaattgcc ctgatagtta   19620
aacaatttga aattcaagac attaatttct ttatgaagca tttgtcacat cataggtaat   19680 atttatgcc tatcatatat atacttatta tgaaatacaa agaaattatt cattctatct   19740
aagactttgt atcctttacc aatatctctc cattctccca cctccaccct agccctgga   19800 aaccacccctt ctactctctg cttctatgag ttctttttta gtgagatcat gcagtatttg   19860
tctttctgtt cctgtcttat ttcacttgac ataatgtcct tcaggcttat ccatgttgtc   19920
acaaatgaca gaattccctt cttaaggctg aatagtattc cattgtgtgt atgtagcaca   19980
ttttctttat taattcattt gttgatggat actcatattg attccatatc ttgggtcttg   20040
tgaataatga tgcagtgaac ataggagtgc agatatcttt ttgacatact gattccactt   20100
tgatgggata tatacccagt agtgggactg ctggatcatc tagtagtttt attttttttt   20160
attttttatt ttttttattt tgagacagag ccttgctatg tcgcccaggc tggagtacag   20220
tggtgccatc taggctcact gcaatctctg cctcctgggt tcaagcaatt ttcctgcctc   20280
agcctcctga gtagctggga ttacaggcac gcaccaccat gcccggctaa tttttgtatg   20340
tttagtagag acggggtttc accatgtctc gaactcctgt cttcaagtga tccgtccacc   20400
tcagactccc aaagtgctgc gattacaggt gtgagccacc acgcctggcc tagtagttct   20460 gttttttaatt ttttgaggag cctccatact gctttccata atggctctag gaatttacat   20520
tccaccagca gtgcacaagg attgcttttc tccacattct ggctaaccag tctcctgtct   20580
ttttgagaac agacatttca acacgtgtga gataatatct cattgtggtt ttgatttgca   20640
tttccctgat gattagtgat cttgtgcctt ttttcatata actgctggac attaatatgc   20700
cttcctttga gaactgtgta tacaggagaa aataatcact tctcagagga gctttcattt   20760
caaaatatcc gggaaaaaaa tagaaaaaat ggaaaattta tcctagagta agttgtcttt   20820 tatatttga ccctgtttgt gacataaact ggatgataca aaactggaat gcaaaggctt   20880
taggaggatt acttacttac ttgtatattg ctttaggttg tttgcagaaa attatactaa   20940
ttgaagttca ggctatgatg tgataaaatc tatgtcagga gatgagtcta catgcaaagt   21000
ttgaggaagt gacatttgag tttcaaaaca aaaaagcaat tttcaatgtc atatctaggt   21060
taacccaaaa gatttctttc accctattta gctgcctcta agatggatgc tgaggataat   21120
tacactgtag aacaatagga cgatgcttca cactcacctc acaggctctg ttattcccac   21180
atactgccag agatactcca aaataaaatc actgcaacat caggcagtta taaacctcaa   21240
cggtattatt ttctatttat atacagtata ttttatattt tacaagtata aaatagaata   21300
tatttattct attctctttg acacaaagtg accataagac atattactta agtatgacta   21360
gcaaagtcat ggggcttgtc attcaggagg aaactcttaa ctaactgttc agtttttgtt   21420
cactgcacca tttacataag ccaaactaat gcttcacact gtgcaaaaca atgcacagtg   21480
ttgtgaatga atggctaaaa taaaactcta atgagtgggg tttgaaaaat gcaactttag   21540
aaaactgttg agaaaatgtt gcacactgcg cattttacaa aatttcgttg aaggacactg   21600
gatattcttt ttaggattat ggagggaagc aaaatttggg ctcctacatg cagttttgt   21660
```

```
ggcctttgcc tgaaatagtc atctcccatt aattatttag atatcattca tttcctaaga    21720
caacatttag ggagactgcc ttaagtacaa tttgtacact acccagataa gaattctttt    21780
tggtgaaaca tcgataaata ttacttggca gtaacaccaa gttaaaatat ttgtttcaca    21840
gtcgacgtta ataactatta tagataaagt gaattttata agacatactc agatctaaaa    21900
cagcaatatg gagctcttca aatccattga aacttcatac cagcctacgg aagtagaggt    21960
ttttatgcaa actcttcaag aaatatgctc tgaactttta attccttaga ttgatagagg    22020
aattaaatca tgatataact aataggtttg tggtacaaat tgctgctgct taatctgact    22080
ctgtgtcttc ccagtgttct atatgaatta gatattccat tatctaaaga caatcaaccc    22140
catcccacgg tgatagctct aggactccct ttgagttcat taaatctgta ttctcagtct    22200
ccaaacttct ggttaattca aacagaaaag tcaactggcc catgaactaa aataaagtca    22260 tctgaattt tttttttattt tgcagtgtga taaaagtctc gcacttttta tttctgaaag    22320
tttctgcttt cactgagagc ataataggct atccaccctt atgcaatctt acatacaaag    22380
tcatagtcag gctaaattca aaaacacatg tgagatagaa gtcaacgttt attttctgga    22440
gaaaagccac acattacaac aaagtgaaca atgaagctgg catccttatc actggtgacc    22500
aaaacatttg tgactctgga cattggcccc acaaatgcga taaacattct gcataggaag    22560
tgagttttgc taattaaaaa tggatccaaa atactttcta ctcttcagcc aagaattaaa    22620
aagtaatagg gaggaattga aatcacttgg gtgctacatt gagccattct ggagaagcaa    22680
ttcagagaat gtcatggcag cctcaaattg ctgctcagga gcatcccagc ttagaagatt    22740
gcaggaaagg aagagcaaag tcattcttac atgagaactg tccttaacca gatgaataga    22800
ctctccattt tttaccctgg ctttgtctca tttaagtccc aaccaatcta gctatcattt    22860
taggttttac tacctgctag tatttaggag cttaggggga taaaaaaatc cctcaatact    22920
cagaattaga cttggtgata aaatcttga cacataaaca gaataaagcg ctttcattac    22980
tcctctaaac cacagtgtca tttggtctct atcaaggact gtaagaattt ctttcatcag    23040
gggaaagaaa aaaaggacaa gagcctgcaa gatgtagcgg aactctcatt aaacacagca    23100
ggagctttaa ctggaatcca gagtaaggtg aggtaccagg ttacaacaat ttactgcttt    23160
tattacaatt ttgatcacaa ggactgattc atgtcatcta gtttctttc cttgtcacta    23220 tcactggtgc taagaataca tcaaattgaa atttaagagc ctcatatgtt tctgtataac    23280
ccagtgatgg gttgtactgc tttgaccttc ttaaatgtcc ctttatttca tttgatatcc    23340
attcccatag aaaaactata atgctttggt tggtcaaaat attaatcttt caaaacctcc    23400
ctggcttaga aaaccaaatt tttgtagaga gagatgggta gaatctaatt ttattctaaa    23460
gcaattagca ttcatcatc acagcagaaa tatctagaat attacctcat gtcagtgatc    23520
ttctgatatg ttaaaaggg tattttaaaa tctgagttat ttcttttct ttttaaagtt    23580 acatcattaa ttcatactc atcaaccaaa atattttatg ctccaaattt gaaccgatat    23640
agtatgtaag aagtgttcaa aatgaaatta ttttggtcta tttttgtcttt gaagaagatc    23700 acagggatgg acctcccaaa aggattttta aatgggatta catatctgac ttttaaaaaa    23760
aattatctga ccttgagtta tagtgcccca agtaagcaa agttccaaac acacagtatc    23820
atcagaattg agttaaaatt atcaccaggg gcttaatttc tgaaattaaa aaggaaatgt    23880 tatttccttta tgaaaagaaa aggaaccaaa aatgaacttc aaggtagctg atttctgtct    23940
atgttaagac ttaggtaatg ggagaaaggg aaaaggaagg acagaattag gagaggagca    24000
```

```
gtgtttaaca attgcgggtg caagactcaa gttttttaga atccattagc agagaaccct    24060
atttctccca ttaactgctg tccttttaaa tcctggcacc agctctgagg actgcagggt    24120
ccatagctag tgccccactc tacccagttt aaagacacca ctgcctggaa atgacagggg    24180
ttttttcttt aaggaaagag gtgctttctg ccacgtatat ataaattggt aagcttcaaa    24240
taaagtgctt ttgtcctttc tgtctatcag aaactgtgca aatcgaattg ctgtaaaacc    24300
aagggcaaga gacatcaatc ctgcattcta tagcatctga ttttatcctt tatcccagg     24360 cacatttcaa aaggaaaaaa atgaggttgc atttaaattg agtatttggg acttgccagg    24420
aaaacctccc gctagactaa tatgattgca gggaaaacaa gagaaaggaa aagtggagag    24480
ggagtgtgct aacagatcct gggcctcgtc agcagagccg tcctgagcac aaggccatgg    24540
tcagacatct ggtcccgcga atgacgtttt ctttatggtc attaagaaca ccagtgtgtc    24600
gggacacaaa caagtattcc tttcagggat tatgacacat tttctcccaa agtagtatat    24660
taatgacatt tccagagcat tctttactat ctttttatatg tgatcaggaa gactaataca    24720
tatcactact tcttttacac acagcattag ccaaaactaa agtgtcaaat acaattttgc    24780
ctaggatgaa taaacagaag aaatttttat gatactgcac tatcaattcc aaattaaata    24840
acaacaaaat gataagtgtt aaaattcata ttaatgattg tcccacaca agccggaaaa     24900 aatctttcta agaagtcttt catgagttaa tcccatcttt caaagtgttc agtggctccg    24960
aattcagtta ctgtttccta tcagttcttc tttcattaag tctcttccct ttttttctc     25020 tttgcactat ttcccttagc cgggtacata atctgctgtg ctttattcat ttgtgtctta    25080
agtttgtttc ccgatgacat acctttccag caacgccatc tggggagttt gggcaactgt    25140
accacgttag gaggaaaccc ttcttcacag gagagtgtgc ctttgctgca gggaaggaat    25200
taggatttgc ttggactgtg gttgcagctg gcttttaagg atctccttag aatgcaagca    25260
actcatcaat gagaatctct gcaatggttg tcactgggta gagtcatgct atgtggggtc    25320
atagcctttg aaacaaataa cagtaaagat aaaaatgcta ttaaaggaat caccacccac    25380
agaggttaac tgggttttgt ccccagacca cctcgaacaa gaaagaacat ttttatcagt    25440
cattttctta gttttagctg ataaaacaaa gtaccataga ctaggtggct tataaacaac    25500
agaaatttat ttttcacagc tttggaaact ggaagtctga gatcaggccg ccagaatgat    25560
cagattctag ttagggccta cttttgcttt t gcagactgcc aacttctagc tgcattttca    25620
tgtggcaaaa ggagattgag ctagctctct ggtctcttct tataaggaca ctaatcccat    25680
tcatgaaggc ttcaccttca tcatctaatt actctccaaa gaccccacct ccaaatacta    25740
tcacattggg aattagattt caaatacaaa ttttgcgggg acacaaatat tcagtccata    25800
atagtaatga ttactcatta tacatagggc tctaaatgtg ctagcttctg atagttttta    25860
cactcacttc tctttattag cttgtcaagc ataattaggg cagtggcctt actgaaaatt    25920
attgaattta gtttcctaag gacagatatt gaggagtttt ttcttcacta aaaattcacg    25980
ttccgataca gctttcatct gttactactt tgtgagatga aaaatctttt attttatttt    26040
tatgtttgga ttgacccttc ttaataaagt cggcatgtaa tatgcttcat gtgtttctaa    26100
tatgtgctta attttgcaaa atgttttgca taccagaatg catttctctt ccaaaaaagg    26160
taccagccta caaaaccttg ctgttactgt tttcaattag ttcatggaat taaatgtatt    26220
aaatgtttta tgctctggca gaaattatga ttctcactta actccatata aatctggatc    26280
tgcctgggcc tttataagtg acacaatttc attaactgaa taaacaaatg atacaaagaa    26340 atttggtttta gccttctaaa attccaaagg cgttcaacaa aatatctcag aatggatgtt    26400
```

```
ccaggacttt tatggcacag gacaacatgt attgcttatt ttaagaaaat aagctaaata   26460
gtgaggggat tcttttagca gatcctcagg atgtgttagg ttgaatcata ggcaaatgat   26520
atttgatcat tgcacctgtt aacacattga acctcatcct aaaattgtag agctagaaga   26580
aagccttctg gcagttttta aatagattga tttactgcaa tttatccaga agcttcaccg   26640
ttgtcactgg ctacatgtga ctttggcctc tgtggggcta tatcctcatt tgtaaaattg   26700
gtggtgaggt aggtggacag ttgactaaat aatctcttag aataattcta gtatctgtgg   26760
atctaaagca tccaggggtt gaatatgttt ctttctggcc aagaaaagat gcacctgtca   26820
ataatgccca aactcatctt ctgagaatcc tctttcccaa gatacccact ctcccttggg   26880
ttatattata gtaatgatca gaagcccctg ccaagaagaa actgttaacc tgggaggtct   26940
atattttatt tcacagccat ctgtttatac tttctcacaa gttagtgcac agtataccca   27000
tcattttcta ccattttcct taatttatta attttactaa ttgcataatt aacaaaagta   27060
agaagatttt acctccttat ccccatctgg tagtttgcag atacttggcc tgatgacaac   27120
tgacagtgat gagatactca ccaagtttac cagggcagga ggcttcctag agaaaaaatg   27180
agaaaatgaa atggggaagg ggagtgaagg attgaggagg tgacaatctg gactcttgca   27240
actgcatggc aaggttggca cacaagctgg gttgcaacgg agggaaggag atccttatca   27300
gatgtaatca gagctcagat cgagggcttt ggtgtgtgta gaaagaggga gagacaaaga   27360
acttaaaaca gagctgccat ttgaccttgc aatcccatta cttggtgtat acccaaagga   27420
gaataaatca ttctattaaa aagacacatg tgcttgtatg ttcatggcag cactattcac   27480
aatagctaag acatggaatc aaactaggtg tccatctatg gcagattgga taagaaaat    27540 ggggtaaata taaagcatgc aatacaacat ggccataaga aaaatgaaa tcatgtcctt    27600 tgctgcaaca tggatgcagt tgggacccat aatcctaagt gaattaacac aggaacagaa   27660
aaccaaatac agcatgttct cacttataag tgggagctaa acactgagca cacatggaca   27720
taaatatgag aacaataaac actgtggact actagagggg ggaaggagag aggtttgtaa   27780
aactacctat caggtgctat gctcaatacc tgggtgatgg gatttacacc ccaaacatca   27840
gcatcattta atattcccat gtaaaaagac tgcacatata cccccttgtat ctaaaataaa   27900 acttgaaatt aaaaaaaaaa gaaagaaaga aagaggctgg aaatagaggc tcacacctgt   27960
aatcccagca ctttgggtgg ccaaggtggg tggattgctt gagcccggga attcaagacc   28020
agcctgagaa acctggtgaa actctgtctg tacaaaaaat acaaaaatta ccaggcatg    28080 gtggagcgca cctgtagtcc cagctaatgg ggaggctgag gggggaacat cacttgagcc   28140
caggaggtgg aggttgcagt gagctgggat cacaccactg cactacagcc tgggtaacag   28200
agcaactctg tctcaaagag agagaggaaa gaaaaaagaa aagatggaca gataagaaaa   28260
tgcacttgga gattaagaga agcagcaac ataggaccct ggataatgtg tttgcttaat    28320
aactatcctg atgagttatc tgactattcc caaatgagta cgtggcaatt caggctgaac   28380
catcagagta gccctccgga atcttactta tgtacaatag acctgcatgc acatttacta   28440
gaatgagcct ctctctctgg taatcatgtc tgcttccact aattccatct gtttcctctc   28500
tctccctcct atcctgctag atcttaattc cttcgacctt cctttgtttt tctaactccc   28560
tttctttctc ttgttattta acctgctata ctatgcaatt gatctcctct gcactaagga   28620
acatgcactt cagaattctg ttgacatctt gcattccttt atatttagtg aaagaatgca   28680
aaggagtcta cctggcaata ttcactctgc aggaggcaat aattattatt caaattaaag   28740
```

```
gaagcagtaa agagaaattc agaaaaaatg aaatatacta atcttcagct tttcatttca   28800
gcctacaagg aaaaaatgaa ggagctgtcc atgctgtcac tgatctgctc ttgcttttac   28860
ccggaacctc gcaacatcaa catctatact tacgatggtg agtaacctag gatagacata   28920
cccctgctag ctagatcatt tggaaaggtt gacatatatt tgtttcttac agctcctgat   28980
ataattacat caatattttg tagctctcac tattgacttg ccgtgtctag ctattatgtc   29040
caattgatta cctattgctg aaaacagttt gaatttggtg ctaataacaa cacatcaatg   29100
tctgttaaga aatgtggatg gattcttatt aacagccaca tccagcatat caacatccac   29160
aatatgtcta aggtctttct tgcaaataa tttaataggc taagccataa ttggagtaga    29220
tcataatttg taagaaaatg ctttatactt agaaaactca agagaaagaa tcaacaacca   29280
taattgtttt tgctttattg tagtctttat aaagtttcta tactttgtat atacatgtca   29340
accagctaat gataataata attggctcaa taaataaaac tgacttacga ctgaggccct   29400
agataaagag ggtctgaaaa gaaaagccta aagaattagc atggcaatta acatgattga   29460
ggtgcaactc tttaggtttg atttatcctg attcattttg cttactttgg ctctgccaca   29520
atccacatga tcttggtcaa atagatactt ggattctcta agtctcattt aactctagca   29580
tcttcctctt ggagttgttg tgaggtttaa acggtttaat gtaagtcaaa tatgcaaaac   29640
caagcctagc tcattatatc actctacaat gatagctatc attatcaaca tcatccttac   29700
ctaattcagt caatttaact aaaatatttt atacagttct atgtatccta gatatcccta   29760
aggcatattt tactaactct caggctcaca aatattttc ttttccatat atgtaaagaa    29820
agacattaat gacaaaacaa actgacctg tggcagttaa ccccttctgc acctttaaag    29880
cctattcaag gactcaaagg catttacctt ccaaagttat tctatcgtag cacaaaaatc   29940
ataaatgcta attaactgtt ccataaggaa atgtcctcca tgtgaaagga attctgtctc   30000
caaacaaaac attcattaga atgcagggcc aatgcctact ttgtacaaat tcattcggtc   30060
agcaaataaa ttagacagac ctttattatt tgctagatgt agctgtgaag aaggatccag   30120
ctatgtttct tatgagacta atgtcgaact atgggttgtc actgaggatc cagagttcca   30180
tagggcgtag tcctcacctt caaagaattc agggcttagt agaagagtct tacacaaatg   30240
actagaatgt agaacacaga gtggttagga caaaggagcc agggatggtt tttgctgggt   30300
tagggaatga aaaaagggga agaaaatatg tgaagttatg tgtgagctga ttcttgaaat   30360
aagctgtttt tatttgcctg cgttctctta taatccttt ccataggctt ccataatttt    30420
tattgagctg tatttaaagt tgaatagata attcaacatt tctcgtaaac tgtgcttcct   30480
aaaagagtcc gtagagaatt tcaaatttct gcagtcttta acttgacctg gtatttctat   30540
gttagataat aacgtgactt gtttattgca ggcaaacatt ataacaataa attattatta   30600
ttgtttacat ttgtaagcac taagtatatg gcttgtgctt tgcattcagc atcctttatc   30660
atttaatctt cacaaccacc ttagaaggaa ggtactcttt ttatttccat cttttaaatg   30720
aggaaataaa agcataaaga agttaattaa cttacctagt gtcacacagc tattaagagg   30780
ggcttactat ttggatgcaa atataggcag ttctaattcc agagcctcta atctaaggca   30840
tttaaaccc catcacctta tcaaataagc tgttttatt tgcccgtgtt ctcttataat     30900
ccttatccat aggtttccat aatttttata aaattgtatt taaaatttaa gtataatctt   30960
ggatgccatc aggaaaatga aaaacatttt tacatttgtg aaggaaaaag cccacatcat   31020
ttccaatata gttattgagt tagtattatc tagactatct attagcagct aaggatctga   31080
ggtcaaggcc tgccagcctg gcattttact tgaccacaac ctccatgtgc actaaccagg   31140
```

```
ctgctaaaag aacattaacg ggaacataac ctgctggctt ggttgccaca attttaaaaa   31200
gacgttaata aattagagag cacttagagg ttaggaaata atatggtggt aaagatctag   31260
aaacagtgtc attctggggc acttgaagat gtttagcctg ggggaacaac ttgaaatgga   31320
acataactgt tttcaaatac ttgaaaaatg gtggtgcacc acagagaatg gcctaatcat   31380
gggtagcttc agacttcaaa caaggatcag tgggctaaaa ccagagagat ggagtttggg   31440
actcaaagaa tgctcatctg aaattgaggg ctgaccagcg aggttctttt aaaaatcatt   31500
gcattttact aaattgtgag ttctgtaatt ataaatgtcc tagcaggtgc tagctgtcat   31560
cttttctatt ataaattata ctattttatg ttataatttg tattatacag cttaaaaca   31620 taagggtctg ataatctgct tatctttaat acataagcca ctgatagaaa ataagtggct   31680
aaccattctt cagttctttt tttaattgac aaaaattgta tatgtttgcg gtgtatggca   31740
tattttgaaa tatgtataca ttagagaatg gctaagtgaa gcaaattcac atatgcatta   31800
cctcacacac ctgtcattta tttgtgatga gaacaaaaaa tctactcttt cagtgatttt   31860
caagaataca gtacattgtt attaacaata gtcagcatgg tgtacaataa gtcttctgcg   31920
gccgggcgtg gtggctcacg cctataatcc cagcactttg ggaggccaag gctggcagat   31980
cacgaggtca ggagttcgag accagcctga ccaacatgct gaaaccttgc tctactaaa   32040 aatagaaaaa ttagctgagt gtggtggtaa gcgcctgtag tcccagctac tcaggaggct   32100
gaggcaggag aattgcttga acctgggagg cggaggttgc agtgagtcga atagtgcca   32160 ctgcactcca gcctggcaaa gagggaaac tccgtctcaa taataagtct cttgcatttg   32220
ttcttcctgt ttaactgaaa ttatgtattc tttgatcaac atctccccag tctccacccc   32280 taaccctgg taaccacaat tctactctgc ttccgtgagt tcaactttat gaatagtcca   32340
catgtaagtg agatcatgtg gtatttgtct ttctgtgcct agcttatttc acttagcata   32400
gtgtcctcca ggttcaccca tgttgtcaaa aatgacagga tttcccccaa ctttttttaag   32460 gctgaacagt attccatgtg tatgtgtata aattagatta gtagatgttg ccactccctc   32520
ctccaccaca gtggctctat ccctggctcc tggctccagc cgagtacact agaggaggat   32580
attctaaaca gcaacaacac aggagcaaag acattacaat ggggtgttgt cttattgccc   32640
ccattagact gtaagcatct tgaagacaag gacccccatc acagagtgat gttgtcatcc   32700
ctggagtggg cactgtgcat gattgatgac tggaagcaat gaacatacag aagggcaaaa   32760
cagaaatcag caggatgctt tgcatttcag cattgacttt gccaaatatg cccaactgtt   32820
cagggagtta cattggttct aacgaagctc ctgtgattcc taagcacagg aatggtgata   32880
atatatataa tggtgcatgc atatatacgc atatctagat aatgatatct cattatatgt   32940
gagaactgaa gaactccgtt atgtttctcg tctaaccaaa aagggcctac agctacgata   33000
atttccaaac aaataaatct gtgctacttg attttcatgc aaagctcata tttgttcaaa   33060
aggaaaataa agcttaattt aaaatcaatt taggctattt ttatctaagt atgcttaccg   33120
ttattcaact ccctgcagat attgtcaaat ttctcaatat ggtaaatatt tattctgtta   33180
aaatatatcc atagttacac taaagacaga gaggtcttat atgttctaaa caacatagag   33240
caaatgctca taaacagcat tttattccta tctcccggaa taacaacgct acttccaatt   33300
gctggaatct aaattattaa aataaaccca tgctgcaagc tttgtatgct taacattctc   33360
aaatgttcac ttttcagata tggaagtgaa gcaaatcaac aaacgtgcct ctggccaggc   33420
ttttgagctg atcttgaagc caccatctcc tatctcagaa gccccacgaa ctttagcttc   33480
```

```
tccaaagaag aaagacctgt ccctggagga gatccagaag aaactggagg ctgcagagga   33540
aagaagaaag gtaactttt ccataggttt tccttctctc tctccctccc ctgctcctcc    33600
ctctcacaca ctcgggcaca catgcacgca cacacacaca cacacacaca cacacacaca   33660
cacacacaca catacagaga gcaatgacag ctgaacctgt gccatgccaa catgtatagg   33720
ttttcagtag acacagagcc aggctagttg gggtaaaaac tgtaagatag atgctaattt   33780
taggctagcc aaaccagagc tctcagaaat ccaaagagct tcagtgctct agtgccctt    33840 cccgtatatt gaatccccctt attataaaag cctcccttcc ctagaccatc aggcagaagc   33900
actgtagaga aaacacagcc ctggcgaact ccagtggtgg ggaggggaag aagtgctgct   33960
tcctccctct caggatctgt gtcacccccct ttgtcaggcg tggttttcct tggaattaca   34020
aattaccaga tcttccctcc aagatctttc ctgcccaggg taagggccaa gagcttgccc   34080
ctttcctctt cagagtccca ctgcctgccc tggaagttgg tccttccaag atcaggacct   34140
tctctgagtt ctttgaatat gttctttatc ttttctaag acttgatggg gattttctc    34200 tttttgccat tggtccctgc ttatattaaa gagctttcct tttgccaaat ctttactttt   34260
ccataatcac atggctaaga agagccaagg gtattatttg agaacactta gaaatcctag   34320
ggactgtgta cacaaacaga agttgtttga atgtgtctgt tccaaccatg tggttatggt   34380
agttaatccc atcaaggtac tcacgatcat ccaaaaatgg aattctttta tgtaattcat   34440
ccccacattg tatttcccaa tatttttat gatataattt tagaatcagg taatcactaa   34500
gaacatgttc cctgcacagt tttatgatgt ttctctaaa aagtcagcca aaactttgga   34560
cacttctatg ttggataatt aaaaacagaa tgaagataat cctcctccta aagattgaat   34620
tctccaagag agaatgcagg acaaacacag atgtgctgtg tatagtatat gtgcatatat   34680
acatgcatat atgtacacaa atatgtgtat tatcaaataa tgaggctcaa acattagaaa   34740
tccttagatt aaattttcta aacaagaaaa cactaatctt tgtagttgaa aaaaatcct    34800 cctatgatat gtaatatgct gatctcaatt ttcacctaag agtgatgttc tccaaatgtc   34860
cgatgagcat gtcatatata tatatgaa ttttatata taaattaca atggtaattg      34920 gtatatagag atatctatat tatagatata tatagctatc tctatatatt acatatacca   34980
attatagata taaatataac aatggtaact ggtgtatatg tgatgtgtat atatgtatat   35040
gtataccata attatatatt aatattgtat atatgccata attatatatt aatattggta   35100
tatatacacc atgattatat attaatattg gtgtgtgtat gtgtgtgtgt atatatatat   35160
atatatataa aatactagtt atcattgttc tagatttaaa aaacaggaac ctgagctact   35220
aactcgacta tatatatata tatatataca ggaagttgct ttaaaacatt tttatcagct   35280
tttttattgt tatttttagc tttattctca tagtaaagct aaaataaatt attcaacatt   35340
atcaaaactt tgctgccagc agatgtaagc aatacctaaa acagtggaga gcatgttgca   35400
cccaaagcag tttaagctct gacccaagca ctggcatctt ataggcactg ggtagagata   35460
agagtcatag gtcgacatat attgagatgc tatgacttga ttagaatatg gagtcagtga   35520
ctgaggtgaa attaaaactc aaaccacaat tcaacatcct gatttaggat gttgctggtg   35580
tttctaggta ctacacttaa tttgaaagaa attattgagg ataaaaaaag aactgggatc   35640
aacaaaatta actaggtgtt cttataagag tccctgaggt tactaattaa tgaaactgat   35700
aaagctcctg caccctgaca gcaagaaatt atcaatgatt atacatttaa acaattgaat   35760
tgaactagaa actggccaca tggttaaaag acatttacaa atgtaatcat ccagtgttat   35820
gatgcccaga aaaaaaaaat tccttagaat gctttaaaag ccgtattcca tcacctttcc   35880
```

```
agttatttgt taaacatttt gtaatgcaaa aataaccata tagattatgc cctagtggtc   35940
gggttttatt tttagttttt tatggttttt ttttgttaat ggtagagttt taattaaaag   36000
aaaatacaac taattagcag aaagtgccaa ctttaaaaaa tcactaattg attttattct   36060
attgggttat actgacttaa ttagcactaa tttaaagaac tattaattat ctttaaagag   36120
tctttagcaa gtgcatatat ctcagtaatt atgttagtaa ggacatgcct ataaccaaaa   36180
cccaactcaa ctagttaaaa caaaaagcaa atatgtgact aaaaagtcta ggagtggcta   36240
cagcatcagg aacagctgga tccagggatc acagtattat cagaaaactt tctttcagtg   36300
cctgtcatct cttcctgcat ttaactggtt tcattatcaa gaaagtttaa tttcaatagt   36360
cagttccaaa ttattttct cacaacttag caactccagc agaaacagag cttcttttc   36420 ccaatagttt aacaaaagtc ccgaaattga gtctcaatgg cctggcctgg atcacaggcc   36480
caacccagaa ccaatcatta tggccaagag gatgtagtag tttgatatgc tagcctgaat   36540
cacatgccca ccactgacct gcaaggatt ttaggtaaga tccctggggt aagaattgtg   36600 gagggtagt tccccagaag aaaatcgagg tgttctcaca agaggaaggg gtaatggatc   36660
ttaaataaac aaaactatag atgtccacat tttctatcta taaatgttta gtgttactat   36720
aacaattaga ataattattt agttcataca ctattcaatt tgtatctccc ttctgttgcc   36780
ctgttgccgt tattttctta cagatagaat gaaaaatatt aatctaggca gctctgtgaa   36840
acagtactgt ccaaggaata taacgtgagc caggccgggt gtggtggctc atggctataa   36900
tcccagcact ttgggacgcc gaggcaggtg gatcacctga gatcaggagt tcaagaccag   36960
cctggccaac atggcaaaac cccatctcta ctaaaaatac aaaaattcgc agggcatagt   37020
ggcgagtgcc tgtaatccca gctactgggg aggctgaggc agaagaattg cttgaaccca   37080
ggaggtggag gttgcagtga accaagatgg taccattgca ctccagcctg gatgacagag   37140
caagactcca tctcaaaaaa aaaaagaaa gaaatgtaat gggagccata tgtgtatttt   37200
taaatgttct agaagccaca ttttttaaaa taaaagaaat atgaaatgaa ttttagtaaa   37260
atattcttca cccaatatat tcaaaacatt atttcaatat gcatgtaatc aatatagaag   37320
tattaatgag ctgtttcaca ttattttatt catactaagt gtttgaaatc cagtgtgtat   37380
tttacgttta caactcattt caattcatgt tagacatatt cctagtgcct agtagccaaa   37440
ggcagccagt agcacagata cggatattaa aacagaaaac acctagtgaa taatgggaa   37500 attttaggcc taagttttta aaatccatac cagataatta ttcagattca aatttacttt   37560 gtttttcat atatattctt taaaaattac attaatatgg gaactcagaa agttcaaaag   37620
aaatttccat tctatggttt tagtctttac attgtcagaa ctaatgcaag tgtgaagttt   37680
aggatgtact gtaagtaata ggatcttcta aatctcatgc cttcttcagc tacctactct   37740
gtttctattt cagttcctca ctgtggggag gggacttctc tgaacctagg tttcatctct   37800
cactctcgtt catggtaaac aggttttcct ttgtggcacc tagcacaatt agtaagtaat   37860
tagtatttac tggcatatta gtatatatat gcatatgtat ttatttaacc ctatgtcttc   37920
tactagatta taaactccat gaagatagaa cttgtctttt gtttaatagt gcttggcaat   37980
agttattact gtaacatttt ttttctttc ttattcaact cctgttagtc attgcctgag   38040
tactacaaat gttttaagt aaattaataa ataataactt tcagggccaa atgtgaaagc   38100
ggcaatatat agcttgtttt gattttttat tccaccctcc catcctaaaa caattatagt   38160
cactaagttt ccaaatgaca tctgaaattg cactaaggaa atcctagtct gggcaaaatc   38220
```

```
actcagtcaa cagatattta tcaagcactt actatttggc aggccctgtt ctagacacag    38280
gggatactca tcaaacttac attccagtgg gggagaaaga gctaataaat acatacacag    38340
catattagat gatgcaaaat tagcaggaca aagagaactg ggggtgtggg ggtgaaagaa    38400
gctaatatta tatgttatta ttactatata taataatata attattggat agtcaaaaaa    38460
aaacctcttg aataagacat ttgaaaagaa gcacaaaggt agcaagggag tagggcgggc    38520
agctcttctc tgggacctga acattcaaaa tgatgagagc agcaggtgcg gaggccctga    38580
aataggaatg tatgaggtgt gtttgagaaa taacatggag gccagcgtgg ctgaagctga    38640
gagcaggggg agagtggtag caactgaagt cagaggtcac aattaaggac tttgacttca    38700
catgaaatgg gagatcatga aggataataa agccatttca ctactttatg tgaatcacag    38760
catcttttta aagaagtatc cttttttaaa gggggagatg actagaaaaa taaatagtgt    38820
tagataaata gagaaaacag gaaaacattc tagactaaga cagtgattcc agaactaagg    38880
atccacagag gcgagaatgc agaaagtgta ggtttcagag cagtgggtag actaagggtt    38940
tggactagtg gatttggata gggagttgga gagtagcgag gtgggattag ggagggctgt    39000
gaatgccagg ttagtgtgca aactccatta tataagcagt aaggagtcac tacagacttt    39060
tcaaaaatac atacatgttc cacctggccc acgggttagc aacattttcg ttgccctgga    39120
cccatttcct tcccaataag ttacaggttt gtgaagattc tacctagcaa acatattact    39180
tttaaataac tattaataaa ttatcttacc atgattataa tcaaggaat ctgtaattgc     39240 taattatttc tgattattaa aagataagca gtattgcact aaattgacat aattctaact    39300
caaagtaaat atacagatag acatggctat agatgtgaaa tatgatttct gttagggctt    39360
tttaaattta aaaaaactta cgagttctcc tccctccccc tacccttaat accttgaagg    39420
cctctttgtg ggacttcagg gacccccttca gggaactatg acctaggctg tatttggggg    39480
gctttctggg tttatagctg gaaggctgcc acagaggcat cgccacttgg gctcagattc    39540
actttgtgtt caatgttttg gcaatgtccc cacctcccca ttccatctgt tgacactatt    39600
gcagcactga ccatctggtt actaggttgg aggatactcc ctcgggctcc tttgaaccag    39660
aattagtgct ccagtgatta gataatagaa gaagcttgtc ataaaaagaa taagcccttt    39720
ccctgctttt tctccattct ttgattatcg ctggtagtca gtgatgatca tctctatgag    39780
tctatatcaa tctcatcagg tcagtttgaa cctcatctct tgaaatcaaa gtttccataa    39840
tgcaactgac ccacaagggt gaaatgacat gaatgcttta accatccatt tatcatttat    39900
tcattcattc aaccaacatg tatttagcaa gaggcagcag agttagcata actatacatc    39960
ccagttggcc caggacaact ccagctaact ctcgttgttt tgataccatt attaattatt    40020
tctctttact ctcataagtg ttccactttg gacaatcaat tacatgagca tccttagcag    40080
ggcacagtgt ttaagggcat cttttaaaata ttgtctttaa gaacatgtgg ttaagagaat    40140
gtctgtgttc aaatcctggt tccaccactt aaaagctgtg tgacctcaag caagtgactt    40200
aatctccgta tgtcctcctt tgtcaatctg taaaatgaga ctagtaatag aacttatgga    40260
gttagtgtga gaattggaag gttactctac aataaagaca tataaccagc atggtaaaag    40320
ggttagcaat tactatgtga agaagcatcc agtttctgac ctcacagaga ttatctagca    40380
aactcatgat tttataaaga aaagaagttt ctcatcaaca gagactgaaa tgctaccata    40440
caatatacgt tgcttttttt ttttttttttt ttttgagacg gagtctcgct ctgccactca    40500
ggctcaggct ggagtgcagt gttgccacct tggctaattg caacctccac ctcccaggtt    40560
caagcaattc tcctgcctca gtctcccaag tagctgggat tataggcacc caccaccaca    40620
```

```
cccagctaat ttttatattt ttagtagaga caaggttttg tcatgttggc cagactggtc   40680
tcaaactcct gacctcaggt gatccaccca cctcagcctt ccgaagtgct ggcattacag   40740
gcatgagcca ccatgcccgg ccaatatttt taaatattat aaaatattct ttatcaaatt   40800
gcatagaaga aaagacagtt tgataggtaa tagatatata aataggtcag gccaactaaa   40860
agtgtcctga aaaattaat attgtgaaaa caaaaggatt ttaatgacat tgataaaatc    40920
tcaccctaaa agagattaaa ttaaaaatca ccctacttga accagttcag tgagatttca   40980
ttagcatgct ctcattactg gcataatcag cttcaaagtc actaagcctc tgaaaggaag   41040
atgtgttgct tattcttaat aaaatggcat aaaagtagat cattagtcac caaacatgat   41100
agacttacct tttccatttg ttggcatctc acattgtaga tggcaattaa aatggaatcc   41160
agggaaagag ggggtggttt gtatagcaat ggattatgaa acaaagtact ggattattca   41220
ccgcttgaca ttcaggaaac attctgctcc ttacagaata tggcacgtgg gccacagaat   41280
cttccgtgtg ctaccttctc ggtgaagaag agcaccccca gtttcttttt cctaggagct   41340
aaccacagta aacccattac acactttagc agaagggctc attctaaagg tcttaggatt   41400
ttaatcattt taaatttcct gttatgcttc aggctcttca acacaaagtg aatattgtac   41460
tctttggttt tacataatta tattcaattg tcatatttca acaggacatt atttgtgact   41520
ttagatgggt caataatgat tttcattgtc agcagtaaag tcaataatta cagacacatc   41580
acctacccta cttgtgtaaa agcattttt ggtactagga gatttagtgt ctgatcaacg    41640
gtcctggata gcaagtaata tatcccccaa ataatgaaaa gtgacaagaa aataaatatg   41700
tttacttcag aaataaatgg aaaattagtg ctatctaaaa tgtagtctta agtctcatct   41760
gtgtacataa agtaaaatga gttttatgta ctagttactc aaatttatct tccactccat   41820
ttgtatagta attaaactct tacactcagt aatatacaaa ttggtaatta acctctttgc   41880
aaaatgttaa agtgttccta aatgtacaat aagtctcctt tcctgtctca ttgttttcg    41940 cttcacgtac ctctcatgta attatttcaa tgattgagtt cagtgtgagg aggtttatgc   42000
ctagaaaagg tgctcaccaa taacgtgcct cagttcccat aatagcaaga tcgagaaggt   42060
tctttagtct cccggaacgt cacgttgaac atctcagttc tatattttgc cttgacattt   42120
gcattatatc agctgatcat tgtcttgccc taattttccc ttttaatatt ttagtgacct   42180
tctatgttag gtacaggtta tttagaagtg ttcctccaag gccagatact ttttccttga   42240
acaatttatt tttaacaact tttagcgatt ttctcacttc accaccctcc gtttcataag   42300
tccacgcaat cacaattcct ttctgctaat ctgcacagtc aagatataaa gtaagaatac   42360
ctatttgaac atgtagtgag aactttactt ctctgccaaa aatgaaggaa aatgctgcca   42420
cttttgtatg tcacatgttt tttattctac agcctcactc acttcatgtc atgttttagt   42480
gcagttttct ggactaactg cttatttct cattgattaa actgcctatt tgctcattgg     42540
aattagagcc aatttttttc cttgagggtc tgactagaag attaaactat gttcatgtga   42600
gaatcaattt ctacctaaga aatgagttag aggagttatg ggcagcaata tctatctgga   42660
tgctacactg tgaaaaagga agcgaggtta tgcctttcta ccccaatggg gtagcagaga   42720
cctcaggaac tgaggtagat gccccctgg ttattagcgc ccctgaataa tttgttcaaa    42780
aattgactgc tggacaggtg tcgtgttgca cgcctgtagt cccagctgtg caggaggctg   42840
aggcaagagg atctcttgag cccaggaatt tgaggctata gtaaactaag gtcacaccac   42900
tatactccag cctgagcaac aaagcaagac cctgtctcta aatttaaaaa aaatattga   42960
```

```
atgcttatga atagagacta atataggaag tcataagtat ttccttggga tagaatgctt   43020
tccaccataa ttgacttgac atcctgtatt tttgtatgtg tggacttaag ttttaaatat   43080
ttgaaacaca gacaattatt aagtcctgca aatgtgtgag ttaatagtgg atataacatt   43140
cccttccagg gtgtaagaaa aggtaccaca gaagtgagca gccctgaagc acagcctggc   43200
ctagtttggc aggtctctgt gagttagcag cagactcacg tgaccacact ctgtactgcc   43260
ttctgtttct gtttcacccc attaattgtg ctaaagaaat gcacttgaca cctatgctgt   43320
gtaatctcat ttagccccaa tagcaacaaa agtactaacc ccattaaatt gagtcatttc   43380
aaactgagcc aaatgttgca ctccagtaaa tggagtaggc attggttata atgggaattc   43440
tccattattc ataatggaaa ccacaggagt ttgttcatgc agatcaaatg tgtcccacca   43500
aggcaagaag tatggaaaag tggtgttgct gtattacctt gtaatttcaa agccttcccg   43560
tctgaatctt atttccctgc tgtttcctct tgactttggt tctttcacaa aggaaaatta   43620
agaacacaaa tataaacatt aagttaaaac acaactgaac aaagtgccaa acttaattgg   43680
agcatctgaa aatgaaacat taggcagttg cagtggcctc ttgataataa ttcacagtaa   43740
ctctctgtaa gctgatcctg tctgaagagc agcaggcaca aggcccctgg ccatgaagtc   43800
catctcaaag ggccaggctc agcaaagcag gatgcaaacc caggctttcc aaataccagg   43860
ttggggctca tgtcactgtg ccacaggagc ttctgtagaa aggctacttg aaaaagtgg   43920 ccattaaaaa tccaggtgga tcctatctag ggcagtgttg gaaacactga tctatgggag   43980
gaggagcagg aaggaattgt ttaaccactg agcagaaatg ttacattgct acctgccttt   44040
agcagctgtg gctgatgggt accagttgct aagaagagca ttacctaaca gtgtattaag   44100
atagaaaaat gattttaaag cacggcactt agagaatgtt gaagttttac tttgctttat   44160
tttgatttgt ttggtttgac tttgtctcct ggagcatcct ccatggattt ctgttcatta   44220
caagagaaac ctagggctct aacccaattc ctaattcttg acacattgc accccttgttt   44280 tgtgataatc cagccttctt ccttgagaag gtttgctgga ctggaggtta catgtattga   44340
attttctaaa atgaaggtgc aaagctgtct cctcttattt cttttgtggtg ctcacttcac   44400 tgtgagattt cctatcaata cagcccaagt cagtgggcat gcatgaggtg gagatgaggg   44460
agttaggaag gacttggact ctcatcaacc atcaggatcc ctgaatccac taactgttca   44520
taatcaaaga agtttgaaca aatacttcac acacatgaaa ttgccaaaat tttgcatttg   44580
agttgttata ccagtaagtc cagttgccat catctccttg tcacaagtgt cttaaatttt   44640
gcttttgata ataatgatta ccactcattc agtactaact tacttgatat tagacactgc   44700
attaaatacc ttgcaaacat tattttgttt gatcctgaca accatatgag ataggtacta   44760
ttcttatcca ttaccaaaaa aattaatttc atgaagactt ttcccagaga gagaaacttt   44820
aaatatttac acacacacct ctctccctgt aacaattccg tagtcctgat aacagcaaat   44880
aagcaaagtc tgtgtaggat gctttaccaa cagtcccacc tagaggcagg agagtgaacc   44940
agctagaaaa tattttattc atatttcttc cagaaaggct ccattggagt ttgaactcaa   45000
tttatgttat aattttctta ttattttttgt attggttttc ctgaaaccaa tacaaagtaa   45060
gaaagcattg gttccactaa aaatgtccta aaaccagcca agcacagtgg ctcacaccta   45120
taatcccagt actttgggag gccgaggcgg gtggatcact aagccagga gttcaagact   45180 agcctggcca acatgacgaa acccatctc tactaaaaat acaaaaatta gcagggtgtg   45240
gtagcacaca cctgtaatct cagctactca ggaagctgag acatgagaat cgcttgaacc   45300
tcagaggcag agattacagt gagcagagat cacgccactg tacttctgcc tgggtgacag   45360
```

```
agcgagactc tatctaaaaa aaaataaaca cataaatagt aaaatgtcct gaaaccatta    45420
tggggttaaa gcaagaggca gggctggttc ccaggatttt ctgtctaatc tccagtgagc    45480
cacagaccta ttcctgatca acttgagaat aaacacatca gtaaagatgt gtaaggctgt    45540
ctgactttcc catttctgta gaattttatt tgaagagaag tttctccttt ctccaggccc    45600
catattgttt atacaaaaag accttccag taaatgtcca caaccactac catcaactaa    45660
aatgttttcc cactaatgct ttcaatggta atcagtattt aacagggcac ttaggattat    45720
tttttgatca accattgttt agatattccc acttataatt actcctgtga aggattgcct    45780
cggggcatca gctgatcctg agaaattatc cagaagccat gagtgtgtaa taatttagtc    45840
ttaaacctaa ataggtcagt attgggtggg acttttctca gctgcataat ggggagaata    45900
aaaagaatat ggaaagaagt tacgtaacac atcctgggtc acaaacagag gtaagacttg    45960
aacacaggcc tgacatcaaa gcccatgcca gtatgactta caaaaggtag actggactac    46020
ctgcatttga gtcactagtg atgcttatca ctgggcctca ccaaagaacc ttggaatcag    46080
aatctttgga ggtagatgcc aggcacctgc attgttatca agtgctccag tgattaccat    46140
tcactgtaca gagccaaaca gactcctgat gctggaagaa aattacagtg ctcaaagtgc    46200
agggcagggt gtacatctgg atctaaatca ctgagcaacc acagggtttc aagagagggt    46260
caaaacaagg actttctgct ctctgtggcc aaggggacac taagtttgca ctgttctcag    46320
atctccaaag agactttggt gtatggggga tagggagggg ggaaggggt gtgaaataaa    46380 aggagaaagt gaatttgatt atttgattga tgaaaattga aaagcttatt gtagggccta    46440
gcctacagtt gatgaaaaaa caatggatca ggaagaagat cagaacttgt ctcagtcctc    46500
aactgttttc ctcaggcttt ggttgaatat tgccatcctg taattcatta tagcattttc    46560
tgttgcataa acgcttagca acaaagcctt tttttaaaaa aatttgtaac tcctcaatga    46620
ggattaaatg cttcttcttc taagacagtc cgaaatatac tcacagctga aaattcagct    46680
aaccgcattt cccaactagc cacattctat agaaaactct aagccatgca gatgagtaca    46740
gacttgacaa tagtgctcaa ggctgggagt actattcatc tgaaaagaat gctccctcca    46800
attggtgggc cgttattctg ctaggtttgt gtttggataa ttataagatg gctatgtttt    46860
tcttccccag tctcaggagg cccaggtgct gaaacaattg gcagagaaga gggaacacga    46920
gcgagaagtc cttcagaagg cttttgggga gaacaacaac ttcagcaaga tggcggagga    46980
aaagctgatc ctgaaaatgg aacaaattaa ggaaaaccgt gaggctaatc tagctgctat    47040
tattgaacgt ctgcaggaaa aggtaatctc agcagagtcc tgagcagatg gatatattca    47100
tatgcagcac agctgggtga acttccatat gcctgagcac agagacgaag tcaaaatttg    47160
ctgcaggtgt gaggacaact aactcccatg ggcagggtct cacagtgtag cattgagtta    47220
gcaggaggtg caacatggta gagaaatggg aatccatcat gaaagctgga atttgtcaa    47280 attttcccat ggtgagtgga ttcagggagg ctgattcatg cttttgaaat gtgtaagact    47340
tctatacaag cctcacgagg caatctgtag gaaaaatgtt acactggaaa tattaatgtc    47400
tatatattat attgatataa gtaaaataa catttgattt aatatttgtt taatatatga    47460
cattaaatat atatttaatt aaaatattaa attagaaaaa tatatttgcc agaaaaggcc    47520
agggtattta tgaacactgg taagcccatt ctagggtata atagcatcac atgggaccat    47580
agcaaagatt agctcatagg ggatgttttca tccagttctg gtatcctggt gcccttctct    47640
tcaacaacct aaacatatat tcattcccat gagtcaggag gagctgtgct ggagttcttc    47700
```

```
tgaaaaatgc tgtctttcac ttttgtactc tctatgctgt ctcccaccta tccctcaaa     47760 aaacctttcc tttgaaaata tacagtatag ctgtgagtag tttagctgtg tccgtttcca     47820
gaaattggaa taagcattga gaaatgggat gtttgagaaa gacgcctcaa tccttttctg     47880
agcagtcagt cacccttccc gccagtagca agtgcctttg tgtgataggc attggagatg     47940
cagagcaaaa caggagtgtg cctgtcatca gagccctgag agtttaatta gatgagcctc     48000
ctgttttcta tttctcagag tttcatgtct tctgttagag atggcccttc tcatctaagg     48060
ttcaaaaaac cttatcctga agttctgatg attctgtttt cattctcagt ctctgactgc     48120
aaatatccaa ctagaaacaa aggaaatcag gcatgaaaac ttttaaagat ataattgcat     48180
ggagatcttc atttgtgctc gtgaggaatt tttgaaagca ttgctgggga agggtgtgtg     48240
ggctctgatg cagcagtaag acactgaggc tctcagaggt ccgtggacga gtactgctga     48300
cttgggcaag aaccggaata gttacctgat gccttatccg aaacatgaaa gttcggatta     48360
aatttgtatt tataagctag tgttttata ctctcagaac aatgtcattg cgtttcaccc     48420
aagtgagtca agtcacgatt tggaagaggc aacagaattt ggctctctcc aggtgattta     48480
tggcggtata ggaacacatg ttttactcag atacagggga gcaaagttcc atttgctaaa     48540
gtttactccc ctgaccttca accagtcagt cttcctccat ctgccaccac tttgcacttc     48600
tccagagaac taaggatgtt cccgcttgac cagtgctcat aacatggaca gcagagggcc     48660
actgtgtgat ctctttgaga tcactgtgac tcaaccttct tctcacatcc taggccctaa     48720
aacaattaag tgaagttgct aggaacggta cctgctgatc ttattgcagc attctcaatt     48780
aggcctcaat gcaagattta tatcactggc agtcctggag catttttgtt tttcaaatta     48840
cacataccca aacacacggc atagcctcct ttttttgttg tttgtttttt tgagatagag     48900
tctcgctgtg tcgcccaggc tggagtgcag tggcacgatc tcagctcact gcaacctctg     48960
cctcctgggt tcaagtgatt ctcatgtctc agcctcccaa gtagctgaga ttacaggcgt     49020
ataccaccac gcccagctaa ttttttgtatt tttagtagag acagggtttt gccgtgttgg     49080
ccaagctggt ctcaaactcc tgacctcaag tgatccaccc acctcggcct cccgaagtgc     49140
tgggattaca ggtgtgagcc accgtgccca gccaggcat atccttcttg atttcaattg     49200
taaaatagtt caaaaatttt ccatattta tctaatattt ccagaagtgc tagcttttaa     49260
cggaccattt ttttcctctg tgtgttttt tctcttcacc tagcccagcc atgctcagct     49320
catttttgta ctctttccac tcccaaccaa atttagtgcc ctcccccata catgcataca     49380
tgtacatctg cacaccactt ttcctgcaaa taatcaaccc aaagagtgct taaaattcct     49440
gacatcaacc cacagaatct ccaaggatgg gacccagcat ccatacattt taaaaactct     49500
ccatatagtt ccaatatgca gccagatttg agaactagtg gttcgtagcc tgttctgatt     49560
taaatctcag ctctcagcag tctatcccac gtcacataat gcagcccaga gaaattctag     49620
gaccacattt ttttctggta tttcatagct aatgaggtgc ttttcaaatc taataggatc     49680
tttggccagt gtcagtcaag atcttttatc tcctcaataa aaaggaaata ccatatttac     49740
tttgatttga tgtatatcac ataggtggat ttaatacaaa attgtggttt acatattgtg     49800
aatgtgtata ctaaaactac tttgctttt cctaaaataa gacaaagttt tatattggaa     49860
gtaatattta gcattttgtt tgaatgaagt tactccatt aaattagaaa tttaaaagag     49920
ggtcagtaat aacagtaaag ccaaaaggca tgacactgcc aacgtaacat aagctgctct     49980
gaaatctacc atatcaaaag ataattatgc tgggcatggt ggctcacacc tgtaatccca     50040
gcactttggg aggccaaggc aagagaattg cttgaagcca ggagttcgag accagcctgg     50100
```

```
gaaatataat gataccttgc ctcaaacaaa aattcaaaaa ttagccagca gtggtggcac   50160
acttgtaaaa atgcctgtag tcatagctac ttcagaggct gagatgaaag gattgcttgg   50220
gccaaggagt tcgagactgc actccaacct gggaaatatt gtgccactgc actccaacct   50280
gggaaacaga acaagaccct gtctctaaaa taaaaagaaa aaaaagatg accacttctg    50340 aaatgacacc tatcaatgag ttaatcattc aatgaatatg tattgagtcc ctactatatg   50400
cttaggaacc tttgtaatat cattaccaac catgtctttc ccaatacaga caatacaaaa   50460
ttcagcaata aataatatag caccaacaat tagagaataa gacaacatgt agtatggtcc   50520
aatatagaca gtaaatacaa agacactgaa taatatcagt aaaagtaaat tcacatcaag   50580
gtcactacac catgcgccca cccttatgat agccctcact ggccctatca attaagcaag   50640
agacatgata caactctgtg caagcttttc cacaatctgc ctaccattca gcactcagtc   50700
gctcttccct tcaattaaga gaattgagca ttcaagcata ttttcaccat gatgcccata   50760
atggtatctt caatgtcact gactgataaa ttcccagaaa cccctcagag ccccagccat   50820
gttagctcaa agcctttagc taaaactgaa agcctaaagc aaaagcagcc ctggctgcac   50880
ttcggaatct actggacagc tctttaaggg attctgattt aatgtctgga atagggccaa   50940
gaaccttgta ttattttaaa ggctcactag taggctctaa tatttagccg tggttgagaa   51000
ccactgtgct aaatgtttct taaatatgct ttgtgatgtc atcataaatt atattttagt   51060 atttttttgtc tttgttgcat aagtgttctt tcttcctcca agaagaatg ttacactcat    51120 ttcttatttc agtttcctgt tttcatagca cctcatctta acactccagg ctattatata   51180
gaaaagaatc aaatgtggag aaggctgtgg gagaagggat gcctgtgcca caaaggcctg   51240
cattaggctg acctattgat gtcatatcca ggactcaaaa gactagtctg tggattatga   51300
ctggtgaagt tcaaaatgtt cttattctta gagtggtatg agaagtagaa agagagagaa   51360
acagagaagg ggaggagagg ggaagagagg aagatgagag aaaggaaaga gaggggaaa    51420 cacctgttct tgacatacag gaatgattca agacattttc ttcctcccct gatgtgtccc   51480
tttctcccct aacgcactat gcagcatcct gcagaaaatt caccacctga ccctttttaga   51540 aaccctgagt agtaggagcg ccaaatgacc caatcaagaa ttgcagtgag acagttagtt   51600
ttgaaaaatc agttaaagca tgtataatca ttttaacaac aatacatcta ttcactaaac   51660
atataatttt aatgtcaaat atttacgtgt aaacatattg accaatcttt cgatgtagtt   51720
gggcccaata ccttttccaa aaattgatca gttaatgggg gttctatggg ggtttctttt   51780
cttgccatta ttcacactta tgtcacatta gctatgattt gcagttttaa tttctttaaa   51840
attgagtagg gactaaagac atctccaaaa agcctggata tagacttttt acaacttttc   51900
catagctttt atagttgact cacccagtat ctactaaata cttcactttc tcacgtattt   51960
ccaaaggttt ctctccaccc tcacaatttt ccattaatgt agtacttaat taaattagat   52020 agttaaatttt tcaaatgtga attgctaaac aggtgtggaa ataccattgg ctataatcaa   52080
gcatataaca caaccatttg agaaggaaag tatgtggcaa tattagggaa gagcccttc    52140 ctctcaagca attcagcatt taggaaccat cagacagcag gacgatggag ggaacagaga   52200
gggttaacat ggcaagttac tgaagaggac ttctactgaa tcttgttgaa ttccccactt   52260
aatccagatt gtatcatatc ttctttctt tgtaattcta ccatatcatc ttagtcaatg    52320
ccaagacttc tgagctcata acatggtaac aaataccaaa ggagctttca gtatcgttta   52380
gaaaggagag aagcaagtaa cccagacaaa cttgacaact gctttcccct atccaaccat   52440
```

```
gaagtacagt acttaggaaa taaaagaaat tgcttcacta taattcatca tttcacttct   52500
aatatctaga aaatgtcaaa tgaaaatatt atagccatat tttagtggca atagtagcac   52560
ataatatgat gcaacttaaa atgataaaaa tattttcagg gaataagatt ctgtgattct   52620
ttccctaaga ggtaattttg ataatatgta cctgttttgt aaatgtcaat agtcttgggg   52680
atacaggtgg tgtttggtta catggaaaag ttccttagtg gtgatttctg agattttagt   52740
gcacccaata cccaagcagt gtacactgta cccaatatgt agtctttcat ccctcgcccc   52800
cactcccaac cttcccccac aagtctctaa agtccattat atcactctta tatctttgca   52860
tactcatagc ttagctccca cttatgagaa catatgatag ttagtgctca attcctgagt   52920
tacttcactt agaataatgg cctccagctc cacccaagtt gctgcaaaag acactattta   52980
gttccttttt atggctgagt agtattacat ggtgtatata taccacattt tatttatcca   53040
cttgttggtc aatggacact taacattagt tccatatctt tgtaatttca agttgtgctg   53100
ctataagcat gcatgagcct gtgtctttt catataatta cttcttttcc tttgggtaga   53160
tacccagcag tgggattgct ggatcaaatg atagttctac tttcagttct ttatgttttc   53220
cacagtggtc atactaattt acattcccat caacagtgta aagtgttccc ttttcatcac   53280
acccatgcca acacctattg ttttttgact ttttaattac ggccattctt gcaggagtaa   53340
ggtggtattt cattgtggtt ttaatttgca tttccctgat gttgacaata tttaactctt   53400
tagttataga ttccagctat tatcaattta cacctattgc attcttctca tcttttgttt   53460
tcttgtgatt ctgatgcaca aatatcattt gtgcaaccac ttactgttga acatgtctga   53520
tgaacactta ctattgaaca tgtctgatga atgaataatg aaataggaaa agggattaaa   53580
actagccttt attaattgtt tgctataggc cagacatttt tggatgtact atcacatttc   53640
atccaaacaa caacctaaaa gaaaatactg tgattatccc catttcacat ctaaggaacc   53700
tggtctttag gaagattaag tcatttggcc aagatcacaa gtagaccaca gagactagat   53760
ttgaatgcaa gtctgtttga ctccaaacct ttttactatc tgcccatgac ccctgatcac   53820
caacatctca atgtatgaac atgtgctttc ttagctcaca caactcactc ctgaccccct   53880
ttttatattg caagtgcata gtcattagta aaaagaagga ttttgatga tactgaccctc  53940 atcttgaatt taattaggct catatgacag aattccatag atggaattga catcctaggt   54000
catatagtcc aagtccttgt ttatatttga tacctagtga gattaaaggg acattaaaaa   54060
gtaaagaaag gaaagacctc atatttctta ccttccagta gagaaatctt tctatgaaat   54120
cagaggaaag aattagagga ccagaatttt tcctaaaatc aactttcata catctttttt   54180
catataaaag gcatagctgc atacaatgct aaaatattgt attacatttc ctttatattg   54240
atgggaggaa gggggtaaat tgcagaaaac attgtaaatt tagatatgct tgggcctctg   54300
acagtgccta gcaaatatca ggagatcaat aatgaaataa atattatcaa agagtagtct   54360
tcttgatgaa ccttctctga gtatcacaac tgctttagga acctctagat tcaaggtcta   54420
gtaattgcaa acagtgagct gataagaaaa acagactgta tgggaaatta catgcttcct   54480
gcatgactgc cttttgttct cccacatttt gatataaagt cacattaaca gttcatgagt   54540
aaatattcga taatgtgaac gtaaagtgtt caaataatag agtgactaaa atgcctgaaa   54600
acaaataatt tttaattaga aactcataat catttatttt ctcttttttcc acattatctc   54660 aagctcacaa attatattta ttcttttccta tggcaaaatc catttgttta acactaattt   54720
tgagtttaac aagaagtgta ctccaaagta gcctaataat actaattata atgtttcctg   54780
ctatgttatc agtttgaatt tatatgaatc tttagacttg aggcttcttt ttcctagcat   54840
```

```
agtgatggtc tgggctttt  ctcaattttt gccagagctc agctctcact aattagtttc  54900
tttctgcatg agaaaaagat tttgcttcat cttttttcctt ataatagcag aacaaaaaga  54960
agaatcagct gcatccatgc taatttcccc tgtgacattt ccaaacagga tttgatttct  55020
ctatgcatgc ctctttcctt ctcttcatgg tttttgaaca tatacaaaag ctcatttaaa  55080
ccaattaaat aaaattgttt ttaatctctt tctctagagt caacttcctg cttactccaa  55140
ctctgtatct ttgaaggaag tatagggtgg tctatgcctt ttttctccca gaatctacac  55200
ttgaaaagac acattttttcc atgcaactat aaaatgttct cctcactcaa cattgaaatt  55260
gtatagcagt gattaagaga gtgagctgta gagccaggtt ccctgggttt aaatcccact  55320
tgttagtatc atgaagatgg gcaagttact tacccttcct gtgtttcagt ttcttcatct  55380
gcaaaatggg gacaataata gaatgtccac tataagatta ttgtgaggat taagggaatt  55440
aatacaggta aaacgtgtac tgatgcaggt ctggtacaca ttaagtgcct aataaatatt  55500
cagtattatg atataaagaa ccctataagt gtagactcct tgagattaat agagtttaac  55560
gataagtttt actttatagc tggtcaagtt tatttcttct gaactaaaag aatctataga  55620
gtctcaattt ctggagcttc agagggaagg agagaagcaa tgtaagcaac attctacaga  55680
aatataaata atactactaa taattagcat cttaaaattt caattcaatg aacatttatt  55740
tagcgcctat gatatatgca agacagtttg attttagtca tctgatgtat agccacatac  55800
taaaaaatac tgattttagt catctgatgt atagccacat actaaaaaat acttcctcca  55860
tcagttccct cctcaggaag ttcagttccc aatcccaggc tagtaccttg gttccttatg  55920
taaataaaca tccaccaatt acatgctatc tgcaaagcac tctgctaggc cctgcaaatg  55980
gaaaaaaaaa tgataaaaca tagtccaggc cctcaatgag cttacagtca aatataaatag  56040
aggagacaag aacagagagg ctcataatac aactagaata aaatgactgc cgaataaaag  56100
gaaagattta tgcaggtgtt caaatggaaa gtgagataag tttgcaggtt agtctttgca  56160
gtctcataaa aatctttatg gagaaaagga caatggtcat agggcttaaa gagtaagttt  56220
ataatcctga ccagtggaga tgaaagacta gcattgaaaa ttgcatgaca agacaattcc  56280
attaaactga aacatcaagt gtgtgtagga aaagatgggg gttatgactg gaaacgtcac  56340
ttggactgca attatgaagg gccttgacaa acaggtcaag agtttaagaa gcagtataga  56400
aagtcttcgt cctggatcta gccctcccag agtgtccatc aggattataa agtccttaaa  56460
atattagtca aaaggaacga catcattaga aatgatagag aaacaataat gtgatgtttt  56520
attacctttc tctggattta tactctgatc ctaatattca aaactatctt aataacatga  56580
acttttggtc atagttttaa acaaaaacag tgttaaatat attttttaaa acacagtaag  56640
tcttgtaaga tcttttctaa catgacattt tgcagggccc atatttttcct tctgaaatgg  56700
gaaaaattca taaaagtaga caccaaactg ggttacttct agtcaagcgc atggtacgca  56760
aaggaccaga caaaagggc ctgtgacatt tcttcttcct tttgtgtttt ttaggagagg  56820
catgctgcgg aggtgcgcag gaacaaggaa ctccaggttg aactgtctgg ctgaagcaag  56880
ggagggtctg gcacgcccca ccaatagtaa atcccctgc ctatattata atggatcatg  56940
cgatatcagg atgggaatg tatgcacatgg tttaaaaaga actcattata aaaaaaaaaa  57000
aacaaaaaaa atcaaaaatt aaaaaaaatc aatgcggtct cttttgcagaa tgttttgctt  57060
gatgtttaaa aaatacccttg gatcttattt tgtaaatact tacatttttg ttaaaaaata  57120
caagtattgc attatgcaag ttatttcata atcttacatg tcctgtaaca ggcttttgat  57180
```

```
gttgtgtctt tccactcaaa tgaatttgct aggtctgttc tttttgaagc tccccatgtc   57240
taactccatt ccaaaagaaa aatgaggtca gtagacagtc tatggtgcta gaaacccacc   57300
attgcctaat gacctagaag gctttgttgt ctctgagctt gactaagacc ataccttagat  57360 cacaggtatt atgactccac atgaaccttc acatttgttc gctcataatc tacttactgc   57420
ctaaaaacta caaaaccagg ctaagaaata ccaccagtca tagcatttac ttctgcttct   57480
cctggattat gtgctacaaa tgtgctttgg ctttagaaag ggatggatga gaagacagac   57540
ctgagaccaa tctgggtaga agcaaaaagt tgaacctttt aaagtgctga cacaaatcc    57600 aaattcgaat ggttcaagca gccgtgaaat cgctcttcat aaagtgggct taattctcta   57660
gtttaagttc ttttgatgga atgaattaat taatgtgtca ggtggcttat ttgtggatgc   57720
catgattgat gatgttcatt ttaagctctt acctatagta caagtacatg atgctactga   57780 atattttttcc acttggaaac tgtgagctgg ttgttgcatt aaaacacaca tacaaacaaa  57840
atcaaaaaca ctgcggactt tcactcaagc tggtctttct tccccagtgt aaggcaatcc   57900
tgcctactaa caacaccaac aacaaaacac tccatctgtg aagctgacgc agttaagggg   57960
gctaggcagg gcatttgtgc caactaagaa tcaccagata cccaccataa gtacctatcg   58020
cagttttgaa gtcgtttctc cccaactccc aactcctgaa ggttgctgcc tgcatattta   58080
ctcttcatta gtgctatttt cctgtatgtc attgtgagca agctgtgatt aataaagaat   58140
tggagttctg tgaactaata aaggtttggt ctgttctctt gcctcttcat gtgtctgacc   58200
ctggagttca gattttaaaa gggcagccac tgaattagac aatctcacaa gcaaagagat   58260
aataaggaga gtttgaagga aaccagtgcc ctgctgagtc atttccctt gggaacagca    58320 ggccgcatct cttttctctt gccctctgat gggccaacac tgtgggagag gtcttcaatc   58380
tgctcccttt aaaaacatac aggactgaac aagataccac aaaatgcaga ctgataattc   58440
tgaggaagtg agcccttttc aaaacattga aggttcctgg cattatctca agttctcccc   58500
tgtggcccac agaacgcctc ccccagccta ggccgtctgt taagatgtga tccctgacgt   58560
actgctgaat tttgtactgc caataaacac actgcacaca tgggcgcagc agggtcctgt   58620
cagtgaccca aatggatctt acaggaccaa aggaaccaca tccagtttta gcagaaaatc   58680
ataaataatt gaaaccacac agatttgtga ataagtacag tgggctatgg tccataggag   58740
ctctaacaag ccaagtttag ggttgcggcc acctggtctc tattttgaat atcctttaat   58800
atttgtggga atctaatact gctacaaaca atgcctgagc ttgatgtgaa acacatgagc   58860
ttccaatgag catgaaatga gttgtctctt catactggtt ttctatagct tagtttggaa   58920
aacattaccc gaattactca ttgggtcaga ccctatgata agccctggaa acatgaacat   58980
gaatgaccac aagaagctca taatccagta gcttatttgg gccccaaaac agcaaacatg   59040
atatgttggt cagccctctg cagcatattt ggggaaaatg gatcatttct aagaagtttc   59100
tgaaatatta gaaatatttg acaaacttct catagtactt tgtatgagaa ctgaaactgc   59160
tgaccagtcc agctgcctaa tctcaaagat gaagaagcag gccgggcacg gtggctcatg   59220
cctgtaatcc caacactttg ggaggccagg gcaggcagat cacttgaagg gaggagttcg   59280
agaccagcct gggaacaag gtgaaatatc ttttctacaa aaaaaaatac aaaaagtagc    59340
caggcatgct ggggagtaac tgtagtctca gctacttgaa aggatgagat aggagaatga   59400
cctgagcctg gggagatcaa ggctgcagtg agctgagatc acccgctgc actccagcct    59460 gggtgacaga acgagaccat gtctcaaaaa aaaaaaaaa aaaaaaaagc gaaaaagcag    59520
aggagggaaa ggtgagtggt tggctccaga ccacagtgcc cacatctcat gacttcttct   59580
```

-continued

```
tcccttattt gaggtcctca gaagaacatc tccaagttgg gtgcagcata tactgcttgg    59640
gtgatgggtg taccaaactc tcacaaataa ccacgaaagt acttactcat gtaaccaaat    59700
accacctgtt tcccaaaaac ctatagaaat aaaaaagcaa aaaaaaattt aaaagaaaaa    59760
taaataaata aaagagcata attcacaatg ggggaaaaa aagaacacct ccaaacctgc    59820
cagaccagtg aggccagagg gcctcaaatg tcagtgtgct tccaagttat gtgaacggct    59880
tgttaaaaag agatttctga gtcctgcctc cagagctttg gattcctgag gtctctggaa    59940
gcctgaaaat gtgcatttct aacatattcc cagaagatgc taatactgct tgtctgcagc    60000
cctcacttga gaagccctgc tgtcaacaat gcaactgatc caggtgtgtg gattctctgt    60060
ggctgccaca ctgagggaat ctgtttcaat cagggcatgt tccattggag gcagggcaag    60120
aagagaaatg cattcactct tattcaaaaa agttcggggg tgggaggatg cagagaaatc    60180
cagaaaaaag caagataaac agctgtgcct tgcaggataa taaaacaatg gaagcaatca    60240
atcgtgcagc caggggctgg gatagagcta aggtggaatc agagtaccaa tgactcggca    60300
tctctcacac aacatgattt cagtaaggat caaaaatctg aagacgctcc ccaccctta    60360 atagatgaac tgagtgcttt ttgcaaggat ttgccattct gtgaattacc cagtttgtta    60420
gcctggttcc agttacagat ttttgtttg tttgtttgtt tgttttacgg agtcttggct    60480
tcttcagtac tgtgtttaaa ttgcttaaat gtctttgaaa tgttctgtga aaattcacaa    60540
agttccatta gtttgatgat tcaccctcct ccctatctc tcctacaccc aaaaatgtat    60600
ggaacaactg aatgttgaca aaggtcattc tcttttctag caagagtctc gcctttgtgc    60660
tcttcatcag ccttcacaac acctgagagg agaaaacaat ggggtaaaa gtgctaatag    60720 gcgtattgtg gcccatctac cctcctccta ctgagggaga ggatgaaaag ggggagacgt    60780
gacttctgtg gctttagcag ccaaataaca catcatctct ctcctcccag ccctggaca    60840 agacatcctt gacgtctaat caggcagttt gctgaaactg ctaaggcaag cacagagccc    60900
agaacaaagc taaggccccc aagctccccc acattacctg agtcgtcttg gattcctcac    60960
tgtcccccac cacccacctc cagttgaata tcaaatggtg                          61000
```

<210> SEQ ID NO 2
<211> LENGTH: 341
<212> TYPE: DNA
<213> ORGANISM: Homo sapiens

<400> SEQUENCE: 2

```
ttccgaactc atatacctgg ggattttatt actctgggaa ttatgtgttc tgccccatca      60
ctctctctta attggatttt taaaattata ttcatattgc aggactcggc agaagacctt     120
cgagagaaag gtagaaaata agaatttggc tctctgtgtg agcatgtgtg cgtgtgtgcg     180
agagagagag acagacagcc tgcctaagaa gaaatgaatg tgaatgcggc ttgtggcaca     240
gttgacaagg atgataaatc aataatgcaa gcttactatc atttatgaat agcaatactg     300
aagaaattaa aacaaaagat tgctgtctca atatatctta t                         341
```

<210> SEQ ID NO 3
<211> LENGTH: 21
<212> TYPE: DNA
<213> ORGANISM: Artificial sequence
<220> FEATURE:
<223> OTHER INFORMATION: Primer

<400> SEQUENCE: 3
ccacgaactt tagcttctcc a                                                 21

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
gccaattgtt tcagcacctg                                                   20

<210> SEQ ID NO 5
<211> LENGTH: 26
<212> TYPE: DNA
<213> ORGANISM: Artificial sequence
<220> FEATURE:
<223> OTHER INFORMATION: Probe

<400> SEQUENCE: 5
actttcttct ttcctctgca gcctcc                                            26

<210> SEQ ID NO 6
<211> LENGTH: 21
<212> TYPE: DNA
<213> ORGANISM: Artificial sequence
<220> FEATURE:
<223> OTHER INFORMATION: Primer

<400> SEQUENCE: 6
aaggcaatcc tgcctactaa c                                                 21

<210> SEQ ID NO 7
<211> LENGTH: 23
<212> TYPE: DNA
<213> ORGANISM: Artificial sequence
<220> FEATURE:
<223> OTHER INFORMATION: Primer

<400> SEQUENCE: 7
ggtgggtatc tggtgattct tag                                               23

<210> SEQ ID NO 8
<211> LENGTH: 24
<212> TYPE: DNA
<213> ORGANISM: Artificial sequence
<220> FEATURE:
<223> OTHER INFORMATION: Probe

<400> SEQUENCE: 8
tccatctgtg aagctgacgc agtt                                              24

<210> SEQ ID NO 9

<400> SEQUENCE: 9

000

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
aataaaatcc ccaggtat                                                 18

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 11
gagtaataaa atccccag                                                 18

<210> SEQ ID NO 12
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 12
cccagagtaa taaaatcc                                                 18

<210> SEQ ID NO 13
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 13
aattcccaga gtaataaa                                                 18

<210> SEQ ID NO 14
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 14
acataattcc cagagtaa                                                 18

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
gaacacataa ttcccaga                                                 18

<210> SEQ ID NO 16
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 16
ggcagaacac ataattcc                                                 18

<210> SEQ ID NO 17
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 17
atggggcaga acacataa                                                  18

<210> SEQ ID NO 18
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 18
agtgatgggg cagaacac                                                  18

<210> SEQ ID NO 19
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 19
agagagtgat ggggcaga                                                  18

<210> SEQ ID NO 20
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 20
taagagagag tgatgggg                                                  18

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 21
caattaagag agagtgat                                                  18

<210> SEQ ID NO 22
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 22
aatccaatta agagagag                                                  18

<210> SEQ ID NO 23
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 23
taaaaatcca attaagag                                                  18
```

```
<210> SEQ ID NO 24
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 24
attttaaaaa tccaatta                                                 18

<210> SEQ ID NO 25
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 25
tataatttta aaaatcca                                                 18

<210> SEQ ID NO 26
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 26
tgaatataat tttaaaaa                                                 18

<210> SEQ ID NO 27
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 27
aatatgaata taatttta                                                 18

<210> SEQ ID NO 28
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 28
ctgcaatatg aatataat                                                 18

<210> SEQ ID NO 29
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 29
agtcctgcaa tatgaata                                                 18

<210> SEQ ID NO 30
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 30
gccgagtcct gcaatatg                                                 18

<210> SEQ ID NO 31
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 31
ttctgccgag tcctgcaa                                                 18

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 32
ggtcttctgc cgagtcct                                                 18

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
cgaaggtctt ctgccgag                                                 18

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 34
ctctcgaagg tcttctgc                                                 18

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
ctttctctcg aaggtctt                                                 18

<210> SEQ ID NO 36
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 36
ctacctttct ctcgaagg                                                 18

<210> SEQ ID NO 37
```

-continued

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 37
ttttctacct ttctctcg                                                 18

<210> SEQ ID NO 38
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 38
cttattttct acctttct                                                 18

<210> SEQ ID NO 39
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 39
aattcttatt ttctacct                                                 18

<210> SEQ ID NO 40
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 40
gccaaattct tattttct                                                 18

<210> SEQ ID NO 41
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 41
gagagccaaa ttcttatt                                                 18

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 42
cacagagagc caaattct                                                 18

<210> SEQ ID NO 43
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 43
```

-continued ctcacacaga gagccaaa                                               18

<210> SEQ ID NO 44
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 44
catgctcaca cagagagc                                               18

<210> SEQ ID NO 45
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 45
cacacatgct cacacaga                                               18

<210> SEQ ID NO 46
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 46
cacgcacaca tgctcaca                                               18

<210> SEQ ID NO 47
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 47
cacacacgca cacatgct                                               18

<210> SEQ ID NO 48
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 48
ctcgcacaca cgcacaca                                               18

<210> SEQ ID NO 49
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 49
ctctctcgca cacacgca                                               18

<210> SEQ ID NO 50
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 50
ctctctctct cgcacaca                                                 18

<210> SEQ ID NO 51
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 51
ctgtctctct ctctcgca                                                 18

<210> SEQ ID NO 52
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 52
ctgtctgtct ctctctct                                                 18

<210> SEQ ID NO 53
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 53
caggctgtct gtctctct                                                 18

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54
taggcaggct gtctgtct                                                 18

<210> SEQ ID NO 55
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 55
ttcttaggca ggctgtct                                                 18

<210> SEQ ID NO 56
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 56
tttcttctta ggcaggct                                                 18
```

<210> SEQ ID NO 57
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 57
ttcatttctt cttaggca                                                18

<210> SEQ ID NO 58
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 58
cacattcatt tcttctta                                                18

<210> SEQ ID NO 59
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 59
cattcacatt catttctt                                                18

<210> SEQ ID NO 60
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 60
gccgcattca cattcatt                                                18

<210> SEQ ID NO 61
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 61
acaagccgca ttcacatt                                                18

<210> SEQ ID NO 62
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 62
tgccacaagc cgcattca                                                18

<210> SEQ ID NO 63
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 63
actgtgccac aagccgca                                                 18

<210> SEQ ID NO 64
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 64
gtcaactgtg ccacaagc                                                 18

<210> SEQ ID NO 65
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 65
ccttgtcaac tgtgccac                                                 18

<210> SEQ ID NO 66
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 66
tcatccttgt caactgtg                                                 18

<210> SEQ ID NO 67
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 67
tttatcatcc ttgtcaac                                                 18

<210> SEQ ID NO 68
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 68
ttgatttatc atccttgt                                                 18

<210> SEQ ID NO 69
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 69
attattgatt tatcatcc                                                 18

-continued

```
<210> SEQ ID NO 70
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 70
ttgcattatt gatttatc                                                 18

<210> SEQ ID NO 71
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 71
aagcttgcat tattgatt                                                 18

<210> SEQ ID NO 72
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 72
tagtaagctt gcattatt                                                 18

<210> SEQ ID NO 73
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 73
atgatagtaa gcttgcat                                                 18

<210> SEQ ID NO 74
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 74
ataaatgata gtaagctt                                                 18

<210> SEQ ID NO 75
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 75
attcataaat gatagtaa                                                 18

<210> SEQ ID NO 76
<211> LENGTH: 18
<212> TYPE: DNA
<213> ORGANISM: Artificial sequence
<220> FEATURE:
<223> OTHER INFORMATION: Synthetic oligonucleotide
```

<400> SEQUENCE: 76
tgctattcat aaatgata                                                18

<210> SEQ ID NO 77
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 77
gtattgctat tcataaat                                                18

<210> SEQ ID NO 78
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 78
ttcagtattg ctattcat                                                18

<210> SEQ ID NO 79
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 79
tttcttcagt attgctat                                                18

<210> SEQ ID NO 80
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 80
ttaatttctt cagtattg                                                18

<210> SEQ ID NO 81
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 81
tgttttaatt tcttcagt                                                18

<210> SEQ ID NO 82
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 82
cttttgtttt aatttctt                                                18

<210> SEQ ID NO 83
<211> LENGTH: 18

```
<212> TYPE: DNA
<213> ORGANISM: Artificial sequence
<220> FEATURE:
<223> OTHER INFORMATION: Synthetic oligonucleotide

<400> SEQUENCE: 83
caatcttttg ttttaatt                                                 18

<210> SEQ ID NO 84
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 84
acagcaatct tttgtttt                                                 18

<210> SEQ ID NO 85
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 85
tgagacagca atcttttg                                                 18

<210> SEQ ID NO 86
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 86
atattgagac agcaatct                                                 18

<210> SEQ ID NO 87
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 87
agatatattg agacagca                                                 18

<210> SEQ ID NO 88
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 88
taataaaatc cccaggta                                                 18

<210> SEQ ID NO 89
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 89
```

| | | |
|---|---|---|
| agagtaataa aatcccca | | 18 |

<210> SEQ ID NO 90
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 90

| | | |
|---|---|---|
| tcccagagta ataaaatc | | 18 |

<210> SEQ ID NO 91
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 91

| | | |
|---|---|---|
| taattcccag agtaataa | | 18 |

<210> SEQ ID NO 92
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 92

| | | |
|---|---|---|
| cacataattc ccagagta | | 18 |

<210> SEQ ID NO 93
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 93

| | | |
|---|---|---|
| agaacacata attcccag | | 18 |

<210> SEQ ID NO 94
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 94

| | | |
|---|---|---|
| gggcagaaca cataattc | | 18 |

<210> SEQ ID NO 95
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 95

| | | |
|---|---|---|
| gatggggcag aacacata | | 18 |

<210> SEQ ID NO 96
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 96
gagtgatggg gcagaaca                                                  18

<210> SEQ ID NO 97
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 97
gagagagtga tggggcag                                                  18

<210> SEQ ID NO 98
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 98
ttaagagaga gtgatggg                                                  18

<210> SEQ ID NO 99
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 99
ccaattaaga gagagtga                                                  18

<210> SEQ ID NO 100
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 100
aaatccaatt aagagaga                                                  18

<210> SEQ ID NO 101
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 101
ttaaaaatcc aattaaga                                                  18

<210> SEQ ID NO 102
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 102
aattttaaaa atccaatt                                                  18
```

<210> SEQ ID NO 103
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 103
atataatttt aaaaatcc                                                   18

<210> SEQ ID NO 104
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 104
atgaatataa ttttaaaa                                                   18

<210> SEQ ID NO 105
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 105
caatatgaat ataatttt                                                   18

<210> SEQ ID NO 106
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 106
cctgcaatat gaatataa                                                   18

<210> SEQ ID NO 107
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 107
gagtcctgca atatgaat                                                   18

<210> SEQ ID NO 108
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 108
tgccgagtcc tgcaatat                                                   18

<210> SEQ ID NO 109
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 109
cttctgccga gtcctgca                                                 18

<210> SEQ ID NO 110
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 110
aggtcttctg ccgagtcc                                                 18

<210> SEQ ID NO 111
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 111
tcgaaggtct tctgccga                                                 18

<210> SEQ ID NO 112
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 112
tctctcgaag gtcttctg                                                 18

<210> SEQ ID NO 113
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 113
cctttctctc gaaggtct                                                 18

<210> SEQ ID NO 114
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 114
tctacctttc tctcgaag                                                 18

<210> SEQ ID NO 115
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 115
attttctacc tttctctc                                                 18

<210> SEQ ID NO 116

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 116
tcttattttc tacctttc                                                  18

<210> SEQ ID NO 117
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 117
aaattcttat tttctacc                                                  18

<210> SEQ ID NO 118
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 118
agccaaattc ttattttc                                                  18

<210> SEQ ID NO 119
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 119
agagagccaa attcttat                                                  18

<210> SEQ ID NO 120
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 120
acacagagag ccaaattc                                                  18

<210> SEQ ID NO 121
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 121
gctcacacag agagccaa                                                  18

<210> SEQ ID NO 122
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 122
```

-continued acatgctcac acagagag                                              18

<210> SEQ ID NO 123
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 123
gcacacatgc tcacacag                                              18

<210> SEQ ID NO 124
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 124
acacgcacac atgctcac                                              18

<210> SEQ ID NO 125
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 125
gcacacacgc acacatgc                                              18

<210> SEQ ID NO 126
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 126
tctcgcacac acgcacac                                              18

<210> SEQ ID NO 127
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 127
tctctctcgc acacacgc                                              18

<210> SEQ ID NO 128
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 128
tctctctctc tcgcacac                                              18

<210> SEQ ID NO 129
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 129
tctgtctctc tctctcgc                                                   18

<210> SEQ ID NO 130
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 130
gctgtctgtc tctctctc                                                   18

<210> SEQ ID NO 131
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 131
gcaggctgtc tgtctctc                                                   18

<210> SEQ ID NO 132
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 132
ttaggcaggc tgtctgtc                                                   18

<210> SEQ ID NO 133
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 133
cttcttaggc aggctgtc                                                   18

<210> SEQ ID NO 134
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 134
atttcttctt aggcaggc                                                   18

<210> SEQ ID NO 135
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 135
attcatttct tcttaggc                                                   18
```

<210> SEQ ID NO 136
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 136
tcacattcat ttcttctt                                                 18

<210> SEQ ID NO 137
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 137
gcattcacat tcatttct                                                 18

<210> SEQ ID NO 138
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 138
agccgcattc acattcat                                                 18

<210> SEQ ID NO 139
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 139
cacaagccgc attcacat                                                 18

<210> SEQ ID NO 140
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 140
gtgccacaag ccgcattc                                                 18

<210> SEQ ID NO 141
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 141
aactgtgcca caagccgc                                                 18

<210> SEQ ID NO 142
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 142
tgtcaactgt gccacaag                                                     18

<210> SEQ ID NO 143
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 143
tccttgtcaa ctgtgcca                                                     18

<210> SEQ ID NO 144
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 144
atcatccttg tcaactgt                                                     18

<210> SEQ ID NO 145
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 145
atttatcatc cttgtcaa                                                     18

<210> SEQ ID NO 146
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 146
attgatttat catccttg                                                     18

<210> SEQ ID NO 147
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 147
cattattgat ttatcatc                                                     18

<210> SEQ ID NO 148
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 148
cttgcattat tgatttat                                                     18

```
<210> SEQ ID NO 149
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 149
taagcttgca ttattgat                                                 18

<210> SEQ ID NO 150
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 150
atagtaagct tgcattat                                                 18

<210> SEQ ID NO 151
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 151
aatgatagta agcttgca                                                 18

<210> SEQ ID NO 152
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 152
cataaatgat agtaagct                                                 18

<210> SEQ ID NO 153
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 153
tattcataaa tgatagta                                                 18

<210> SEQ ID NO 154
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 154
ttgctattca taaatgat                                                 18

<210> SEQ ID NO 155
<211> LENGTH: 18
<212> TYPE: DNA
<213> ORGANISM: Artificial sequence
<220> FEATURE:
<223> OTHER INFORMATION: Synthetic oligonucleotide
```

<400> SEQUENCE: 155
agtattgcta ttcataaa                                                18

<210> SEQ ID NO 156
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 156
cttcagtatt gctattca                                                18

<210> SEQ ID NO 157
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 157
atttcttcag tattgcta                                                18

<210> SEQ ID NO 158
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 158
tttaatttct tcagtatt                                                18

<210> SEQ ID NO 159
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 159
ttgttttaat ttcttcag                                                18

<210> SEQ ID NO 160
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 160
tcttttgttt taatttct                                                18

<210> SEQ ID NO 161
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 161
gcaatctttt gttttaat                                                18

<210> SEQ ID NO 162
<211> LENGTH: 18

```
<212> TYPE: DNA
<213> ORGANISM: Artificial sequence
<220> FEATURE:
<223> OTHER INFORMATION: Synthetic oligonucleotide

<400> SEQUENCE: 162
gacagcaatc ttttgttt                                                  18

<210> SEQ ID NO 163
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 163
ttgagacagc aatctttt                                                  18

<210> SEQ ID NO 164
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 164
tatattgaga cagcaatc                                                  18

<210> SEQ ID NO 165
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 165
aagatatatt gagacagc                                                  18

<210> SEQ ID NO 166
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 166
gtaataaaat ccccaggt                                                  18

<210> SEQ ID NO 167
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 167
cagagtaata aaatcccc                                                  18

<210> SEQ ID NO 168
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 168
```

-continued ttcccagagt aataaaat                                        18

<210> SEQ ID NO 169
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 169
ataattccca gagtaata                                        18

<210> SEQ ID NO 170
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 170
acacataatt cccagagt                                        18

<210> SEQ ID NO 171
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 171
cagaacacat aattccca                                        18

<210> SEQ ID NO 172
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 172
ggggcagaac acataatt                                        18

<210> SEQ ID NO 173
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 173
tgatggggca gaacacat                                        18

<210> SEQ ID NO 174
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 174
agagtgatgg ggcagaac                                        18

<210> SEQ ID NO 175
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 175
agagagagtg atggggca                                                    18

<210> SEQ ID NO 176
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 176
attaagagag agtgatgg                                                    18

<210> SEQ ID NO 177
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 177
tccaattaag agagagtg                                                    18

<210> SEQ ID NO 178
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 178
aaaatccaat taagagag                                                    18

<210> SEQ ID NO 179
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 179
tttaaaaatc caattaag                                                    18

<210> SEQ ID NO 180
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 180
taattttaaa aatccaat                                                    18

<210> SEQ ID NO 181
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 181
aatataattt taaaaatc                                                    18
```

```
<210> SEQ ID NO 182
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 182
tatgaatata attttaaa                                                 18

<210> SEQ ID NO 183
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 183
gcaatatgaa tataattt                                                 18

<210> SEQ ID NO 184
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 184
tcctgcaata tgaatata                                                 18

<210> SEQ ID NO 185
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 185
cgagtcctgc aatatgaa                                                 18

<210> SEQ ID NO 186
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 186
ctgccgagtc ctgcaata                                                 18

<210> SEQ ID NO 187
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 187
tcttctgccg agtcctgc                                                 18

<210> SEQ ID NO 188
<211> LENGTH: 18
<212> TYPE: DNA
<213> ORGANISM: Artificial sequence
<220> FEATURE:
<223> OTHER INFORMATION: Synthetic oligonucleotide
```

```
-continued

<400> SEQUENCE: 188
aaggtcttct gccgagtc                                                  18

<210> SEQ ID NO 189
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 189
ctcgaaggtc ttctgccg                                                  18

<210> SEQ ID NO 190
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 190
ttctctcgaa ggtcttct                                                  18

<210> SEQ ID NO 191
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 191
acctttctct cgaaggtc                                                  18

<210> SEQ ID NO 192
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 192
ttctaccttt ctctcgaa                                                  18

<210> SEQ ID NO 193
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 193
tattttctac ctttctct                                                  18

<210> SEQ ID NO 194
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 194
ttcttatttt ctacttt                                                   18

<210> SEQ ID NO 195
```

-continued

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 195
caaattctta ttttctac                                                 18

<210> SEQ ID NO 196
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 196
gagccaaatt cttatttt                                                 18

<210> SEQ ID NO 197
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 197
cagagagcca aattctta                                                 18

<210> SEQ ID NO 198
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 198
cacacagaga gccaaatt                                                 18

<210> SEQ ID NO 199
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 199
tgctcacaca gagagcca                                                 18

<210> SEQ ID NO 200
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 200
cacatgctca cacagaga                                                 18

<210> SEQ ID NO 201
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 201
```
cgcacacatg ctcacaca					18

<210> SEQ ID NO 202
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 202
cacacgcaca catgctca					18

<210> SEQ ID NO 203
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 203
cgcacacacg cacacatg					18

<210> SEQ ID NO 204
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 204
ctctcgcaca cacgcaca					18

<210> SEQ ID NO 205
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 205
ctctctctcg cacacacg					18

<210> SEQ ID NO 206
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 206
gtctctctct ctcgcaca					18

<210> SEQ ID NO 207
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 207
gtctgtctct ctctctcg					18

<210> SEQ ID NO 208
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 208
ggctgtctgt ctctctct                                                  18

<210> SEQ ID NO 209
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 209
ggcaggctgt ctgtctct                                                  18

<210> SEQ ID NO 210
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 210
cttaggcagg ctgtctgt                                                  18

<210> SEQ ID NO 211
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 211
tcttcttagg caggctgt                                                  18

<210> SEQ ID NO 212
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 212
catttcttct taggcagg                                                  18

<210> SEQ ID NO 213
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 213
cattcatttc ttcttagg                                                  18

<210> SEQ ID NO 214
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 214
ttcacattca tttcttct                                                  18
```

```
<210> SEQ ID NO 215
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 215
cgcattcaca ttcatttc                                                 18

<210> SEQ ID NO 216
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 216
aagccgcatt cacattca                                                 18

<210> SEQ ID NO 217
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 217
ccacaagccg cattcaca                                                 18

<210> SEQ ID NO 218
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 218
tgtgccacaa gccgcatt                                                 18

<210> SEQ ID NO 219
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 219
caactgtgcc acaagccg                                                 18

<210> SEQ ID NO 220
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 220
ttgtcaactg tgccacaa                                                 18

<210> SEQ ID NO 221
<211> LENGTH: 18
<212> TYPE: DNA
<213> ORGANISM: Artificial sequence
<220> FEATURE:
```

<223> OTHER INFORMATION: Synthetic oligonucleotide

<400> SEQUENCE: 221
atccttgtca actgtgcc                                                    18

<210> SEQ ID NO 222
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 222
tatcatcctt gtcaactg                                                    18

<210> SEQ ID NO 223
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 223
gatttatcat ccttgtca                                                    18

<210> SEQ ID NO 224
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 224
tattgattta tcatcctt                                                    18

<210> SEQ ID NO 225
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 225
gcattattga tttatcat                                                    18

<210> SEQ ID NO 226
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 226
gcttgcatta ttgattta                                                    18

<210> SEQ ID NO 227
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 227
gtaagcttgc attattga                                                    18

```
<210> SEQ ID NO 228
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 228
gatagtaagc ttgcatta                                                 18

<210> SEQ ID NO 229
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 229
aaatgatagt aagcttgc                                                 18

<210> SEQ ID NO 230
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 230
tcataaatga tagtaagc                                                 18

<210> SEQ ID NO 231
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 231
ctattcataa atgatagt                                                 18

<210> SEQ ID NO 232
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 232
attgctattc ataaatga                                                 18

<210> SEQ ID NO 233
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 233
cagtattgct attcataa                                                 18

<210> SEQ ID NO 234
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 234
tcttcagtat tgctattc                                              18

<210> SEQ ID NO 235
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 235
aatttcttca gtattgct                                              18

<210> SEQ ID NO 236
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 236
ttttaatttc ttcagtat                                              18

<210> SEQ ID NO 237
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 237
tttgttttaa tttcttca                                              18

<210> SEQ ID NO 238
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 238
atcttttgtt ttaatttc                                              18

<210> SEQ ID NO 239
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 239
agcaatcttt tgttttaa                                              18

<210> SEQ ID NO 240
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 240
agacagcaat cttttgtt                                              18

<210> SEQ ID NO 241
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 241
attgagacag caatcttt                                               18

<210> SEQ ID NO 242
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 242
atatattgag acagcaat                                               18

<210> SEQ ID NO 243
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 243
taagatatat tgagacag                                               18

<210> SEQ ID NO 244
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 244
agtaataaaa tccccagg                                               18

<210> SEQ ID NO 245
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 245
ccagagtaat aaaatccc                                               18

<210> SEQ ID NO 246
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 246
attcccagag taataaaa                                               18

<210> SEQ ID NO 247
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 247
```

-continued cataattccc agagtaat                                               18

<210> SEQ ID NO 248
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 248
aacacataat tcccagag                                               18

<210> SEQ ID NO 249
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 249
gcagaacaca taattccc                                               18

<210> SEQ ID NO 250
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 250
tggggcagaa cacataat                                               18

<210> SEQ ID NO 251
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 251
gtgatggggc agaacaca                                               18

<210> SEQ ID NO 252
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 252
gagagtgatg gggcagaa                                               18

<210> SEQ ID NO 253
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 253
aagagagagt gatggggc                                               18

<210> SEQ ID NO 254
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 254
aattaagaga gagtgatg                                                 18

<210> SEQ ID NO 255
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 255
atccaattaa gagagagt                                                 18

<210> SEQ ID NO 256
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 256
aaaaatccaa ttaagaga                                                 18

<210> SEQ ID NO 257
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 257
ttttaaaaat ccaattaa                                                 18

<210> SEQ ID NO 258
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 258
ataattttaa aaatccaa                                                 18

<210> SEQ ID NO 259
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 259
gaatataatt ttaaaaat                                                 18

<210> SEQ ID NO 260
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 260
atatgaatat aattttaa                                                 18
```

```
<210> SEQ ID NO 261
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 261
tgcaatatga atataatt                                                 18

<210> SEQ ID NO 262
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 262
gtcctgcaat atgaatat                                                 18

<210> SEQ ID NO 263
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 263
ccgagtcctg caatatga                                                 18

<210> SEQ ID NO 264
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 264
tctgccgagt cctgcaat                                                 18

<210> SEQ ID NO 265
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 265
gtcttctgcc gagtcctg                                                 18

<210> SEQ ID NO 266
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 266
gaaggtcttc tgccgagt                                                 18

<210> SEQ ID NO 267
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 267
tctcgaaggt cttctgcc                                          18

<210> SEQ ID NO 268
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 268
tttctctcga aggtcttc                                          18

<210> SEQ ID NO 269
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 269
tacctttctc tcgaaggt                                          18

<210> SEQ ID NO 270
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 270
tttctacctt tctctcga                                          18

<210> SEQ ID NO 271
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 271
ttattttcta cctttctc                                          18

<210> SEQ ID NO 272
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 272
attcttattt tctacctt                                          18

<210> SEQ ID NO 273
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 273
ccaaattctt attttcta                                          18

<210> SEQ ID NO 274
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 274
agagccaaat tcttattt                                                     18

<210> SEQ ID NO 275
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 275
acagagagcc aaattctt                                                     18

<210> SEQ ID NO 276
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 276
tcacacagag agccaaat                                                     18

<210> SEQ ID NO 277
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 277
atgctcacac agagagcc                                                     18

<210> SEQ ID NO 278
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 278
acacatgctc acacagag                                                     18

<210> SEQ ID NO 279
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 279
acgcacacat gctcacac                                                     18

<210> SEQ ID NO 280
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 280
```
acacacgcac acatgctc                                            18

<210> SEQ ID NO 281
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 281
tcgcacacac gcacacat                                            18

<210> SEQ ID NO 282
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 282
tctctcgcac acacgcac                                            18

<210> SEQ ID NO 283
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 283
tctctctctc gcacacac                                            18

<210> SEQ ID NO 284
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 284
tgtctctctc tctcgcac                                            18

<210> SEQ ID NO 285
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 285
tgtctgtctc tctctctc                                            18

<210> SEQ ID NO 286
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 286
aggctgtctg tctctctc                                            18

<210> SEQ ID NO 287
<211> LENGTH: 18
<212> TYPE: DNA

<213> ORGANISM: Artificial sequence
<220> FEATURE:
<223> OTHER INFORMATION: Synthetic oligonucleotide

<400> SEQUENCE: 287
aggcaggctg tctgtctc                                                18

<210> SEQ ID NO 288
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 288
tcttaggcag gctgtctg                                                18

<210> SEQ ID NO 289
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 289
ttcttcttag gcaggctg                                                18

<210> SEQ ID NO 290
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 290
tcatttcttc ttaggcag                                                18

<210> SEQ ID NO 291
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 291
acattcattt cttcttag                                                18

<210> SEQ ID NO 292
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 292
attcacattc atttcttc                                                18

<210> SEQ ID NO 293
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 293
ccgcattcac attcattt                                                18

```
<210> SEQ ID NO 294
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 294
caagccgcat tcacattc                                                 18

<210> SEQ ID NO 295
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 295
gccacaagcc gcattcac                                                 18

<210> SEQ ID NO 296
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 296
ctgtgccaca agccgcat                                                 18

<210> SEQ ID NO 297
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 297
tcaactgtgc cacaagcc                                                 18

<210> SEQ ID NO 298
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 298
cttgtcaact gtgccaca                                                 18

<210> SEQ ID NO 299
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 299
catccttgtc aactgtgc                                                 18

<210> SEQ ID NO 300
<211> LENGTH: 18
<212> TYPE: DNA
<213> ORGANISM: Artificial sequence
<220> FEATURE:
```

<223> OTHER INFORMATION: Synthetic oligonucleotide

<400> SEQUENCE: 300
ttatcatcct tgtcaact                                                18

<210> SEQ ID NO 301
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 301
tgatttatca tccttgtc                                                18

<210> SEQ ID NO 302
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 302
ttattgattt atcatcct                                                18

<210> SEQ ID NO 303
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 303
tgcattattg atttatca                                                18

<210> SEQ ID NO 304
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 304
agcttgcatt attgattt                                                18

<210> SEQ ID NO 305
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 305
agtaagcttg cattattg                                                18

<210> SEQ ID NO 306
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 306
tgatagtaag cttgcatt                                                18

```
<210> SEQ ID NO 307
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 307
taaatgatag taagcttg                                                 18

<210> SEQ ID NO 308
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 308
ttcataaatg atagtaag                                                 18

<210> SEQ ID NO 309
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 309
gctattcata aatgatag                                                 18

<210> SEQ ID NO 310
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 310
tattgctatt cataaatg                                                 18

<210> SEQ ID NO 311
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 311
tcagtattgc tattcata                                                 18

<210> SEQ ID NO 312
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 312
ttcttcagta ttgctatt                                                 18

<210> SEQ ID NO 313
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 313
taatttcttc agtattgc                                               18

<210> SEQ ID NO 314
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 314
gttttaattt cttcagta                                               18

<210> SEQ ID NO 315
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 315
ttttgtttta atttcttc                                               18

<210> SEQ ID NO 316
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 316
aatcttttgt tttaattt                                               18

<210> SEQ ID NO 317
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 317
cagcaatctt ttgtttta                                               18

<210> SEQ ID NO 318
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 318
gagacagcaa tcttttgt                                               18

<210> SEQ ID NO 319
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 319
tattgagaca gcaatctt                                               18

<210> SEQ ID NO 320
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 320
gatatattga gacagcaa                                                18

<210> SEQ ID NO 321
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 321
ataagatata ttgagaca                                                18
```

COMPOUNDS AND METHODS FOR INCREASING STMN2 EXPRESSION

SEQUENCE LISTING

The present application is being filed along with a Sequence Listing in electronic format. The Sequence Listing is provided as a file entitled BIOL0338USASEQ_ST25.txt, created on Dec. 1, 2020, which is 140 KB in size. The information in the electronic format of the sequence listing is incorporated herein by reference in its entirety.

FIELD

Provided are compounds, methods, and pharmaceutical compositions for increasing the amount or activity of STMN2 RNA in a cell or animal, and in certain instances increasing the amount of stathmin-2 protein in a cell or animal. Such compounds, methods, and pharmaceutical compositions are useful to ameliorate at least one symptom of a neurodegenerative disease. Such symptoms include ataxia, neuropathy, synaptic dysfunction, deficits in cognition, and decreased longevity. Such neurodegenerative diseases include amyotrophic lateral sclerosis (ALS), frontotemporal dementia (FTD), Alzheimer's disease (AD), and dementia with Lewy bodies (DLB).

BACKGROUND

The STMN2 gene encodes the stathmin-2 protein, a member of the stathmin family of phosphoproteins. Stathmin proteins function in microtubule dynamics and signal transduction. Stathmin-2 plays a regulatory role in neuronal growth and is also thought to be involved in osteogenesis.

Amyotrophic lateral sclerosis (ALS, also known as Lou Gehrig's disease) is a disorder characterized by a selective degeneration of upper and lower motor neurons (Rowland, N. Engl. J. Med. 2001, 344, 1688-1700). ALS is a devastating progressive neurodegenerative disease affecting as many as 30,000 Americans at any given time. The progressive degeneration of the motor neurons in ALS eventually leads to their death. When the motor neurons die, the ability of the brain to initiate and control muscle movement is lost. With voluntary muscle action progressively affected, patients in the later stages of the disease may become totally paralyzed.

Frontotemporal dementia (FTD) refers to a group of disorders caused by progressive nerve cell loss in the brain's frontal lobes or temporal lobes. Nerve cell damage caused by FTD leads to loss of function in the frontal lobes or temporal lobes, which variably cause deterioration in behavior and personality, language disturbances, or alterations in muscle or motor functions.

Alzheimer's disease (AD) is an irreversible, progressive brain disorder that slowly destroys memory and thinking skills, and eventually the ability to carry out the simplest tasks. AD is the most common cause of dementia among older adults. Dementia is the loss of cognitive functioning and behavioral abilities to such an extent that it interferes with a person's daily life and activities. Dementia ranges in severity from the mildest stage, when it is just beginning to affect a person's functioning, to the most severe stage, when the person must depend completely on others for basic activities of daily living.

Dementia with Lewy bodies (DLB) is a type of progressive dementia that leads to a decline in thinking, reasoning and independent function because of abnormal Lewy body deposition in neurons. DLB causes a progressive decline in mental abilities. People with DLB may experience visual hallucinations, and changes in alertness and attention. Other effects include Parkinson's disease-like symptoms such as rigid muscles, slow movement, and tremors.

Currently there is a lack of acceptable options for treating neurodegenerative diseases such as amyotrophic lateral sclerosis (ALS), frontotemporal dementia (FTD), Alzheimer's disease (AD), and dementia with Lewy bodies (DLB). It is therefore an object herein to provide compounds, methods, and pharmaceutical compositions for the treatment of such diseases.

SUMMARY OF THE INVENTION

Provided herein are compounds, methods, and pharmaceutical compositions for increasing the amount or activity of STMN2 RNA, and in certain embodiments increasing the amount of stathmin-2 protein in a cell or animal. While not limited to a particular mechanism, it is thought that the modified oligonucleotides described herein increase STMN2 RNA expression by preventing usage of a premature polyadenylation site in the first intron of STMN2 pre-mRNA. In certain embodiments, the animal has a neurodegenerative disease. In certain embodiments, the animal has amyotrophic lateral sclerosis (ALS), frontotemporal dementia (FTD), Alzheimer's disease (AD), and dementia with Lewy bodies (DLB). In certain embodiments, compounds useful for increasing expression of STMN2 RNA are oligomeric compounds or modified oligonucleotides. In certain embodiments, the oligomeric compound comprises a modified oligonucleotide.

Also provided are methods useful for ameliorating at least one symptom of a neurodegenerative disease. In certain embodiments, the neurodegenerative disease is amyotrophic lateral sclerosis (ALS), frontotemporal dementia (FTD), Alzheimer's disease (AD), and dementia with Lewy bodies (DLB). In certain embodiments symptoms include ataxia, neuropathy, synaptic dysfunction, deficits in cognition, and decreased longevity. In certain embodiments, amelioration of these symptoms results in improved motor function, reduced neuropathy, improved synaptic function, improved cognition, and survival.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyribosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "5-methyl cytosine" means a cytosine modified with a methyl group attached to the 5-position. A 5-methyl cytosine is a modified nucleobase.

As used herein, "administering" means providing a pharmaceutical agent to an animal.

As used herein, "animal" means a human or non-human animal.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound or oligomeric duplex capable of achieving at least one antisense activity.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom is ataxia, neuropathy, synaptic dysfunction, deficits in cognition, and decreased longevity. In certain embodiments, amelioration of these symptoms results in improved motor function, reduced neuropathy, improved synaptic function, improved cognition, and survival.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "constrained ethyl" or "cEt" or "cEt modified sugar" means a β-D ribosyl bicyclic sugar moiety wherein the second ring of the bicyclic sugar is formed via a bridge connecting the 4'-carbon and the 2'carbon of the β-D ribosyl sugar moiety, wherein the bridge has the formula 4'-CH(CH$_3$)—O-2', and wherein the methyl group of the bridge is in the S configuration.

As used herein, "cEt" nucleoside" means a nucleoside comprising a cEt modified sugar.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chiraly enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." Unless otherwise indicated, "gapmer" refers to a sugar motif. Unless otherwise indicated, the sugar moieties of the nucleosides of the gap of a gapmer are unmodified 2'-deoxyribosyl. Thus, the term "MOE gapmer" indicates a gapmer having a sugar motif of 2'-MOE nucleosides in both wings and a gap of 2'-deoxynucleosides. Unless otherwise indicated, a MOE gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid amenable to oligomeric compound-mediated increase of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "increasing the amount or activity" refers to more transcriptional expression or activity relative to the transcriptional expression or activity in an untreated or control sample.

As used herein, the term "internucleoside linkage" is the covalent linkage between adjacent nucleosides in an oligonucleotide. As used herein "modified internucleoside linkage" means any internucleoside linkage other than a phosphodiester internucleoside linkage. "Phosphorothioate linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "MOE" means methoxyethyl. "2'-MOE" or "2'-MOE modified sugar" means a 2'-OCH$_2$CH$_2$OCH$_3$ group in place of the 2' OH group of a ribosyl sugar moiety.

As used herein, "2'-MOE nucleoside" means a nucleoside comprising a 2'-MOE modified sugar. As used herein, "motif" means the pattern of unmodified and/or modified sugar moieties, nucleobases, and/or internucleoside linkages, in an oligonucleotide.

As used herein, "neurodegenerative disease" means a condition marked by progressive loss of structure or function of neurons, including death of neurons. In certain embodiments, neurodegenerative disease is amyotrophic lateral sclerosis (ALS), frontotemporal dementia (FTD), Alzheimer's disease (AD), and dementia with Lewy bodies (DLB).

As used herein, "nucleobase" means an unmodified nucleobase or a modified nucleobase. As used herein an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution, or sterile artificial cerebrospinal fluid.

As used herein "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein, "phosphorus moiety" means a group of atoms comprising a phosphorus atom. In certain embodiments, a phosphorus moiety comprises a mono-, di-, or tri-phosphate, or phosphorothioate.

As used herein "prodrug" means a therapeutic agent in a form outside the body that is converted to a different form within an animal or cells thereof. Typically, conversion of a prodrug within the animal is facilitated by the action of an enzyme (e.g., endogenous or viral enzyme) or chemicals present in cells or tissues and/or by physiologic conditions.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "standard cell assay" means the assay described in Example 1 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to an animal. For example, a therapeutically effective amount improves a symptom of a disease.

The present disclosure provides the following non-limiting numbered embodiments:

Embodiment 1

An oligomeric compound, comprising a modified oligonucleotide consisting of 12 to 50 linked nucleosides wherein the nucleobase sequence of the modified oligonucleotide is at least 90% complementary to an equal length portion of a STMN2 nucleic acid, and wherein the modified oligonucleotide comprises at least one modification selected from a modified sugar, a sugar surrogate, and a modified internucleoside linkage.

Embodiment 2

An oligomeric compound, comprising a modified oligonucleotide consisting of 12 to 50 linked nucleosides and having a nucleobase sequence comprising at least 8, at least 9, at least 10, at least 11, at least 12, at least 13, at least 14, at least 15, at least 16, at least 17, or at least 18 consecutive nucleobases of any of the nucleobase sequences of SEQ ID NOs: 10-321.

Embodiment 3

An oligomeric compound, comprising a modified oligonucleotide consisting of 12 to 50 linked nucleosides and having a nucleobase sequence comprising at least 8, at least 9, at least 10, at least 11, at least 12, at least 13, at least 14, at least 15, at least 16, at least 17, or at least 18 consecutive nucleobases complementary to:
  8819-8841 of SEQ ID NO: 1 or 100-122 of SEQ ID NO: 2;
  8827-8851 of SEQ ID NO: 1 or 108-132 of SEQ ID NO: 2;
  8836-8880 of SEQ ID NO: 1 or 117-161 of SEQ ID NO 2; or
  8913-8948 of SEQ ID NO: 1 or 194-229 of SEQ ID NO 2.

Embodiment 4

The oligomeric compound of any one of embodiments 1-3, wherein the STMN2 nucleic acid has the nucleobase sequence of SEQ ID NOs: 1 or SEQ ID NO: 2.

Embodiment 5

The oligomeric compound of any one of embodiments 1-4, wherein the modified oligonucleotide is a single-stranded modified oligonucleotide.

Embodiment 6

The oligomeric compound of any one of embodiments 1-5, wherein at least one internucleoside linkage of the modified oligonucleotide is a modified internucleoside linkage.

Embodiment 7

The oligomeric compound of embodiment 6, wherein the modified internucleoside linkage is a phosphorothioate internucleoside linkage.

Embodiment 8

The oligomeric compound of any one of embodiments 1-5, wherein each internucleoside linkage of the modified oligonucleotide is a modified internucleoside linkage.

Embodiment 9

The oligomeric compound of embodiment 8, wherein each modified internucleoside linkage of the modified oligonucleotide is a phosphorothioate internucleoside linkage.

Embodiment 10

The oligomeric compound of any one of embodiments 1-7, wherein at least one internucleoside linkage of the modified oligonucleotide is a phosphodiester internucleoside linkage.

Embodiment 11

The oligomeric compound of any one of embodiments 1-7 and 10, wherein each internucleoside linkage of the modified oligonucleotide is either a phosphodiester internucleoside linkage or a phosphorothioate internucleoside linkage.

Embodiment 12

The oligomeric compound of any one of embodiments 1-11, wherein at least one nucleobase of the modified oligonucleotide comprises a modified nucleobase.

Embodiment 13

The oligomeric compound of embodiment 12, wherein the modified nucleobase is a 5-methyl cytosine.

Embodiment 14

The oligomeric compound of any one of embodiments 1-13, wherein the modified oligonucleotide comprises at least 1, at least 2, at least 3, at least 4, at least 5, at least 6, at least 7, at least 8, at least 9, at least 10, at least 11, at least 12, at least 13, at least 14, at least 15, at least 16, at least 17, or at least 18 modified nucleosides comprising a modified sugar moiety.

Embodiment 15

The oligomeric compound of embodiment 14, wherein the modified oligonucleotide comprises at least 1, at least 2, at least 3, at least 4, at least 5, at least 6, at least 7, at least 8, at least 9, at least 10, at least 11, at least 12, at least 13, at least 14, at least 15, at least 16, at least 17, or at least 18 modified nucleosides comprising a bicyclic sugar moiety.

Embodiment 16

The oligomeric compound of embodiment 15, wherein the modified oligonucleotide comprises at least 1 modified nucleoside comprising a bicyclic sugar moiety having a 2'-4' bridge, wherein the 2'-4' bridge is selected from —O—$CH_2$—; and —O—$CH(CH_3)$—.

Embodiment 17

The oligomeric compound of any of embodiments 1-13, wherein the modified oligonucleotide comprises at least 1 modified nucleoside comprising a non-bicyclic sugar moiety.

Embodiment 18

The oligomeric compound of embodiment 17, wherein the modified oligonucleotide comprises at least 1 modified nucleoside comprising a modified non-bicyclic sugar moiety comprising a 2'-MOE or 2'-OMe.

Embodiment 19

The oligomeric compound of embodiment 18, wherein each modified nucleoside of the modified oligonucleotide comprises a modified non-bicyclic sugar moiety comprising a 2'-MOE or 2'-OMe.

Embodiment 20

The oligomeric compound of any of embodiments 1-13, wherein the modified oligonucleotide comprises at least 1 modified nucleoside comprising a sugar surrogate.

Embodiment 21

The oligomeric compound of embodiment 20, wherein the modified oligonucleotide comprises at least 1 modified nucleoside comprising a sugar surrogate selected from morpholino and PNA.

Embodiment 22

The oligomeric compound of any of embodiments 1-18 and 20-21, wherein the modified oligonucleotide is a gapmer.

Embodiment 23

The oligomeric compound of any of embodiments 1-18 and 20-21, wherein the modified oligonucleotide has a sugar motif comprising:
a 5'-region consisting of 1-6 linked 5'-nucleosides;
a central region consisting of 6-10 linked central region nucleosides; and
a 3'-region consisting of 1-6 linked 5'-nucleosides;
wherein each of the 5'-region nucleosides and each of the 3'-region nucleosides comprises a modified sugar moiety and each of the central region nucleosides comprises a 2'-deoxynucleoside sugar moiety.

Embodiment 24

The oligomeric compound of embodiments 1-7 or 10-23, wherein the modified oligonucleotide consists of 20 linked nucleosides and has the following internucleoside motif: sooosssssssssssooss; wherein,
s=a phosphorothioate internucleoside linkage, and
o=a phosphodiester internucleoside linkage.

Embodiment 25

The oligomeric compound of any one of embodiments 1-23, wherein the modified oligonucleotide consists of 12-18, 12-20, 14-20, 16-20, or 17-19 linked nucleosides.

Embodiment 26

The oligomeric compound of any one of embodiments 1-23 and 25, wherein the modified oligonucleotide consists of 16, 17, or 18 linked nucleosides.

Embodiment 27

The oligomeric compound of any of embodiments 1-26 consisting of the modified oligonucleotide.

Embodiment 28

The oligomeric compound of any of embodiments 1-26 comprising a conjugate group comprising a conjugate moiety and a conjugate linker.

Embodiment 29

The oligomeric compound of embodiment 28, wherein the conjugate group comprises a GalNAc cluster comprising 1-3 GalNAc ligands.

Embodiment 30

The oligomeric compound of embodiment 28 or 29, wherein the conjugate linker consists of a single bond.

Embodiment 31

The oligomeric compound of embodiment 28, wherein the conjugate linker is cleavable.

Embodiment 32

The oligomeric compound of embodiment 28, wherein the conjugate linker comprises 1-3 linker-nucleosides.

Embodiment 33

The oligomeric compound of any of embodiments 28-32, wherein the conjugate group is attached to the modified oligonucleotide at the 5'-end of the modified oligonucleotide.

Embodiment 34

The oligomeric compound of any of embodiments 28-32, wherein the conjugate group is attached to the modified oligonucleotide at the 3'-end of the modified oligonucleotide.

Embodiment 35

The oligomeric compound of any of embodiments 1-26 or 28-34 comprising a terminal group.

Embodiment 36

The oligomeric compound of any of embodiments 1-35 wherein the oligomeric compound is a singled-stranded oligomeric compound.

Embodiment 37

The oligomeric compound of any of embodiments 1-31 or 33-34, wherein the oligomeric compound does not comprise linker-nucleosides.

Embodiment 38

An oligomeric duplex comprising an oligomeric compound of any of embodiments 1-35 and 37.

Embodiment 39

An antisense compound comprising or consisting of an oligomeric compound of any of embodiments 1-37 or an oligomeric duplex of embodiment 38.

Embodiment 40

A modified oligonucleotide consisting of 12 to 50 linked nucleosides and having a nucleobase sequence comprising at least 8, at least 9, at least 10, at least 11, at least 12, at least 13, at least 14, at least 15, at least 16, at least 17, or at least 18 consecutive nucleobases of any of the nucleobase sequences of SEQ ID NOs: 10-321.

Embodiment 41

A pharmaceutical composition comprising an oligomeric compound of any of embodiments 1-37, an oligomeric duplex of embodiment 38, an antisense compound of embodiment 39, or a modified oligonucleotide of embodiment 40 and at least one of a pharmaceutically acceptable carrier or diluent.

Embodiment 42

The pharmaceutical composition of embodiment 41, wherein the modified oligonucleotide is a sodium salt.

Embodiment 43

A method comprising administering to an animal the pharmaceutical composition of any of embodiments 41-42.

Embodiment 44

The method of embodiment 43, wherein the animal is a human.

Embodiment 45

A method of treating a disease associated with STMN2 comprising administering to an individual having or at risk for developing a disease associated with STMN2 a therapeutically effective amount of a pharmaceutical composition of embodiments 41 and 42, and thereby treating the disease associated with STMN2.

Embodiment 46

The method of embodiment 45, wherein the disease associated with STMN2 is a neurodegenerative disease.

Embodiment 47

The method of embodiment 46, wherein the neurodegenerative disease is amyotrophic lateral sclerosis (ALS), frontotemporal dementia (FTD), Alzheimer's disease (AD), and dementia with Lewy bodies (DLB).

Embodiment 48

The method of embodiment 47, wherein at least one symptom of the neurodegenerative disease is ameliorated.

Embodiment 49

The method of embodiment 48, wherein the symptom is ataxia, neuropathy, synaptic dysfunction, deficits in cognition, and decreased longevity.

I. Certain Oligonucleotides

In certain embodiments, provided herein are oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836).

In certain embodiments, a 2'-substituted non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted non-bicyclic modified nucleoside comprises a sugar moiety comprising a non-bridging 2'-substituent group selected from: F, OCH$_3$, and OCH$_2$CH$_2$OCH$_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt"), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O- 2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129, 8362-8379; Wengel et al., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

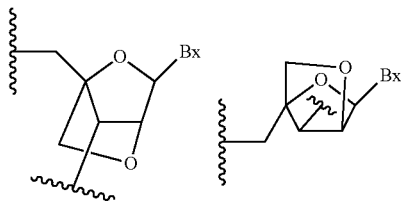

α-L-methyleneoxy (4'-$CH_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

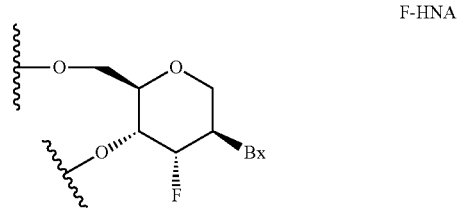

"F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

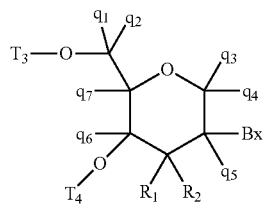

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

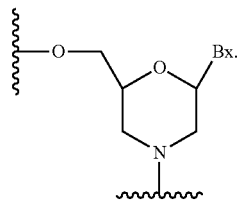

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie, International Edition*, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS-P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—);

siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., JACS 125, 8307 (2003), Wan et al. Nuc. Acid. Res. 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

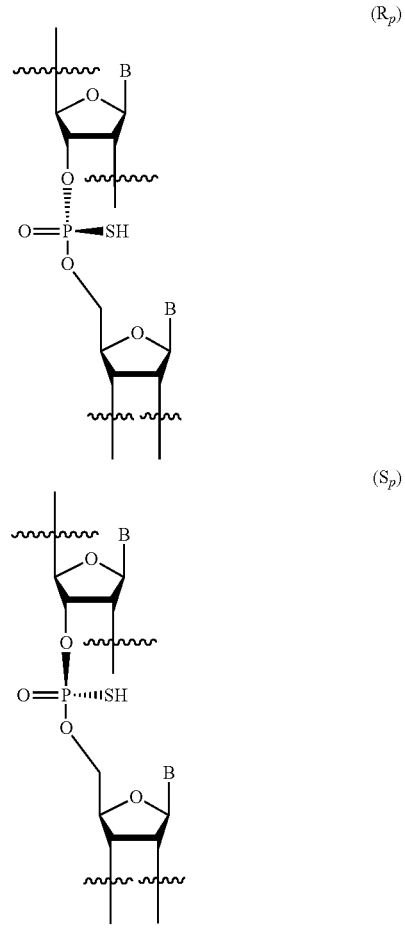

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside. In certain embodiments, at least one nucleoside of each wing of a gapmer is a modified nucleoside. In certain embodiments, at least two nucleosides of each wing of a gapmer are modified nucleosides. In certain embodiments, at least three nucleosides of each wing of a gapmer are modified nucleosides. In certain embodiments, at least four nucleosides of each wing of a gapmer are modified nucleosides.

In certain embodiments, the gap of a gapmer comprises 7-12 nucleosides. In certain embodiments, each nucleoside of the gap of a gapmer is an unmodified 2'-deoxy nucleoside.

In certain embodiments, the gapmer is a deoxy gapmer. In embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

Herein, the lengths (number of nucleosides) of the three regions of a gapmer may be provided using the notation [# of nucleosides in the 5'-wing]–[# of nucleosides in the gap]–[# of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprise unmodified deoxynucleosides sugars. Thus, a 5-10-5 MOE gapmer consists of 5 linked MOE modified nucleosides in the 5'-wing, 10 linked deoxynucleosides in the gap, and 5 linked MOE nucleosides in the 3'-wing.

In certain embodiments, modified oligonucleotides are 5-10-5 MOE gapmers. In certain embodiments, modified oligonucleotides are 3-10-3 BNA gapmers. In certain embodiments, modified oligonucleotides are 3-10-3 cEt gapmers. In certain embodiments, modified oligonucleotides are 3-10-3 LNA gapmers.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, modified oligonucleotides comprise or consist of a region having a fully modified sugar motif, wherein each nucleoside within the fully modified region comprises the same modified sugar moiety (uniformly modified sugar motif). In certain embodiments, the uniformly modified sugar motif is 7 to 20 nucleosides in length. In certain embodiments, each nucleoside of the uniformly modified sugar motif is a 2'-substituted nucleoside, a sugar surrogate, or a bicyclic nucleoside. In certain embodiments, each nucleoside of the uniformly modified sugar motif comprises either a 2'-OCH$_2$CH$_2$OCH$_3$ group or a 2'-OCH$_3$ group. In certain embodiments, modified oligonucleotides having at least one fully modified sugar motif may also have at least 1, at least 2, at least 3, or at least 4 2'-deoxynucleosides.

In certain embodiments, each nucleoside of the entire modified oligonucleotide comprises a modified sugar moiety (fully modified oligonucleotide). In certain embodiments, a fully modified oligonucleotide comprises different 2'-modifications. In certain embodiments, each nucleoside of a fully modified oligonucleotide is a 2'-substituted nucleoside, a sugar surrogate, or a bicyclic nucleoside. In certain embodiments, each nucleoside of a fully modified oligonucleotide comprises either a 2'-OCH$_2$CH$_2$OCH$_3$ group and at least one 2'-OCH$_3$ group.

In certain embodiments, each nucleoside of a fully modified oligonucleotide comprises the same 2'-modification (uniformly modified oligonucleotide). In certain embodiments, each nucleoside of a uniformly modified oligonucleotide is a 2'-substituted nucleoside, a sugar surrogate, or a bicyclic nucleoside. In certain embodiments, each nucleoside of a uniformly modified oligonucleotide comprises either a 2'-OCH$_2$CH$_2$OCH$_3$ group or a 2'-OCH$_3$ group In certain embodiments, modified oligonucleotides comprise at least 12, at last 13, at least 14, at least 15, at least 16, at least 17, at least 18, at least 19, or at least 20 nucleosides comprising a modified sugar moiety. In certain embodiments, each nucleoside of a modified oligonucleotide is a 2'-substituted nucleoside, a sugar surrogate, a bicyclic nucleoside, or a 2'-deoxynucleoside. In certain embodiments, each nucleoside of a modified oligonucleotide comprises a 2'-OCH$_2$CH$_2$OCH$_3$ group, a 2'-H(H) deoxyribosyl sugar moiety, or a cEt modified sugar.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

C. Certain Lengths

It is possible to increase or decrease the length of an oligonucleotide without eliminating activity. For example, in Woolf et al. (*Proc. Natl. Acad. Sci. USA* 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target RNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides D. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO* 1, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

B. Certain Terminal Groups

In certain embodiments, oligomeric compounds comprise one or more terminal groups. In certain such embodiments, oligomeric compounds comprise a stabilized 5'-phophate. Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a region complementary to a target nucleic acid and a second oligomeric compound having a region complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they increase the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid. In certain embodiments, hybridization of an antisense compound to a target nucleic acid results in an increase in the amount or activity of a target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature RNA and a pre-mRNA, including intronic, exonic and untranslated regions. In certain embodiments, the target RNA is a mature RNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is the RNA transcriptional product of a retrogene. In certain embodiments, the target nucleic acid is a non-coding RNA. In certain such embodiments, the target non-coding RNA is selected from: a long non-coding RNA, a short non-coding RNA, an intronic RNA molecule.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides that are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. STMN2

In certain embodiments, oligomeric compounds comprise or consist of an oligonucleotide comprising a region that is complementary to a target nucleic acid, wherein the target nucleic acid is STMN2. In certain embodiments, STMN2 nucleic acid has the sequence set forth in SEQ ID NO: 1 (complement of GENBANK Accession No. NC_000008.11 truncated from nucleobase 79608001 to 79669000) and SEQ ID NO: 2.

In certain embodiments, contacting a cell with an oligomeric compound complementary to SEQ ID NO: 1 or SEQ ID NO: 2 increases the amount of STMN2 RNA, and in certain embodiments increases the amount of stathmin-2 protein. In certain embodiments, contacting a cell in an animal with an oligomeric compound complementary to SEQ ID NO: 1 or SEQ ID NO: 2 ameliorates one or more symptoms of a neurodegenerative disease. Such symptoms include ataxia, neuropathy, synaptic dysfunction, deficits in cognition, and decreased longevity. In certain embodiments, contacting a cell in an animal with an oligonucleotide complementary to SEQ ID NO: 1 or SEQ ID NO: 2 results in improved motor function, reduced neuropathy, improved synaptic function, improved cognition, and survival.

VI. Certain Hotspot Regions

1. Nucleobases 8819-8841 of SEQ ID NO: 1 (also 100-122 of SEQ ID NO: 2)

In certain embodiments, nucleobases 8819-8841 of SEQ ID NO: 1 comprise a hotspot region. In certain embodiments, modified oligonucleotides are complementary to nucleobases 8819-8841 of SEQ ID NO: 1. In certain embodiments, such modified oligonucleotides are 18 nucleobases in length. In certain embodiments, such modified oligonucleotides are uniformly MOE modified oligonucleotides. In certain embodiments, the nucleosides of the modified oligonucleotides are linked by phosphorothioate internucleoside linkages.

The nucleobase sequences of SEQ ID Nos: 32, 33, 110, 188, 265, 266 are complementary to nucleobases 8819-8841 of SEQ ID NO: 1.

In certain embodiments, modified oligonucleotides complementary to nucleobases 8819-8841 of SEQ ID NO: 1 achieve at least 151% expression of STMN2 RNA in vitro in the standard cell assay.

2. Nucleobases 8827-8851 of SEQ ID NO: 1 (also 108-132 of SEQ ID NO: 2)

In certain embodiments, nucleobases 8827-8851 of SEQ ID NO: 1 comprise a hotspot region. In certain embodiments, modified oligonucleotides are complementary to nucleobases 8827-8851 of SEQ ID NO: 1. In certain embodiments, such modified oligonucleotides are 18 nucleobases in length. In certain embodiments, such modified oligonucleotides are uniformly MOE modified oligonucleotides. In certain embodiments, the nucleosides of the modified oligonucleotides are linked by phosphorothioate internucleoside linkages.

The nucleobase sequences of SEQ ID Nos: 34, 35, 112, 113, 190, 191, 267, and 268 are complementary to nucleobases 8819-8841 of SEQ ID NO: 1.

In certain embodiments, modified oligonucleotides complementary to nucleobases 8827-8851 of SEQ ID NO: 1 achieve at least 146% expression of STMN2 RNA in vitro in the standard cell assay.

3. Nucleobases 8836-8880 of SEQ ID NO: 1 (also 117-161 of SEQ ID NO: 2)

In certain embodiments, nucleobases 8836-8880 of SEQ ID NO: 1 comprise a hotspot region. In certain embodiments, modified oligonucleotides are complementary to nucleobases 8836-8880 of SEQ ID NO: 1. In certain embodiments, such modified oligonucleotides are 18 nucleobases in length. In certain embodiments, such modified oligonucleotides are uniformly MOE modified oligonucleotides. In certain embodiments, the nucleosides of the modified oligonucleotides are linked by phosphorothioate internucleoside linkages.

The nucleobase sequences of SEQ ID Nos: 36-42, 114-120, 192-198, and 270-276 are complementary to nucleobases 8836-8880 of SEQ ID NO: 1.

In certain embodiments, modified oligonucleotides complementary to nucleobases 8836-8880 of SEQ ID NO: 1 achieve at least 136% expression of STMN2 RNA in vitro in the standard cell assay.

4. Nucleobases 8913-8948 of SEQ ID NO: 1 (also 194-229 of SEQ ID NO: 2)

In certain embodiments, nucleobases 8913-8948 of SEQ ID NO: 1 comprise a hotspot region. In certain embodiments, modified oligonucleotides are complementary to nucleobases 8913-8948 of SEQ ID NO: 1. In certain embodiments, such modified oligonucleotides are 18 nucleobases in length. In certain embodiments, such modified oligonucleotides are uniformly MOE modified oligonucleotides. In certain embodiments, the nucleosides of the modified oligonucleotides are linked by phosphorothioate internucleoside linkages.

The nucleobase sequences of SEQ ID Nos: 56-59, 133-137, 211-215, and 289-293 are complementary to nucleobases 8913-8948 of SEQ ID NO: 1.

In certain embodiments, modified oligonucleotides complementary to nucleobases 8913-8948 of SEQ ID NO: 1 achieve at least 150% expression of STMN2 RNA in vitro in the standard cell assay.

C. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in a pharmacologically relevant tissue. In certain embodiments, the pharmacologically relevant tissues are the cells and tissues that comprise the central nervous system (CNS), including spinal cord, cortex, cerebellum, and pons.

VII. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS. In certain embodiments, a pharmaceutical composition comprises or consists of one or more oligomeric compound and artificial cerebrospinal fluid. In certain embodiments, the artificial cerebrospinal fluid is pharmaceutical grade.

In certain embodiments, a pharmaceutical composition comprises a modified oligonucleotide and artificial cerebrospinal fluid. In certain embodiments, a pharmaceutical composition consists of a modified oligonucleotide and artificial cerebrospinal fluid. In certain embodiments, a pharmaceutical composition consists essentially of a modified oligonucleotide and artificial cerebrospinal fluid. In certain embodiments, the artificial cerebrospinal fluid is pharmaceutical grade.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof.

Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal, intracerebroventricular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "ATmCGAUCG," wherein mC indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry included all such possible isomers, including their stereorandom and optically pure forms, unless specified otherwise. Likewise, all tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Effect of Uniformly MOE Modified Oligonucleotides with Phosphorothioate Internucleoside Linkages on Human STMN2 In Vitro, Single Dose Modified oligonucleotides complementary to a human STMN2 nucleic acid were designed and tested for their effect on STMN2 RNA cultured CRISPR-edited SH-SY5Y cells. SH-SY5Y cells were genetically engineered to express a familial ALS-causing mutation (asparagine substituted to serine at amino acid 352-TDP-43N352S) from both endogenous TDP-43 alleles using a CRISPR-Cas9 site selective nuclease.

Cultured CRISPR-edited SH-SY5Y cells at a density of 20,000 cells per well were transfected using electroporation with 7,000 nM concentration of modified oligonucleotide or no modified oligonucleotide for untreated controls. After approximately 24 hours, RNA was isolated from the cells and STMN2 RNA levels were measured by quantitative real-time PCR. Human primer probe set RTS40280 (forward sequence CCACGAACTTTAGCTTCTCCA, designated herein as SEQ ID NO: 3; reverse sequence GCCAATTGTTTCAGCACCTG, designated herein as SEQ ID NO: 4; probe sequence ACTTTCTTCTTTCCTCTGCAGCCTCC, designated herein as SEQ ID NO: 5) was used to measure mRNA levels. STMN2 mRNA levels were adjusted according to total RNA content, as measured by RiboGreen®. Results are presented in the tables below as percent control of the amount of STMN2 RNA, relative to untreated control cells.

The modified oligonucleotides in the tables below are uniformly modified oligonucleotides. The oligonucleotides are 18 nucleobases in length and each nucleoside has a 2'-MOE group. Each internucleoside linkage is a phosphorothioate internucleoside linkage and each cytosine residue is a 5-methyl cytosine. "Start Site" indicates the 5'-most nucleoside to which the gapmer is complementary in the human nucleic acid sequence. "Stop Site" indicates the 3'-most nucleoside to which the modified oligonucleotide is complementary in the human nucleic acid sequence.

Each modified oligonucleotide listed in the tables below is complementary to human STMN2 nucleic acid sequences SEQ ID NO: 1 and SEQ ID NO: 2, as indicated. As shown below, modified oligonucleotides complementary to human STMN2 increased the amount of human STMN2 RNA.

TABLE 1

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186531 | 8732 | 8749 | 13 | 30 | AATAAAATCCCCAGGTAT | 97 | 10 |
| 1186535 | 8736 | 8753 | 17 | 34 | GAGTAATAAAATCCCCAG | 103 | 11 |
| 1186539 | 8740 | 8757 | 21 | 38 | CCCAGAGTAATAAAATCC | 42 | 12 |

TABLE 1-continued

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186543 | 8744 | 8761 | 25 | 42 | AATTCCCAGAGTAATAAA | 86 | 13 |
| 1186547 | 8748 | 8765 | 29 | 46 | ACATAATTCCCAGAGTAA | 81 | 14 |
| 1186551 | 8752 | 8769 | 33 | 50 | GAACACATAATTCCCAGA | 70 | 15 |
| 1186555 | 8756 | 8773 | 37 | 54 | GGCAGAACACATAATTCC | 103 | 16 |
| 1186559 | 8760 | 8777 | 41 | 58 | ATGGGGCAGAACACATAA | 91 | 17 |
| 1186563 | 8764 | 8781 | 45 | 62 | AGTGATGGGGCAGAACAC | 88 | 18 |
| 1186567 | 8768 | 8785 | 49 | 66 | AGAGAGTGATGGGGCAGA | 113 | 19 |
| 1186571 | 8772 | 8789 | 53 | 70 | TAAGAGAGAGTGATGGGG | 115 | 20 |
| 1186575 | 8776 | 8793 | 57 | 74 | CAATTAAGAGAGAGTGAT | 112 | 21 |
| 1186579 | 8780 | 8797 | 61 | 78 | AATCCAATTAAGAGAGAG | 165 | 22 |
| 1186583 | 8784 | 8801 | 65 | 82 | TAAAAATCCAATTAAGAG | 166 | 23 |
| 1186587 | 8788 | 8805 | 69 | 86 | ATTTTAAAAATCCAATTA | 116 | 24 |
| 1186591 | 8792 | 8809 | 73 | 90 | TATAATTTTAAAAATCCA | 138 | 25 |
| 1186595 | 8796 | 8813 | 77 | 94 | TGAATATAATTTTAAAAA | 109 | 26 |
| 1186599 | 8800 | 8817 | 81 | 98 | AATATGAATATAATTTTA | 103 | 27 |
| 1186603 | 8804 | 8821 | 85 | 102 | CTGCAATATGAATATAAT | 156 | 28 |
| 1186607 | 8808 | 8825 | 89 | 106 | AGTCCTGCAATATGAATA | 192 | 29 |
| 1186611 | 8812 | 8829 | 93 | 110 | GCCGAGTCCTGCAATATG | 149 | 30 |
| 1186615 | 8816 | 8833 | 97 | 114 | TTCTGCCGAGTCCTGCAA | 127 | 31 |
| 1186619 | 8820 | 8837 | 101 | 118 | GGTCTTCTGCCGAGTCCT | 173 | 32 |
| 1186623 | 8824 | 8841 | 105 | 122 | CGAAGGTCTTCTGCCGAG | 175 | 33 |
| 1186627 | 8828 | 8845 | 109 | 126 | CTCTCGAAGGTCTTCTGC | 204 | 34 |
| 1186631 | 8832 | 8849 | 113 | 130 | CTTTCTCTCGAAGGTCTT | 190 | 35 |
| 1186635 | 8836 | 8853 | 117 | 134 | CTACCTTTCTCTCGAAGG | 160 | 36 |
| 1186639 | 8840 | 8857 | 121 | 138 | TTTTCTACCTTTCTCTCG | 173 | 37 |
| 1186643 | 8844 | 8861 | 125 | 142 | CTTATTTTCTACCTTTCT | 172 | 38 |
| 1186647 | 8848 | 8865 | 129 | 146 | AATTCTTATTTTCTACCT | 153 | 39 |
| 1186651 | 8852 | 8869 | 133 | 150 | GCCAAATTCTTATTTTCT | 211 | 40 |
| 1186655 | 8856 | 8873 | 137 | 154 | GAGAGCCAAATTCTTATT | 222 | 41 |
| 1186659 | 8860 | 8877 | 141 | 158 | CACAGAGAGCCAAATTCT | 193 | 42 |
| 1186663 | 8864 | 8881 | 145 | 162 | CTCACACAGAGAGCCAAA | 131 | 43 |
| 1186667 | 8868 | 8885 | 149 | 166 | CATGCTCACACAGAGAGC | 132 | 44 |
| 1186671 | 8872 | 8889 | 153 | 170 | CACACATGCTCACACAGA | 205 | 45 |
| 1186675 | 8876 | 8893 | 157 | 174 | CACGCACACATGCTCACA | 156 | 46 |
| 1186679 | 8880 | 8897 | 161 | 178 | CACACACGCACACATGCT | 157 | 47 |
| 1186683 | 8884 | 8901 | 165 | 182 | CTCGCACACACGCACACA | 131 | 48 |

TABLE 1-continued

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186687 | 8888 | 8905 | 169 | 186 | CTCTCTCGCACACACGCA | 152 | 49 |
| 1186691 | 8892 | 8909 | 173 | 190 | CTCTCTCTCTCGCACACA | 182 | 50 |
| 1186695 | 8896 | 8913 | 177 | 194 | CTGTCTCTCTCTCTCGCA | 162 | 51 |
| 1186699 | 8900 | 8917 | 181 | 198 | CTGTCTGTCTCTCTCTCT | 163 | 52 |
| 1186703 | 8904 | 8921 | 185 | 202 | CAGGCTGTCTGTCTCTCT | 117 | 53 |
| 1186707 | 8908 | 8925 | 189 | 206 | TAGGCAGGCTGTCTGTCT | 96 | 54 |
| 1186711 | 8912 | 8929 | 193 | 210 | TTCTTAGGCAGGCTGTCT | 136 | 55 |
| 1186715 | 8916 | 8933 | 197 | 214 | TTTCTTCTTAGGCAGGCT | 209 | 56 |
| 1186719 | 8920 | 8937 | 201 | 218 | TTCATTTCTTCTTAGGCA | 196 | 57 |
| 1186723 | 8924 | 8941 | 205 | 222 | CACATTCATTTCTTCTTA | 199 | 58 |
| 1186727 | 8928 | 8945 | 209 | 226 | CATTCACATTCATTTCTT | 218 | 59 |
| 1186731 | 8932 | 8949 | 213 | 230 | GCCGCATTCACATTCATT | 133 | 60 |
| 1186735 | 8936 | 8953 | 217 | 234 | ACAAGCCGCATTCACATT | 182 | 61 |
| 1186739 | 8940 | 8957 | 221 | 238 | TGCCACAAGCCGCATTCA | 164 | 62 |
| 1186743 | 8944 | 8961 | 225 | 242 | ACTGTGCCACAAGCCGCA | 139 | 63 |
| 1186747 | 8948 | 8965 | 229 | 246 | GTCAACTGTGCCACAAGC | 166 | 64 |
| 1186751 | 8952 | 8969 | 233 | 250 | CCTTGTCAACTGTGCCAC | 179 | 65 |
| 1186755 | 8956 | 8973 | 237 | 254 | TCATCCTTGTCAACTGTG | 155 | 66 |
| 1186759 | 8960 | 8977 | 241 | 258 | TTTATCATCCTTGTCAAC | 123 | 67 |
| 1186763 | 8964 | 8981 | 245 | 262 | TTGATTTATCATCCTTGT | 118 | 68 |
| 1186767 | 8968 | 8985 | 249 | 266 | ATTATTGATTTATCATCC | 115 | 69 |
| 1186771 | 8972 | 8989 | 253 | 270 | TTGCATTATTGATTTATC | 67 | 70 |
| 1186775 | 8976 | 8993 | 257 | 274 | AAGCTTGCATTATTGATT | 55 | 71 |
| 1186779 | 8980 | 8997 | 261 | 278 | TAGTAAGCTTGCATTATT | 78 | 72 |
| 1186783 | 8984 | 9001 | 265 | 282 | ATGATAGTAAGCTTGCAT | 80 | 73 |
| 1186787 | 8988 | 9005 | 269 | 286 | ATAAATGATAGTAAGCTT | 74 | 74 |
| 1186791 | 8992 | 9009 | 273 | 290 | ATTCATAAATGATAGTAA | 47 | 75 |
| 1186795 | 8996 | 9013 | 277 | 294 | TGCTATTCATAAATGATA | 54 | 76 |
| 1186799 | 9000 | 9017 | 281 | 298 | GTATTGCTATTCATAAAT | 64 | 77 |
| 1186803 | 9004 | 9021 | 285 | 302 | TTCAGTATTGCTATTCAT | 69 | 78 |
| 1186807 | 9008 | 9025 | 289 | 306 | TTTCTTCAGTATTGCTAT | 99 | 79 |
| 1186811 | 9012 | 9029 | 293 | 310 | TTAATTTCTTCAGTATTG | 127 | 80 |
| 1186815 | 9016 | 9033 | 297 | 314 | TGTTTTAATTTCTTCAGT | 124 | 81 |
| 1186819 | 9020 | 9037 | 301 | 318 | CTTTTGTTTTAATTTCTT | 83 | 82 |
| 1186823 | 9024 | 9041 | 305 | 322 | CAATCTTTTGTTTTAATT | 111 | 83 |

TABLE 1-continued

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186827 | 9028 | 9045 | 309 | 326 | ACAGCAATCTTTTGTTTT | 116 | 84 |
| 1186831 | 9032 | 9049 | 313 | 330 | TGAGACAGCAATCTTTTG | 147 | 85 |
| 1186835 | 9036 | 9053 | 317 | 334 | ATATTGAGACAGCAATCT | 103 | 86 |
| 1186839 | 9040 | 9057 | 321 | 338 | AGATATATTGAGACAGCA | 125 | 87 |

TABLE 2

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186532 | 8733 | 8750 | 14 | 31 | TAATAAAATCCCCAGGTA | 72 | 88 |
| 1186536 | 8737 | 8754 | 18 | 35 | AGAGTAATAAAATCCCCA | 103 | 89 |
| 1186540 | 8741 | 8758 | 22 | 39 | TCCCAGAGTAATAAAATC | 92 | 90 |
| 1186544 | 8745 | 8762 | 26 | 43 | TAATTCCCAGAGTAATAA | 119 | 91 |
| 1186548 | 8749 | 8766 | 30 | 47 | CACATAATTCCCAGAGTA | 100 | 92 |
| 1186552 | 8753 | 8770 | 34 | 51 | AGAACACATAATTCCCAG | 54 | 93 |
| 1186556 | 8757 | 8774 | 38 | 55 | GGGCAGAACACATAATTC | 80 | 94 |
| 1186560 | 8761 | 8778 | 42 | 59 | GATGGGGCAGAACACATA | 94 | 95 |
| 1186564 | 8765 | 8782 | 46 | 63 | GAGTGATGGGGCAGAACA | 98 | 96 |
| 1186568 | 8769 | 8786 | 50 | 67 | GAGAGAGTGATGGGGCAG | 89 | 97 |
| 1186572 | 8773 | 8790 | 54 | 71 | TTAAGAGAGTGATGGG | 134 | 98 |
| 1186576 | 8777 | 8794 | 58 | 75 | CCAATTAAGAGAGAGTGA | 109 | 99 |
| 1186580 | 8781 | 8798 | 62 | 79 | AAATCCAATTAAGAGAGA | 108 | 100 |
| 1186584 | 8785 | 8802 | 66 | 83 | TTAAAAATCCAATTAAGA | 118 | 101 |
| 1186588 | 8789 | 8806 | 70 | 87 | AATTTTAAAAATCCAATT | 124 | 102 |
| 1186592 | 8793 | 8810 | 74 | 91 | ATATAATTTTAAAAATCC | 118 | 103 |
| 1186596 | 8797 | 8814 | 78 | 95 | ATGAATATAATTTTAAAA | 92 | 104 |
| 1186600 | 8801 | 8818 | 82 | 99 | CAATATGAATATAATTTT | 101 | 105 |
| 1186604 | 8805 | 8822 | 86 | 103 | CCTGCAATATGAATATAA | 177 | 106 |
| 1186608 | 8809 | 8826 | 90 | 107 | GAGTCCTGCAATATGAAT | 132 | 107 |
| 1186612 | 8813 | 8830 | 94 | 111 | TGCCGAGTCCTGCAATAT | 95 | 108 |
| 1186616 | 8817 | 8834 | 98 | 115 | CTTCTGCCGAGTCCTGCA | 127 | 109 |
| 1186620 | 8821 | 8838 | 102 | 119 | AGGTCTTCTGCCGAGTCC | 181 | 110 |
| 1186624 | 8825 | 8842 | 106 | 123 | TCGAAGGTCTTCTGCCGA | 139 | 111 |
| 1186628 | 8829 | 8846 | 110 | 127 | TCTCTCGAAGGTCTTCTG | 147 | 112 |

TABLE 2-continued

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186632 | 8833 | 8850 | 114 | 131 | CCTTTCTCTCGAAGGTCT | 162 | 113 |
| 1186636 | 8837 | 8854 | 118 | 135 | TCTACCTTTCTCTCGAAG | 170 | 114 |
| 1186640 | 8841 | 8858 | 122 | 139 | ATTTTCTACCTTTCTCTC | 151 | 115 |
| 1186644 | 8845 | 8862 | 126 | 143 | TCTTATTTTCTACCTTTC | 198 | 116 |
| 1186648 | 8849 | 8866 | 130 | 147 | AAATTCTTATTTTCTACC | 160 | 117 |
| 1186652 | 8853 | 8870 | 134 | 151 | AGCCAAATTCTTATTTTC | 186 | 118 |
| 1186656 | 8857 | 8874 | 138 | 155 | AGAGAGCCAAATTCTTAT | 182 | 119 |
| 1186660 | 8861 | 8878 | 142 | 159 | ACACAGAGAGCCAAATTC | 171 | 120 |
| 1186664 | 8865 | 8882 | 146 | 163 | GCTCACACAGAGAGCCAA | 120 | 121 |
| 1186668 | 8869 | 8886 | 150 | 167 | ACATGCTCACACAGAGAG | 133 | 122 |
| 1186672 | 8873 | 8890 | 154 | 171 | GCACACATGCTCACACAG | 166 | 123 |
| 1186676 | 8877 | 8894 | 158 | 175 | ACACGCACACATGCTCAC | 161 | 124 |
| 1186680 | 8881 | 8898 | 162 | 179 | GCACACGCACACATGC | 142 | 125 |
| 1186684 | 8885 | 8902 | 166 | 183 | TCTCGCACACACGCACAC | 125 | 126 |
| 1186688 | 8889 | 8906 | 170 | 187 | TCTCTCTCGCACACACGC | 136 | 127 |
| 1186692 | 8893 | 8910 | 174 | 191 | TCTCTCTCTCGCACAC | 145 | 128 |
| 1186696 | 8897 | 8914 | 178 | 195 | TCTGTCTCTCTCTCGC | 129 | 129 |
| 1186700 | 8901 | 8918 | 182 | 199 | GCTGTCTGTCTCTCTC | 155 | 130 |
| 1186704 | 8905 | 8922 | 186 | 203 | GCAGGCTGTCTGTCTCTC | 138 | 131 |
| 1186708 | 8909 | 8926 | 190 | 207 | TTAGGCAGGCTGTCTGTC | 118 | 132 |
| 1186712 | 8913 | 8930 | 194 | 211 | CTTCTTAGGCAGGCTGTC | 170 | 133 |
| 1186716 | 8917 | 8934 | 198 | 215 | ATTTCTTCTTAGGCAGGC | 188 | 134 |
| 1186720 | 8921 | 8938 | 202 | 219 | ATTCATTTCTTCTTAGGC | 193 | 135 |
| 1186724 | 8925 | 8942 | 206 | 223 | TCACATTCATTTCTTCTT | 196 | 136 |
| 1186728 | 8929 | 8946 | 210 | 227 | GCATTCACATTCATTTCT | 205 | 137 |
| 1186732 | 8933 | 8950 | 214 | 231 | AGCCGCATTCACATTCAT | 120 | 138 |
| 1186736 | 8937 | 8954 | 218 | 235 | CACAAGCCGCATTCACAT | 140 | 139 |
| 1186740 | 8941 | 8958 | 222 | 239 | GTGCCACAAGCCGCATTC | 120 | 140 |
| 1186744 | 8945 | 8962 | 226 | 243 | AACTGTGCCACAAGCCGC | 112 | 141 |
| 1186748 | 8949 | 8966 | 230 | 247 | TGTCAACTGTGCCACAAG | 149 | 142 |
| 1186752 | 8953 | 8970 | 234 | 251 | TCCTTGTCAACTGTGCCA | 151 | 143 |
| 1186756 | 8957 | 8974 | 238 | 255 | ATCATCCTTGTCAACTGT | 164 | 144 |
| 1186760 | 8961 | 8978 | 242 | 259 | ATTTATCATCCTTGTCAA | 166 | 145 |
| 1186764 | 8965 | 8982 | 246 | 263 | ATTGATTTATCATCCTTG | 123 | 146 |
| 1186768 | 8969 | 8986 | 250 | 267 | CATTATTGATTTATCATC | 97 | 147 |

TABLE 2-continued

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186772 | 8973 | 8990 | 254 | 271 | CTTGCATTATTGATTTAT | 60 | 148 |
| 1186776 | 8977 | 8994 | 258 | 275 | TAAGCTTGCATTATTGAT | 58 | 149 |
| 1186780 | 8981 | 8998 | 262 | 279 | ATAGTAAGCTTGCATTAT | 86 | 150 |
| 1186784 | 8985 | 9002 | 266 | 283 | AATGATAGTAAGCTTGCA | 60 | 151 |
| 1186788 | 8989 | 9006 | 270 | 287 | CATAAATGATAGTAAGCT | 75 | 152 |
| 1186792 | 8993 | 9010 | 274 | 291 | TATTCATAAATGATAGTA | 4 | 153 |
| 1186796 | 8997 | 9014 | 278 | 295 | TTGCTATTCATAAATGAT | 46 | 154 |
| 1186800 | 9001 | 9018 | 282 | 299 | AGTATTGCTATTCATAAA | 42 | 155 |
| 1186804 | 9005 | 9022 | 286 | 303 | CTTCAGTATTGCTATTCA | 50 | 156 |
| 1186808 | 9009 | 9026 | 290 | 307 | ATTTCTTCAGTATTGCTA | 97 | 157 |
| 1186812 | 9013 | 9030 | 294 | 311 | TTTAATTTCTTCAGTATT | 133 | 158 |
| 1186816 | 9017 | 9034 | 298 | 315 | TGTTTTAATTTCTTCAG | 141 | 159 |
| 1186820 | 9021 | 9038 | 302 | 319 | TCTTTTGTTTTAATTTCT | 90 | 160 |
| 1186824 | 9025 | 9042 | 306 | 323 | GCAATCTTTTGTTTTAAT | 88 | 161 |
| 1186828 | 9029 | 9046 | 310 | 327 | GACAGCAATCTTTTGTTT | 122 | 162 |
| 1186832 | 9033 | 9050 | 314 | 331 | TTGAGACAGCAATCTTTT | 128 | 163 |
| 1186836 | 9037 | 9054 | 318 | 335 | TATATTGAGACAGCAATC | 105 | 164 |
| 1186840 | 9041 | 9058 | 322 | 339 | AAGATATATTGAGACAGC | 124 | 165 |

TABLE 3

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186533 | 8734 | 8751 | 15 | 32 | GTAATAAAATCCCCAGGT | 84 | 166 |
| 1186537 | 8738 | 8755 | 19 | 36 | CAGAGTAATAAAATCCCC | 117 | 167 |
| 1186541 | 8742 | 8759 | 23 | 40 | TTCCCAGAGTAATAAAAT | 73 | 168 |
| 1186545 | 8746 | 8763 | 27 | 44 | ATAATTCCCAGAGTAATA | 72 | 169 |
| 1186549 | 8750 | 8767 | 31 | 48 | ACACATAATTCCCAGAGT | 76 | 170 |
| 1186553 | 8754 | 8771 | 35 | 52 | CAGAACACATAATTCCCA | 78 | 171 |
| 1186557 | 8758 | 8775 | 39 | 56 | GGGGCAGAACACATAATT | 66 | 172 |
| 1186561 | 8762 | 8779 | 43 | 60 | TGATGGGGCAGAACACAT | 87 | 173 |
| 1186565 | 8766 | 8783 | 47 | 64 | AGAGTGATGGGGCAGAAC | 97 | 174 |
| 1186569 | 8770 | 8787 | 51 | 68 | AGAGAGAGTGATGGGGCA | 94 | 175 |
| 1186573 | 8774 | 8791 | 55 | 72 | ATTAAGAGAGAGTGATGG | 128 | 176 |

TABLE 3-continued

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186577 | 8778 | 8795 | 59 | 76 | TCCAATTAAGAGAGAGTG | 164 | 177 |
| 1186581 | 8782 | 8799 | 63 | 80 | AAAATCCAATTAAGAGAG | 145 | 178 |
| 1186585 | 8786 | 8803 | 67 | 84 | TTTAAAAATCCAATTAAG | 128 | 179 |
| 1186589 | 8790 | 8807 | 71 | 88 | TAATTTTAAAAATCCAAT | 117 | 180 |
| 1186593 | 8794 | 8811 | 75 | 92 | AATATAATTTTAAAAATC | 79 | 181 |
| 1186597 | 8798 | 8815 | 79 | 96 | TATGAATATAATTTTAAA | 83 | 182 |
| 1186601 | 8802 | 8819 | 83 | 100 | GCAATATGAATATAATTT | 143 | 183 |
| 1186605 | 8806 | 8823 | 87 | 104 | TCCTGCAATATGAATATA | 190 | 184 |
| 1186609 | 8810 | 8827 | 91 | 108 | CGAGTCCTGCAATATGAA | 149 | 185 |
| 1186613 | 8814 | 8831 | 95 | 112 | CTGCCGAGTCCTGCAATA | 189 | 186 |
| 1186617 | 8818 | 8835 | 99 | 116 | TCTTCTGCCGAGTCCTGC | 99 | 187 |
| 1186621 | 8822 | 8839 | 103 | 120 | AAGGTCTTCTGCCGAGTC | 168 | 188 |
| 1186625 | 8826 | 8843 | 107 | 124 | CTCGAAGGTCTTCTGCCG | 127 | 189 |
| 1186629 | 8830 | 8847 | 111 | 128 | TTCTCTCGAAGGTCTTCT | 232 | 190 |
| 1186633 | 8834 | 8851 | 115 | 132 | ACCTTTCTCTCGAAGGTC | 146 | 191 |
| 1186637 | 8838 | 8855 | 119 | 136 | TTCTACCTTTCTCTCGAA | 230 | 192 |
| 1186641 | 8842 | 8859 | 123 | 140 | TATTTTCTACCTTTCTCT | 163 | 193 |
| 1186645 | 8846 | 8863 | 127 | 144 | TTCTTATTTTCTACCTTT | 176 | 194 |
| 1186649 | 8850 | 8867 | 131 | 148 | CAAATTCTTATTTTCTAC | 133 | 195 |
| 1186653 | 8854 | 8871 | 135 | 152 | GAGCCAAATTCTTATTTT | 172 | 196 |
| 1186657 | 8858 | 8875 | 139 | 156 | CAGAGAGCCAAATTCTTA | 174 | 197 |
| 1186661 | 8862 | 8879 | 143 | 160 | CACACAGAGAGCCAAATT | 204 | 198 |
| 1186665 | 8866 | 8883 | 147 | 164 | TGCTCACACAGAGAGCCA | 134 | 199 |
| 1186669 | 8870 | 8887 | 151 | 168 | CACATGCTCACACAGAGA | 150 | 200 |
| 1186673 | 8874 | 8891 | 155 | 172 | CGCACACATGCTCACACA | 154 | 201 |
| 1186677 | 8878 | 8895 | 159 | 176 | CACACGCACACATGCTCA | 150 | 202 |
| 1186681 | 8882 | 8899 | 163 | 180 | CGCACACACGCACACATG | 148 | 203 |
| 1186685 | 8886 | 8903 | 167 | 184 | CTCTCGCACACACGCACA | 142 | 204 |
| 1186689 | 8890 | 8907 | 171 | 188 | CTCTCTCGCACACACG | 211 | 205 |
| 1186693 | 8894 | 8911 | 175 | 192 | GTCTCTCTCTCGCACA | 156 | 206 |
| 1186697 | 8898 | 8915 | 179 | 196 | GTCTGTCTCTCTCTCG | 119 | 207 |
| 1186701 | 8902 | 8919 | 183 | 200 | GGCTGTCTGTCTCTCT | 155 | 208 |
| 1186705 | 8906 | 8923 | 187 | 204 | GGCAGGCTGTCTGTCT | 112 | 209 |
| 1186709 | 8910 | 8927 | 191 | 208 | CTTAGGCAGGCTGTCTGT | 112 | 210 |
| 1186713 | 8914 | 8931 | 195 | 212 | TCTTCTTAGGCAGGCTGT | 170 | 211 |

TABLE 3-continued

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186717 | 8918 | 8935 | 199 | 216 | CATTTCTTCTTAGGCAGG | 193 | 212 |
| 1186721 | 8922 | 8939 | 203 | 220 | CATTCATTTCTTCTTAGG | 157 | 213 |
| 1186725 | 8926 | 8943 | 207 | 224 | TTCACATTCATTTCTTCT | 161 | 214 |
| 1186729 | 8930 | 8947 | 211 | 228 | CGCATTCACATTCATTTC | 228 | 215 |
| 1186733 | 8934 | 8951 | 215 | 232 | AAGCCGCATTCACATTCA | 164 | 216 |
| 1186737 | 8938 | 8955 | 219 | 236 | CCACAAGCCGCATTCACA | 171 | 217 |
| 1186741 | 8942 | 8959 | 223 | 240 | TGTGCCACAAGCCGCATT | 141 | 218 |
| 1186745 | 8946 | 8963 | 227 | 244 | CAACTGTGCCACAAGCCG | 135 | 219 |
| 1186749 | 8950 | 8967 | 231 | 248 | TTGTCAACTGTGCCACAA | 144 | 220 |
| 1186753 | 8954 | 8971 | 235 | 252 | ATCCTTGTCAACTGTGCC | 127 | 221 |
| 1186757 | 8958 | 8975 | 239 | 256 | TATCATCCTTGTCAACTG | 169 | 222 |
| 1186761 | 8962 | 8979 | 243 | 260 | GATTTATCATCCTTGTCA | 157 | 223 |
| 1186765 | 8966 | 8983 | 247 | 264 | TATTGATTTATCATCCTT | 113 | 224 |
| 1186769 | 8970 | 8987 | 251 | 268 | GCATTATTGATTTATCAT | 37 | 225 |
| 1186773 | 8974 | 8991 | 255 | 272 | GCTTGCATTATTGATTTA | 68 | 226 |
| 1186777 | 8978 | 8995 | 259 | 276 | GTAAGCTTGCATTATTGA | 63 | 227 |
| 1186781 | 8982 | 8999 | 263 | 280 | GATAGTAAGCTTGCATTA | 70 | 228 |
| 1186785 | 8986 | 9003 | 267 | 284 | AAATGATAGTAAGCTTGC | 63 | 229 |
| 1186789 | 8990 | 9007 | 271 | 288 | TCATAAATGATAGTAAGC | 7 | 230 |
| 1186793 | 8994 | 9011 | 275 | 292 | CTATTCATAAATGATAGT | 65 | 231 |
| 1186797 | 8998 | 9015 | 279 | 296 | ATTGCTATTCATAAATGA | 37 | 232 |
| 1186801 | 9002 | 9019 | 283 | 300 | CAGTATTGCTATTCATAA | 71 | 233 |
| 1186805 | 9006 | 9023 | 287 | 304 | TCTTCAGTATTGCTATTC | 94 | 234 |
| 1186809 | 9010 | 9027 | 291 | 308 | AATTTCTTCAGTATTGCT | 96 | 235 |
| 1186813 | 9014 | 9031 | 295 | 312 | TTTTAATTTCTTCAGTAT | 98 | 236 |
| 1186817 | 9018 | 9035 | 299 | 316 | TTTGTTTTAATTTCTTCA | 99 | 237 |
| 1186821 | 9022 | 9039 | 303 | 320 | ATCTTTTGTTTTAATTTC | 114 | 238 |
| 1186825 | 9026 | 9043 | 307 | 324 | AGCAATCTTTTGTTTTAA | 116 | 239 |
| 1186829 | 9030 | 9047 | 311 | 328 | AGACAGCAATCTTTTGTT | 130 | 240 |
| 1186833 | 9034 | 9051 | 315 | 332 | ATTGAGACAGCAATCTTT | 101 | 241 |
| 1186837 | 9038 | 9055 | 319 | 336 | ATATATTGAGACAGCAAT | 98 | 242 |
| 1186841 | 9042 | 9059 | 323 | 340 | TAAGATATATTGAGACAG | 95 | 243 |

TABLE 4

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186534 | 8735 | 8752 | 16 | 33 | AGTAATAAAATCCCCAGG | 71 | 244 |
| 1186538 | 8739 | 8756 | 20 | 37 | CCAGAGTAATAAAATCCC | 65 | 245 |
| 1186542 | 8743 | 8760 | 24 | 41 | ATTCCCAGAGTAATAAAA | 86 | 246 |
| 1186546 | 8747 | 8764 | 28 | 45 | CATAATTCCCAGAGTAAT | 69 | 247 |
| 1186550 | 8751 | 8768 | 32 | 49 | AACACATAATTCCCAGAG | 76 | 248 |
| 1186554 | 8755 | 8772 | 36 | 53 | GCAGAACACATAATTCCC | 95 | 249 |
| 1186558 | 8759 | 8776 | 40 | 57 | TGGGGCAGAACACATAAT | 88 | 250 |
| 1186562 | 8763 | 8780 | 44 | 61 | GTGATGGGGCAGAACACA | 89 | 251 |
| 1186566 | 8767 | 8784 | 48 | 65 | GAGAGTGATGGGGCAGAA | 95 | 252 |
| 1186570 | 8771 | 8788 | 52 | 69 | AAGAGAGAGTGATGGGGC | 98 | 253 |
| 1186574 | 8775 | 8792 | 56 | 73 | AATTAAGAGAGAGTGATG | 121 | 254 |
| 1186578 | 8779 | 8796 | 60 | 77 | ATCCAATTAAGAGAGAGT | 164 | 255 |
| 1186582 | 8783 | 8800 | 64 | 81 | AAAAATCCAATTAAGAGA | 137 | 256 |
| 1186586 | 8787 | 8804 | 68 | 85 | TTTTAAAAATCCAATTAA | 99 | 257 |
| 1186590 | 8791 | 8808 | 72 | 89 | ATAATTTTAAAAATCCAA | 106 | 258 |
| 1186594 | 8795 | 8812 | 76 | 93 | GAATATAATTTTAAAAAT | 95 | 259 |
| 1186598 | 8799 | 8816 | 80 | 97 | ATATGAATATAATTTTAA | 81 | 260 |
| 1186602 | 8803 | 8820 | 84 | 101 | TGCAATATGAATATAATT | 154 | 261 |
| 1186606 | 8807 | 8824 | 88 | 105 | GTCCTGCAATATGAATAT | 166 | 262 |
| 1186610 | 8811 | 8828 | 92 | 109 | CCGAGTCCTGCAATATGA | 159 | 263 |
| 1186614 | 8815 | 8832 | 96 | 113 | TCTGCCGAGTCCTGCAAT | 129 | 264 |
| 1186618 | 8819 | 8836 | 100 | 117 | GTCTTCTGCCGAGTCCTG | 151 | 265 |
| 1186622 | 8823 | 8840 | 104 | 121 | GAAGGTCTTCTGCCGAGT | 208 | 266 |
| 1186626 | 8827 | 8844 | 108 | 125 | TCTCGAAGGTCTTCTGCC | 165 | 267 |
| 1186630 | 8831 | 8848 | 112 | 129 | TTTCTCTCGAAGGTCTTC | 176 | 268 |
| 1186634 | 8835 | 8852 | 116 | 133 | TACCTTTCTCTCGAAGGT | 123 | 269 |
| 1186638 | 8839 | 8856 | 120 | 137 | TTTCTACCTTTCTCTCGA | 152 | 270 |
| 1186642 | 8843 | 8860 | 124 | 141 | TTATTTTCTACCTTTCTC | 137 | 271 |
| 1186646 | 8847 | 8864 | 128 | 145 | ATTCTTATTTTCTACCTT | 191 | 272 |
| 1186650 | 8851 | 8868 | 132 | 149 | CCAAATTCTTATTTTCTA | 167 | 273 |
| 1186654 | 8855 | 8872 | 136 | 153 | AGAGCCAAATTCTTATTT | 172 | 274 |
| 1186658 | 8859 | 8876 | 140 | 157 | ACAGAGAGCCAAATTCTT | 172 | 275 |
| 1186662 | 8863 | 8880 | 144 | 161 | TCACACAGAGAGCCAAAT | 159 | 276 |
| 1186666 | 8867 | 8884 | 148 | 165 | ATGCTCACACAGAGAGCC | 126 | 277 |
| 1186670 | 8871 | 8888 | 152 | 169 | ACACATGCTCACACAGAG | 142 | 278 |
| 1186674 | 8875 | 8892 | 156 | 173 | ACGCACACATGCTCACAC | 170 | 279 |

TABLE 4-continued

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186678 | 8879 | 8896 | 160 | 177 | ACACACGCACACATGCTC | 122 | 280 |
| 1186682 | 8883 | 8900 | 164 | 181 | TCGCACACACGCACACAT | 133 | 281 |
| 1186686 | 8887 | 8904 | 168 | 185 | TCTCTCGCACACACGCAC | 145 | 282 |
| 1186690 | 8891 | 8908 | 172 | 189 | TCTCTCTCTCGCACACAC | 134 | 283 |
| 1186694 | 8895 | 8912 | 176 | 193 | TGTCTCTCTCTCTCGCAC | 116 | 284 |
| 1186698 | 8899 | 8916 | 180 | 197 | TGTCTGTCTCTCTCTCTC | 171 | 285 |
| 1186702 | 8903 | 8920 | 184 | 201 | AGGCTGTCTGTCTCTCTC | 141 | 286 |
| 1186706 | 8907 | 8924 | 188 | 205 | AGGCAGGCTGTCTGTCTC | 139 | 287 |
| 1186710 | 8911 | 8928 | 192 | 209 | TCTTAGGCAGGCTGTCTG | 127 | 288 |
| 1186714 | 8915 | 8932 | 196 | 213 | TTCTTCTTAGGCAGGCTG | 150 | 289 |
| 1186718 | 8919 | 8936 | 200 | 217 | TCATTTCTTCTTAGGCAG | 215 | 290 |
| 1186722 | 8923 | 8940 | 204 | 221 | ACATTCATTTCTTCTTAG | 185 | 291 |
| 1186726 | 8927 | 8944 | 208 | 225 | ATTCACATTCATTTCTTC | 174 | 292 |
| 1186730 | 8931 | 8948 | 212 | 229 | CCGCATTCACATTCATTT | 161 | 293 |
| 1186734 | 8935 | 8952 | 216 | 233 | CAAGCCGCATTCACATTC | 150 | 294 |
| 1186738 | 8939 | 8956 | 220 | 237 | GCCACAAGCCGCATTCAC | 122 | 295 |
| 1186742 | 8943 | 8960 | 224 | 241 | CTGTGCCACAAGCCGCAT | 210 | 296 |
| 1186746 | 8947 | 8964 | 228 | 245 | TCAACTGTGCCACAAGCC | 181 | 297 |
| 1186750 | 8951 | 8968 | 232 | 249 | CTTGTCAACTGTGCCACA | 153 | 298 |
| 1186754 | 8955 | 8972 | 236 | 253 | CATCCTTGTCAACTGTGC | 107 | 299 |
| 1186758 | 8959 | 8976 | 240 | 257 | TTATCATCCTTGTCAACT | 164 | 300 |
| 1186762 | 8963 | 8980 | 244 | 261 | TGATTTATCATCCTTGTC | 138 | 301 |
| 1186766 | 8967 | 8984 | 248 | 265 | TTATTGATTTATCATCCT | 100 | 302 |
| 1186770 | 8971 | 8988 | 252 | 269 | TGCATTATTGATTTATCA | 53 | 303 |
| 1186774 | 8975 | 8992 | 256 | 273 | AGCTTGCATTATTGATTT | 57 | 304 |
| 1186778 | 8979 | 8996 | 260 | 277 | AGTAAGCTTGCATTATTG | 70 | 305 |
| 1186782 | 8983 | 9000 | 264 | 281 | TGATAGTAAGCTTGCATT | 72 | 306 |
| 1186786 | 8987 | 9004 | 268 | 285 | TAAATGATAGTAAGCTTG | 46 | 307 |
| 1186790 | 8991 | 9008 | 272 | 289 | TTCATAAATGATAGTAAG | 37 | 308 |
| 1186794 | 8995 | 9012 | 276 | 293 | GCTATTCATAAATGATAG | 37 | 309 |
| 1186798 | 8999 | 9016 | 280 | 297 | TATTGCTATTCATAAATG | 44 | 310 |
| 1186802 | 9003 | 9020 | 284 | 301 | TCAGTATTGCTATTCATA | 62 | 311 |
| 1186806 | 9007 | 9024 | 288 | 305 | TTCTTCAGTATTGCTATT | 55 | 312 |
| 1186810 | 9011 | 9028 | 292 | 309 | TAATTCTTCAGTATTGC | 82 | 313 |
| 1186814 | 9015 | 9032 | 296 | 313 | GTTTAATTTCTTCAGTA | 101 | 314 |

TABLE 4-continued

Percent control of human STMN2 RNA with uniformly MOE modified oligonucleotides with phosphorothioate internucleoside linkages

| Compound Number | SEQ ID NO: 1 Start Site | SEQ ID NO: 1 Stop Site | SEQ ID NO: 2 Start Site | SEQ ID NO: 2 Stop Site | Sequence (5' to 3') | STMN2 (% control) | SEQ ID NO |
|---|---|---|---|---|---|---|---|
| 1186818 | 9019 | 9036 | 300 | 317 | TTTTGTTTTAATTTCTTC | 104 | 315 |
| 1186822 | 9023 | 9040 | 304 | 321 | AATCTTTTGTTTTAATTT | 97 | 316 |
| 1186826 | 9027 | 9044 | 308 | 325 | CAGCAATCTTTTGTTTTA | 157 | 317 |
| 1186830 | 9031 | 9048 | 312 | 329 | GAGACAGCAATCTTTTGT | 120 | 318 |
| 1186834 | 9035 | 9052 | 316 | 333 | TATTGAGACAGCAATCTT | 97 | 319 |
| 1186838 | 9039 | 9056 | 320 | 337 | GATATATTGAGACAGCAA | 110 | 320 |
| 1186842 | 9043 | 9060 | 324 | 341 | ATAAGATATATTGAGACA | 100 | 321 |

Example 2: Effect of Uniformly MOE Modified Oligonucleotides with Phosphorothioate Internucleoside Linkages on Human STMN2 In Vitro, Multiple Doses Modified oligonucleotides selected from the example above were tested at various doses in CRISPR-edited SH-SY5Y cells (described hereinabove in Example 1). Cells were plated at a density of 20,000 cells per well and transfected using electroporation with 555 nM, 1,666 nM, 5,000 nM, and 15,000 nM concentrations of modified oligonucleotide, as specified in the tables below. After a treatment period of approximately 24 hours, total RNA was isolated from the cells and STMN2 RNA levels were measured by quantitative real-time PCR. Human STMN2 primer probe set RTS40280 (described hereinabove in Example 1) was used to measure RNA levels. STMN2 RNA levels were adjusted according to total RNA content, as measured by RiboGreen®. Results are presented in the tables below as percent control of the amount of STMN2 RNA, relative to untreated control cells. As illustrated in the tables below, STMN2 RNA levels were increased in a dose-dependent manner in modified oligonucleotide-treated cells. IC50 was calculated using the "log(agonist) vs. response—variable slope (4 parameters)" formula using Prism6 software (Min=100, Max=249).

TABLE 5

Dose-dependent percent increase of human STMN2 RNA by uniformly modified oligonucleotides

| Compound Number | STMN2 (% control) | | | | $IC_{50}$ (nM) |
|---|---|---|---|---|---|
| | 555 nM | 1,666 nM | 5,000 nM | 15,000 nM | |
| 1186604 | 127 | 146 | 187 | 206 | 4009 |
| 1186607 | 126 | 126 | 174 | 201 | 6053 |
| 1186627 | 103 | 130 | 176 | 202 | 5912 |
| 1186629 | 130 | 149 | 181 | 213 | 3814 |
| 1186644 | 97 | 154 | 166 | 194 | 6577 |
| 1186651 | 129 | 151 | 184 | 217 | 3479 |
| 1186652 | 139 | 186 | 198 | 223 | 1654 |
| 1186655 | 121 | 162 | 183 | 201 | 3956 |
| 1186656 | 135 | 188 | 225 | 239 | 1322 |
| 1186671 | 106 | 132 | 160 | 196 | 7706 |
| 1186712 | 136 | 145 | 171 | 209 | 4601 |

TABLE 5-continued

Dose-dependent percent increase of human STMN2 RNA by uniformly modified oligonucleotides

| Compound Number | STMN2 (% control) | | | | $IC_{50}$ (nM) |
|---|---|---|---|---|---|
| | 555 nM | 1,666 nM | 5,000 nM | 15,000 nM | |
| 1186715 | 112 | 134 | 165 | 233 | 4889 |
| 1186716 | 141 | 174 | 198 | 212 | 2033 |
| 1186720 | 118 | 176 | 212 | 208 | 2191 |
| 1186723 | 135 | 165 | 203 | 213 | 2311 |
| 1186724 | 132 | 167 | 193 | 204 | 2858 |
| 1186727 | 76 | 171 | 195 | 230 | 2838 |
| 1186728 | 135 | 128 | 179 | 186 | 7285 |
| 1186751 | 113 | 122 | 140 | 150 | n.d.* |

*$IC_{50}$ above maximum dose tested

TABLE 6

Dose-dependent percent increase of human STMN2 RNA by uniformly modified oligonucleotides

| Compound Number | STMN2 expression (% control) | | | | $IC_{50}$ (nM) |
|---|---|---|---|---|---|
| | 555 nM | 1,666 nM | 5,000 nM | 15,000 nM | |
| 1186605 | 126 | 148 | 183 | 229 | 3377 |
| 1186613 | 111 | 127 | 174 | 225 | 4889 |
| 1186622 | 113 | 140 | 170 | 205 | 5637 |
| 1186637 | 111 | 134 | 172 | 221 | 4899 |
| 1186645 | 150 | 172 | 197 | 235 | 1646 |
| 1186646 | 131 | 163 | 202 | 224 | 2314 |
| 1186655 | 176 | 186 | 197 | 217 | 596 |
| 1186657 | 124 | 157 | 175 | 142 | n/a* |
| 1186661 | 133 | 164 | 187 | 247 | 2330 |
| 1186670 | 146 | 152 | 166 | 193 | 6059 |
| 1186689 | 103 | 95 | 166 | 202 | 7529 |
| 1186698 | 122 | 116 | 154 | 182 | 11593 |
| 1186717 | 160 | 192 | 217 | 213 | 873 |
| 1186718 | 145 | 163 | 210 | 195 | 2255 |
| 1186722 | 123 | 180 | 193 | 220 | 2286 |
| 1186726 | 155 | 187 | 228 | 249 | 1024 |
| 1186729 | 148 | 171 | 209 | 231 | 1575 |
| 1186742 | 82 | 122 | 135 | 181 | 12831 |
| 1186746 | 132 | 156 | 166 | 209 | 4499 |

*$IC_{50}$ above maximum dose tested

Example 3: Effect of Uniformly MOE Modified Oligonucleotides with Phosphorothioate Internucleoside Linkages on Human STMN2 In Vitro, Multiple Doses Modified oligonucleotides selected from the examples above were tested at various doses in CRISPR-edited SH-SY5Y cells (described hereinabove in Example 1). Cells were plated at a density of 20,000 cells per well and transfected using electroporation with 555 nM, 1,666 nM, 5,000 nM, and 15,000 nM concentrations of modified oligonucleotide, as specified in the tables below. After a treatment period of approximately 24 hours, total RNA was isolated from the cells and STMN2 RNA levels were measured by quantitative real-time PCR. Human STMN2 primer probe set RTS41911 (forward sequence AAGGCAATCCTGCCTACTAAC, designated herein as SEQ ID NO: 6; reverse sequence GGTGGGTATCTGGTGATTCTTAG, designated herein as SEQ ID NO: 7; probe sequence TCCATCTGTGAAGCTGACGCAGTT, designated herein as SEQ ID NO: 8) was used to measure RNA levels. STMN2 RNA levels were adjusted according to total RNA content, as measured by RiboGreen®. Results are presented in the tables below as percent control of the amount of STMN2 RNA, relative to untreated control cells. As illustrated in the tables below, STMN2 RNA levels were increased in a dose-dependent manner in modified oligonucleotide-treated cells. $IC_{50}$ was calculated using the "log (agonist) vs. response—variable slope (4 parameters)" formula using Prism6 software (Min=100, Max=249).

TABLE 7

Dose-dependent percent increase of human STMN2 RNA by uniformly modified oligonucleotides

| Compound Number | STMN2 (% control) | | | | $IC_{50}$ (nM) |
|---|---|---|---|---|---|
| | 555 nM | 1,666 nM | 5,000 nM | 15,000 nM | |
| 1186604 | 114 | 144 | 165 | 202 | 6077 |
| 1186607 | 107 | 109 | 137 | 187 | 11626 |
| 1186627 | 96 | 120 | 154 | 188 | 9775 |
| 1186629 | 125 | 150 | 177 | 202 | 4710 |
| 1186644 | 130 | 160 | 159 | 198 | 5939 |
| 1186651 | 125 | 139 | 171 | 205 | 5411 |
| 1186652 | 148 | 175 | 191 | 196 | 2296 |
| 1186655 | 128 | 156 | 220 | 195 | 2610 |

TABLE 7-continued

Dose-dependent percent increase of human STMN2 RNA by uniformly modified oligonucleotides

| Compound Number | STMN2 (% control) | | | | $IC_{50}$ (nM) |
|---|---|---|---|---|---|
| | 555 nM | 1,666 nM | 5,000 nM | 15,000 nM | |
| 1186656 | 129 | 173 | 200 | 200 | 2587 |
| 1186671 | 100 | 116 | 129 | 166 | n/a* |
| 1186712 | 121 | 116 | 159 | 193 | 8686 |
| 1186715 | 100 | 124 | 156 | 211 | 6931 |
| 1186716 | 136 | 148 | 174 | 189 | 6209 |
| 1186720 | 111 | 170 | 194 | 205 | 3150 |
| 1186723 | 118 | 145 | 161 | 203 | 6204 |
| 1186724 | 145 | 161 | 188 | 203 | 2924 |
| 1186727 | 128 | 162 | 190 | 212 | 3011 |
| 1186728 | 124 | 120 | 168 | 171 | 13516 |
| 1186751 | 112 | 121 | 146 | 130 | n.d.** |

*$IC_{50}$ above maximum dose tested
**$IC_{50}$ cannot be calculated

TABLE 8

Dose-dependent percent increase of human STMN2 RNA by uniformly modified oligonucleotides

| Compound Number | STMN2 (% control) | | | | $IC_{50}$ (nM) |
|---|---|---|---|---|---|
| | 555 nM | 1,666 nM | 5,000 nM | 15,000 nM | |
| 1186605 | 123 | 134 | 199 | 231 | 3304 |
| 1186613 | 113 | 124 | 181 | 228 | 4516 |
| 1186622 | 137 | 157 | 207 | 223 | 2254 |
| 1186637 | 111 | 139 | 192 | 238 | 3430 |
| 1186645 | 118 | 149 | 179 | 210 | 4313 |
| 1186646 | 140 | 177 | 208 | 238 | 1594 |
| 1186655 | 158 | 191 | 215 | 227 | 970 |
| 1186657 | 130 | 159 | 185 | 196 | 4042 |
| 1186661 | 141 | 182 | 208 | 238 | 1481 |
| 1186670 | 129 | 157 | 175 | 200 | 4558 |
| 1186689 | 108 | 135 | 180 | 212 | 4833 |
| 1186698 | 113 | 122 | 172 | 181 | 9174 |
| 1186717 | 143 | 190 | 205 | 214 | 1433 |
| 1186718 | 150 | 170 | 230 | 208 | 1402 |
| 1186722 | 119 | 159 | 192 | 203 | 3553 |
| 1186726 | 137 | 169 | 205 | 214 | 2087 |
| 1186729 | 147 | 180 | 208 | 215 | 1503 |
| 1186742 | 113 | 124 | 145 | 184 | 11785 |
| 1186746 | 135 | 149 | 179 | 206 | 4126 |

The invention claimed is:

1. An oligomeric compound comprising a modified oligonucleotide consisting of 12 to 50 linked nucleosides and having a nucleobase sequence comprising at least 15, at least 16, at least 17, or at least 18 consecutive nucleobases of a nucleobase sequence selected from SEQ ID NOs: 32, 33, 110, 188, 265, and 266, wherein the modified oligonucleotide comprises at least one modified internucleoside linkage and/or at least one modified nucleoside comprising a modified sugar moiety.

2. An oligomeric compound comprising a modified oligonucleotide consisting of 12 to 50 linked nucleosides and having a nucleobase sequence comprising at least 15, at least 16, at least 17, or at least 18 consecutive nucleobases complementary to: nucleobases 8819-8841 of SEQ ID NO: 1 or nucleobases 100-122 of SEQ ID NO: 2, wherein the modified oligonucleotide comprises at least one modified internucleoside linkage and/or at least one modified nucleoside comprising a modified sugar moiety.

3. The oligomeric compound of claim 2, wherein the modified oligonucleotide is a single-stranded modified oligonucleotide.

4. The oligomeric compound of claim 2, wherein at least one internucleoside linkage of the modified oligonucleotide is a modified internucleoside linkage.

5. The oligomeric compound of claim 4, wherein the modified internucleoside linkage is a phosphorothioate internucleoside linkage.

6. The oligomeric compound of claim 2, wherein each internucleoside linkage of the modified oligonucleotide is a modified internucleoside linkage.

7. The oligomeric compound of claim 6, wherein each modified internucleoside linkage of the modified oligonucleotide is a phosphorothioate internucleoside linkage.

8. The oligomeric compound of claim 2, wherein at least one internucleoside linkage of the modified oligonucleotide is a phosphodiester internucleoside linkage.

9. The oligomeric compound of claim 2, wherein each internucleoside linkage of the modified oligonucleotide is, independently, a phosphodiester internucleoside linkage or a phosphorothioate internucleoside linkage.

10. The oligomeric compound of claim 2, wherein at least one nucleobase of the modified oligonucleotide is a modified nucleobase.

11. The oligomeric compound of claim 10, wherein the modified nucleobase is a 5-methylcytosine.

12. The oligomeric compound of claim 2, wherein the modified oligonucleotide comprises at least 1, at least 2, at least 3, at least 4, at least 5, at least 6, at least 7, at least 8, at least 9, at least 10, at least 11, at least 12, at least 13, at least 14, at least 15, at least 16, at least 17, or at least 18 modified nucleosides comprising a modified sugar moiety.

13. The oligomeric compound of claim 12, wherein the modified oligonucleotide comprises at least 1, at least 2, at least 3, at least 4, at least 5, at least 6, at least 7, at least 8, at least 9, at least 10, at least 11, at least 12, at least 13, at least 14, at least 15, at least 16, at least 17, or at least 18 modified nucleosides comprising a bicyclic sugar moiety.

14. The oligomeric compound of claim 13, wherein the modified oligonucleotide comprises at least 1 modified nucleoside comprising a bicyclic sugar moiety having a 2'-4' bridge, wherein the 2'-4' bridge is selected from —O—CH$_2$—; and —O—CH(CH$_3$)—.

15. The oligomeric compound of claim 2, wherein the modified oligonucleotide comprises at least 1 modified nucleoside comprising a non-bicyclic sugar moiety.

16. The oligomeric compound of claim 15, wherein the modified oligonucleotide comprises at least 1 modified nucleoside comprising a 2'-OCH$_2$CH$_2$OCH$_3$ ribosyl sugar moiety or a 2'-OMe sugar moiety.

17. The oligomeric compound of claim 16, wherein each modified nucleoside of the modified oligonucleotide comprises a 2'-OCH$_2$CH$_2$OCH$_3$ ribosyl sugar moiety or a 2'-OMe sugar moiety.

18. The oligomeric compound of claim 2, wherein the modified oligonucleotide comprises at least 1 modified nucleoside comprising a sugar surrogate.

19. The oligomeric compound of claim 18, wherein the modified oligonucleotide comprises at least 1 modified nucleoside comprising a sugar surrogate selected from morpholino and PNA.

20. The oligomeric compound of claim 2, wherein the modified oligonucleotide consists of 20 linked nucleosides and has the following internucleoside linkage motif: sooosssssssssssooss; wherein,
s=a phosphorothioate internucleoside linkage, and
o=a phosphodiester internucleoside linkage.

21. The oligomeric compound of claim 2, wherein the modified oligonucleotide consists of 12-18, 12-20, 14-20, 16-20, or 17-19 linked nucleosides.

22. The oligomeric compound of claim 2, wherein the modified oligonucleotide consists of 16, 17, or 18 linked nucleosides.

23. The oligomeric compound of claim 2, which consists of the modified oligonucleotide.

24. The oligomeric compound of claim 2 comprising a conjugate group comprising a conjugate moiety and a conjugate linker.

25. The oligomeric compound of claim 24, wherein the conjugate linker consists of a single bond.

26. The oligomeric compound of claim 24, wherein the conjugate linker is cleavable.

27. The oligomeric compound of claim 24, wherein the conjugate linker comprises 1-3 linker-nucleosides.

28. The oligomeric compound of claim 24, wherein the conjugate group is attached to the modified oligonucleotide at the 5'-end of the modified oligonucleotide.

29. The oligomeric compound of claim 24, wherein the conjugate group is attached to the modified oligonucleotide at the 3'-end of the modified oligonucleotide.

30. The oligomeric compound of claim 2 comprising a terminal group.

31. The oligomeric compound of claim 2, wherein the oligomeric compound is a single-stranded oligomeric compound.

32. The oligomeric compound of claim 24, wherein the conjugate linker does not comprise linker-nucleosides.

33. An oligomeric duplex comprising the oligomeric compound of claim 2.

34. An antisense compound comprising or consisting of the oligomeric compound of claim 2.

35. A modified oligonucleotide consisting of 12 to 50 linked nucleosides and having a nucleobase sequence comprising at least 15, at least 16, at least 17, or at least 18 consecutive nucleobases of a nucleobase sequence selected from SEQ ID NOs: 32, 33, 110, 188, 265, and 266, wherein the modified oligonucleotide comprises at least one modified internucleoside linkage and/or at least one modified nucleoside comprising a modified sugar moiety.

36. A pharmaceutical composition comprising the oligomeric compound of claim 2 and at least one pharmaceutically acceptable carrier or diluent.

* * * * *